US011439344B2

(12) United States Patent
Zhang et al.

(10) Patent No.: US 11,439,344 B2
(45) Date of Patent: Sep. 13, 2022

(54) METHOD, APPARATUS, AND SYSTEM FOR WIRELESS SLEEP MONITORING

(71) Applicants: Feng Zhang, Greenbelt, MD (US); Beibei Wang, Clarksville, MD (US); Chenshu Wu, Greenbelt, MD (US); Min Wu, Clarksville, MD (US); Dan Bugos, Washington, DC (US); Hangfang Zhang, Greenbelt, MD (US); K. J. Ray Liu, Potomac, MD (US); Oscar Chi-Lim Au, San Jose, CA (US)

(72) Inventors: Feng Zhang, Greenbelt, MD (US); Beibei Wang, Clarksville, MD (US); Chenshu Wu, Greenbelt, MD (US); Min Wu, Clarksville, MD (US); Dan Bugos, Washington, DC (US); Hangfang Zhang, Greenbelt, MD (US); K. J. Ray Liu, Potomac, MD (US); Oscar Chi-Lim Au, San Jose, CA (US)

(73) Assignee: ORIGIN WIRELESS, INC., Greenbelt, MD (US)

(*) Notice: Subject to any disclaimer, the term of this patent is extended or adjusted under 35 U.S.C. 154(b) by 0 days.

(21) Appl. No.: 16/945,837

(22) Filed: Aug. 1, 2020

(65) Prior Publication Data

US 2020/0397365 A1 Dec. 24, 2020

Related U.S. Application Data

(63) Continuation-in-part of application No. 15/326,112, filed as application No. PCT/US2015/041037 on Jul. (Continued)

(51) Int. Cl.
*A61B 5/00* (2006.01)
*A61B 5/113* (2006.01)

(52) U.S. Cl.
CPC .......... *A61B 5/4809* (2013.01); *A61B 5/0004* (2013.01); *A61B 5/113* (2013.01); *A61B 5/4818* (2013.01); *A61B 5/6887* (2013.01)

(58) Field of Classification Search
CPC combination set(s) only.
See application file for complete search history.

(56) References Cited

U.S. PATENT DOCUMENTS 10,314,407 B1 * 6/2019 Main .................... A47C 27/083
10,690,763 B2 * 6/2020 Shouldice ............ A61B 5/0205
(Continued)

OTHER PUBLICATIONS

Liu et al., "Tracking Vital Signs During Sleep Leveraging Off-the-shelf WiFi", Jun. 2015, MobiHoc'15, pp. 267-276 (Year: 2015).*

*Primary Examiner* — Zhiyu Lu

(57) ABSTRACT

Methods, apparatus and systems for wireless sleep monitoring are disclosed. In one embodiment, a described sleep monitoring system comprises: at least one sensor in a venue, wherein the at least one sensor comprises a wireless non-contact sensor having no physical contact with the user; a processor communicatively coupled to the at least one sensor; a memory communicatively coupled to the processor; and a set of instructions stored in the memory. The set of instructions, when executed by the processor, causes the processor to perform: obtaining, based on the at least one sensor, a plurality of time series of sensing features (TSSF) associated with a sleep motion of a user in the venue, and monitoring the sleep motion of the user jointly based on the plurality of TSSF. At least one TSSF of the plurality of TSSF is obtained by: communicating, based on the wireless non-contact sensor, a wireless signal in a wireless multipath channel of the venue, extracting a time series of channel information (TSCI) of the wireless multipath channel of the venue from the wireless signal, and obtaining the at least one TSSF based on the TSCI.

29 Claims, 13 Drawing Sheets

Related U.S. Application Data 17, 2015, application No. 16/945,837, which is a continuation-in-part of application No. 16/127,151, filed on Sep. 10, 2018, which is a continuation-in-part of application No. PCT/US2017/021963, filed on Mar. 10, 2017, application No. 16/945,837, which is a continuation-in-part of application No. 16/125,748, filed on Sep. 9, 2018, which is a continuation-in-part of application No. PCT/US2017/015909, filed on Jan. 31, 2017, application No. 16/945,837, which is a continuation-in-part of application No. 15/861,422, filed on Jan. 3, 2018, and a continuation-in-part of application No. 16/200,608, filed on Nov. 26, 2018, now Pat. No. 10,735,298, which is a continuation-in-part of application No. PCT/US2017/021963, filed on Mar. 10, 2017, application No. 16/945,837, which is a continuation-in-part of application No. 16/446,589, filed on Jun. 19, 2019, now Pat. No. 10,742,475, which is a continuation-in-part of application No. 15/873,806, filed on Jan. 17, 2018, now Pat. No. 10,270,642, which is a continuation-in-part of application No. PCT/US2017/027131, filed on Apr. 12, 2017, application No. 16/945,837, which is a continuation-in-part of application No. 16/667,648, filed on Oct. 29, 2019, and a continuation-in-part of application No. 16/667,757, filed on Oct. 29, 2019, and a continuation-in-part of application No. 16/790,610, filed on Feb. 13, 2020, and a continuation-in-part of application No. 16/790,627, filed on Feb. 13, 2020, and a continuation-in-part of application No. 16/798,337, filed on Feb. 22, 2020, and a continuation-in-part of application No. 16/798,343, filed on Feb. 22, 2020, and a continuation-in-part of application No. 16/870,996, filed on May 10, 2020, and a continuation-in-part of application No. 16/871,000, filed on May 10, 2020, and a continuation-in-part of application No. 16/871,004, filed on May 10, 2020, and a continuation-in-part of application No. 16/871,006, filed on May 10, 2020, and a continuation-in-part of application No. 16/909,913, filed on Jun. 23, 2020, and a continuation-in-part of application No. 16/909,940, filed on Jun. 23, 2020.

(60) Provisional application No. 62/307,081, filed on Mar. 11, 2016, provisional application No. 62/316,850, filed on Apr. 1, 2016, provisional application No. 62/846,686, filed on May 12, 2019, provisional application No. 62/593,826, filed on Dec. 1, 2017, provisional application No. 62/557,117, filed on Sep. 11, 2017, provisional application No. 62/322,575, filed on Apr. 14, 2016, provisional application No. 62/334,110, filed on May 10, 2016, provisional application No. 62/409,796, filed on Oct. 18, 2016, provisional application No. 62/900,565, filed on Sep. 15, 2019, provisional application No. 62/902,357, filed on Sep. 18, 2019, provisional application No. 62/950,093, filed on Dec. 18, 2019, provisional application No. 62/977,326, filed on Feb. 16, 2020, provisional application No. 62/980,206, filed on Feb. 22, 2020, provisional application No. 62/981,387, filed on Feb. 25, 2020, provisional application No. 62/984,737, filed on Mar. 3, 2020, provisional application No. 63/001,226, filed on Mar. 27, 2020, provisional application No. 63/038,037, filed on Jun. 11, 2020.

(56) References Cited

U.S. PATENT DOCUMENTS

| | | | | |
|---|---|---|---|---|
| 11,092,685 | B2* | 8/2021 | Shouldice | G01S 7/415 |
| 2007/0016095 | A1* | 1/2007 | Low | A61B 5/374 |
| | | | | 600/544 |
| 2018/0106897 | A1* | 4/2018 | Shouldice | A61B 5/4812 |
| 2020/0386879 | A1* | 12/2020 | Shouldice | A61B 5/1102 |
| 2022/0075050 | A1* | 3/2022 | Shouldice | G01S 7/415 |

* cited by examiner

METHOD, APPARATUS, AND SYSTEM FOR WIRELESS SLEEP MONITORING

CROSS-REFERENCE TO RELATED APPLICATIONS

The present application is related to U.S. patent application Ser. No. 16/945,827, entitled "METHOD, APPARATUS, AND SYSTEM FOR PROCESSING AND PRESENTING LIFE LOG BASED ON A WIRELESS SIGNAL," filed on Aug. 1, 2020, which is expressly incorporated by reference herein in its entirety.

The present application hereby incorporates by reference the entirety of the disclosures of, and claims priority to, each of the following cases:

(a) U.S. patent application Ser. No. 15/326,112, entitled "WIRELESS POSITIONING SYSTEMS", filed on Jan. 13, 2017,
  (1) which is a national stage entry of PCT patent application PCT % US2015/041037, entitled "WIRELESS POSITIONING SYSTEMS", filed on Jul. 17, 2015, published as WO 2016/011433A2 on Jan. 21, 2016,
(b) U.S. patent application Ser. No. 16/127,151, entitled "METHODS, APPARATUS, SERVERS, AND SYSTEMS FOR VITAL SIGNS DETECTION AND MONITORING", filed on Sep. 10, 2018,
  (1) which is a continuation-in-part of PCT patent application PCT/US2017/021963, entitled "METHODS, APPARATUS, SERVERS, AND SYSTEMS FOR VITAL SIGNS DETECTION AND MONITORING", filed on Mar. 10, 2017, published as WO2017/156492A1 on Sep. 14, 2017,
(c) U.S. patent application Ser. No. 16/125,748, entitled "METHODS, DEVICES, SERVERS, APPARATUS, AND SYSTEMS FOR WIRELESS INTERNET OF THINGS APPLICATIONS", filed on Sep. 9, 2018,
  (1) which is a continuation-in-part of PCT patent application PCT/US2017/015909, entitled "METHODS, DEVICES, SERVERS, APPARATUS, AND SYSTEMS FOR WIRELESS INTERNET OF THINGS APPLICATIONS", filed on Jan. 31, 2017, published as WO2017/155634A1 on Sep. 14, 2017,
(d) U.S. patent application Ser. No. 15/861,422, entitled "METHOD, APPARATUS, SERVER, AND SYSTEMS OF TIME-REVERSAL TECHNOLOGY", filed on Jan. 3, 2018,
(e) U.S. patent application Ser. No. 16/200,608, entitled "METHOD, APPARATUS, SERVER AND SYSTEM FOR VITAL SIGN DETECTION AND MONITORING", filed on Nov. 26, 2018,
  (1) which claims priority to PCT patent application PCT/US2017/021963, entitled "METHODS, APPARATUS, SERVERS, AND SYSTEMS FOR VITAL SIGNS DETECTION AND MONITORING", filed on Mar. 10, 2017, published as WO2017/156492A1 on Sep. 14, 2017,
    a. which claims priority to U.S. Provisional patent application 62/307,081, entitled "TRBREATH: TIME-REVERSAL BREATHING RATE ESTIMATION AND DETECTION", filed on Mar. 11, 2016,
    b. which claims priority to U.S. Provisional patent application 62/316,850, entitled "TRBREATH: TIME-REVERSAL BREATHING RATE ESTIMATION AND DETECTION", filed on Apr. 1, 2016,
(f) U.S. patent application Ser. No. 16/446,589, entitled "METHOD, APPARATUS, AND SYSTEM FOR OBJECT TRACKING AND SENSING USING BROADCASTING", filed on Jun. 19, 2019,
  (1) which claims priority to U.S. Provisional Patent application 62/846,686, entitled "METHOD, APPARATUS, AND SYSTEM FOR WIRELESS INERTIAL MEASUREMENT", filed on May 12, 2019,
  (2) which is a Continuation-in-Part of U.S. patent application Ser. No. 15/873,806, entitled "METHOD, APPARATUS, AND SYSTEM FOR OBJECT TRACKING AND NAVIGATION", filed on Jan. 17, 2018,
    a. which claims priority to U.S. Provisional patent application 62/593,826, entitled "METHOD, APPARATUS, AND SYSTEM FOR OBJECT TRACKING AND NAVIGATION", filed on Dec. 1, 2017,
    b. which claims priority to U.S. Provisional patent application 62/557,117, entitled "METHODS, DEVICES, SERVERS, APPARATUS, AND SYSTEMS FOR WIRELESS INTERNET OF THINGS APPLICATIONS", filed on Sep. 11, 2017,
    c. which claims priority to PCT patent application PCT/US2017/027131, entitled METHODS, APPARATUS, SERVERS, AND SYSTEMS FOR OBJECT TRACKING, filed on Apr. 12, 2017,
      1. which claims priority to U.S. Provisional patent application 62/322,575, entitled "TIME-REVERSAL RESONATING EFFECT AND ITS APPLICATION IN WALKING SPEED ESTIMATION", filed on Apr. 14, 2016,
      2. which claims priority to U.S. Provisional patent application 62/334,110, entitled "TIME-REVERSAL TRACKING WITHOUT MAPPING", filed on May 10, 2016, and
      3. which claims priority to U.S. Provisional patent application 62/409,796, entitled "METHODS, DEVICES, SERVERS, AND SYSTEMS OF TIME REVERSAL BASED TRACKING", filed on Oct. 18, 2016,
(g) U.S. Provisional Patent application 62/900,565, entitled "QUALIFIED WIRELESS SENSING SYSTEM", filed on Sep. 15, 2019,
(h) U.S. Provisional Patent application 62/902,357, entitled "METHOD, APPARATUS, AND SYSTEM FOR AUTOMATIC AND OPTIMIZED DEVICE-TO-CLOUD CONNECTION FOR WIRELESS SENSING", filed on Sep. 18, 2019,
(i) U.S. patent application Ser. No. 16/667,648, entitled "METHOD, APPARATUS, AND SYSTEM FOR WIRELESS PROXIMITY AND PRESENCE MONITORING", filed on Oct. 29, 2019,
(j) U.S. patent application Ser. No. 16/667,757, entitled "METHOD, APPARATUS, AND SYSTEM FOR HUMAN IDENTIFICATION BASED ON HUMAN RADIO BIOMETRIC INFORMATION", filed on Oct. 29, 2019,
(k) U.S. Provisional Patent application 62/950,093, entitled "METHOD, APPARATUS, AND SYSTEM FOR TARGET POSITIONING", filed on Dec. 18, 2019,
(l) U.S. patent application Ser. No. 16/790,610, entitled "METHOD, APPARATUS, AND SYSTEM FOR WIRELESS GAIT RECOGNITION", filed Feb. 13, 2020, (m) U.S. patent application Ser. No. 16/790,627, entitled "METHOD, APPARATUS, AND SYSTEM FOR OUTDOOR TARGET TRACKING", filed Feb. 13, 2020.
(n) U.S. Provisional Patent application 62/977,326, entitled "METHOD, APPARATUS, AND SYSTEM FOR AUTOMATIC AND ADAPTIVE WIRELESS MONITORING AND TRACKING", filed on Feb. 16, 2020,
(o) U.S. patent application Ser. No. 16/798,337, entitled "METHOD, APPARATUS, AND SYSTEM FOR WIRELESS OBJECT SCANNING", filed Feb. 22, 2020,
(p) U.S. patent application Ser. No. 16/798,343, entitled "METHOD, APPARATUS, AND SYSTEM FOR WIRELESS OBJECT TRACKING", filed Feb. 22, 2020,
(q) U.S. Provisional Patent application 62/980,206, entitled "METHOD, APPARATUS, AND SYSTEM FOR WIRELESS SENSING", filed on Feb. 22, 2020,
(r) U.S. Provisional Patent application 62/981,387, entitled "METHOD, APPARATUS, AND SYSTEM FOR VEHICLE WIRELESS MONITORING", filed on Feb. 25, 2020,
(s) U.S. Provisional Patent application 62/984,737, entitled "METHOD, APPARATUS, AND SYSTEM FOR IMPROVED WIRELESS MONITORING", filed on Mar. 3, 2020,
(t) U.S. Provisional Patent application 63/001,226, entitled "METHOD, APPARATUS, AND SYSTEM FOR IMPROVED WIRELESS MONITORING AND USER INTERFACE", filed on Mar. 27, 2020,
(u) U.S. patent application Ser. No. 16/870,996, entitled "METHOD, APPARATUS, AND SYSTEM FOR WIRELESS INERTIAL MEASUREMENT", filed on May 10, 2020,
(v) U.S. patent application Ser. No. 16/871,000, entitled "METHOD, APPARATUS, AND SYSTEM FOR WIRELESS TRACKING WITH GRAPH-BASED PARTICLE FILTERING", filed on May 10, 2020,
(w) U.S. patent application Ser. No. 16/871,004, entitled "METHOD, APPARATUS, AND SYSTEM FOR PEOPLE COUNTING AND RECOGNITION BASED ON RHYTHMIC MOTION MONITORING", filed on May 10, 2020,
(x) U.S. patent application Ser. No. 16/871,006, entitled "METHOD, APPARATUS, AND SYSTEM FOR VITAL SIGNS MONITORING USING HIGH FREQUENCY WIRELESS SIGNALS", filed on May 10, 2020,
(y) U.S. Provisional Patent application 63/038,037, entitled "METHOD, APPARATUS, AND SYSTEM FOR MOTION LOCALIZATION, WALKING DETECTION AND DEVICE QUALIFICATION", filed on Jun. 11, 2020,
(z) U.S. patent application Ser. No. 16/909,913, entitled "METHOD, APPARATUS, AND SYSTEM FOR IMPROVING TOPOLOGY OF WIRELESS SENSING SYSTEMS", filed on Jun. 23, 2020,
(aa) U.S. patent application Ser. No. 16/909,940, entitled "METHOD, APPARATUS, AND SYSTEM FOR QUALIFIED WIRELESS SENSING", filed on Jun. 23, 2020.

TECHNICAL FIELD

The present teaching generally relates to object sleep monitoring. More specifically, the present teaching relates to monitoring sleep quantity and quality of an object based on wireless channel information in a rich-scattering environment.

BACKGROUND

Sleep plays a vital role in an individual's health and well-being, both mentally and physically. It is well recognized that sleep quantity and quality is fundamentally related to health risks like cardiovascular decease, stroke, kidney failure, diabetes, and adverse mental conditions, etc. Unfortunately, in modern society, a number of people suffer from sleep disorders. As recently reported, 10% of the population suffers from chronic insomnia (which is even higher among elders), and ⅓ of Americans do not get sufficient sleep. Monitoring sleep emerges as an essential demand to help, manage, diagnose, and treat the growing group of sleep disorders as well as to keep regular tabs on personal health.

Sleep monitoring, however, is a challenging task that has drawn tremendous efforts for decades. Generally, it measures sleep time, recognizes different sleep stages, e.g., wake, REM (Rapid Eye Movement) and NREM (Non-REM), and accordingly assesses an individual's sleep quality. Various solutions have been proposed. The medical gold standard relies on Polysomnography (PSG), which monitors various physiological parameters such as brain activities, respirations, and body movements by a number of wired sensors attached to the patient Albeit accurate and comprehensive, PSG is usually expensive and cumbersome with the invasive sensors that may cause sleep difficulties, limiting itself to clinical usage for confirmed patients. Other approaches including photoplethysmography (PPG) and actigraphy (ACT) require users to wear dedicated sensors during sleep. Ballistocardiogram (BCG) needs to instrument the mattress with an array of EMFi sensors to measure ballistic force. Despite of the costs, these approaches provide suitable solutions for those who need special cares but are less-than-ideal for the public. Recent efforts in mobile computing envision in-home sleep monitoring using smartphones and wearables. These methods, however, only provide coarse-grained, less accurate measurements and fail to monitor vital signs like respiratory rate. In addition, mobiles and wearables are undesirable for especially elders and those with dementia.

SUMMARY

The present teaching generally relates to object sleep monitoring. More specifically, the present teaching relates to monitoring sleep quantity and quality of an object based on wireless channel information in a rich-scattering environment.

In one embodiment, a system for monitoring a sleep motion of a user in a venue is described. The system comprises: at least one sensor in the venue, wherein the at least one sensor comprises a wireless non-contact sensor having no physical contact with the user; a processor communicatively coupled to the at least one sensor; a memory communicatively coupled to the processor; and a set of instructions stored in the memory. The set of instructions, when executed by the processor, causes the processor to perform: obtaining, based on the at least one sensor, a plurality of time series of sensing features (TSSF) associated with the sleep motion of the user in the venue, and monitoring the sleep motion of the user jointly based on the plurality of TSSF. At least one TSSF of the plurality of TSSF is obtained by: communicating, based on the wireless non-contact sensor, a wireless signal in a wireless multipath channel of the venue, extracting a time series of channel information (TSCI) of the wireless multipath channel of the venue from the wireless signal, and obtaining the at least one TSSF based on the TSCI.

In another embodiment, a system for monitoring a sleep motion of a user in a venue is described. The system comprises: at least one sensor in the venue, wherein the at least one sensor comprises a non-contact sensor having no physical contact with the user; a processor communicatively coupled to the at least one sensor; a memory communicatively coupled to the processor; and a set of instructions stored in the memory. The set of instructions, when executed by the processor, causes the processor to perform: obtaining, based on the at least one sensor, a plurality of time series of sensing features (TSSF) associated with the sleep motion of the user in the venue, and monitoring the sleep motion of the user jointly based on the plurality of TSSF. The plurality of TSSF comprises a first TSSF and a second TSSF. The first TSSF comprises motion features associated with an intensity of the sleep motion of the user. The second TSSF comprises periodicity features associated with a periodicity of the sleep motion of the user. Both the first TSSF and the second TSSF are obtained based on the non-contact sensor.

In yet another embodiment, a method of a sleep monitoring system is described. The method comprises: obtaining, based on at least one sensor in a venue, a plurality of time series of sensing features (TSSF) associated with a sleep motion of a user in the venue, wherein: the plurality of TSSF comprises a first TSSF and a second TSSF, the first TSSF comprises motion features associated with an intensity of the sleep motion of the user, the second TSSF comprises periodicity features associated with a periodicity of the sleep motion of the user; communicating, based on a non-contact sensor having no physical contact with the user, a wireless signal in a wireless multipath channel of the venue; extracting a time series of channel information (TSCI) of the wireless multipath channel of the venue from the wireless signal; obtaining, based on the TSCI, at least one of the first TSSF or the second TSSF; and monitoring the sleep motion of the user jointly based on the plurality of TSSF.

In a different embodiment, a server device of a sleep monitoring system is described. The server device comprises: a processor communicatively coupled to at least one sensor in a venue; a memory communicatively coupled to the processor; and a set of instructions stored in the memory. The set of instructions, when executed by the processor, causes the processor to perform: obtaining a plurality of time series of sensing features (TSSF) associated with a sleep motion of a user in the venue, and monitoring the sleep motion of the user jointly based on the plurality of TSSF. Each of the plurality of TSSF is associated with a respective sensor of the at least one sensor. The plurality of TSSF comprises a first TSSF and a second TSSF. The first TSSF comprises motion features associated with an intensity of the sleep motion of the user. The second TSSF comprises periodicity features associated with a periodicity of the sleep motion of the user. At least one of the first TSSF or the second TSSF is obtained based on a time series of channel information (TSCI) of a wireless multipath channel of the venue. The TSCI is extracted from a wireless signal communicated in the wireless multipath channel of the venue by one of the at least one sensor in the venue.

Other concepts relate to software for implementing the present teaching on wireless sleep monitoring in a rich-scattering environment. Additional novel features will be set forth in part in the description which follows, and in part will become apparent to those skilled in the art upon examination of the following and the accompanying drawings or may be learned by production or operation of the examples. The novel features of the present teachings may be realized and attained by practice or use of various aspects of the methodologies, instrumentalities and combinations set forth in the detailed examples discussed below.

BRIEF DESCRIPTION OF DRAWINGS

The methods, systems, and/or devices described herein are further described in terms of exemplary embodiments. These exemplary embodiments are described in detail with reference to the drawings. These embodiments are non-limiting exemplary embodiments, in which like reference numerals represent similar structures throughout the several views of the drawings.

DETAILED DESCRIPTION

Figure 1:
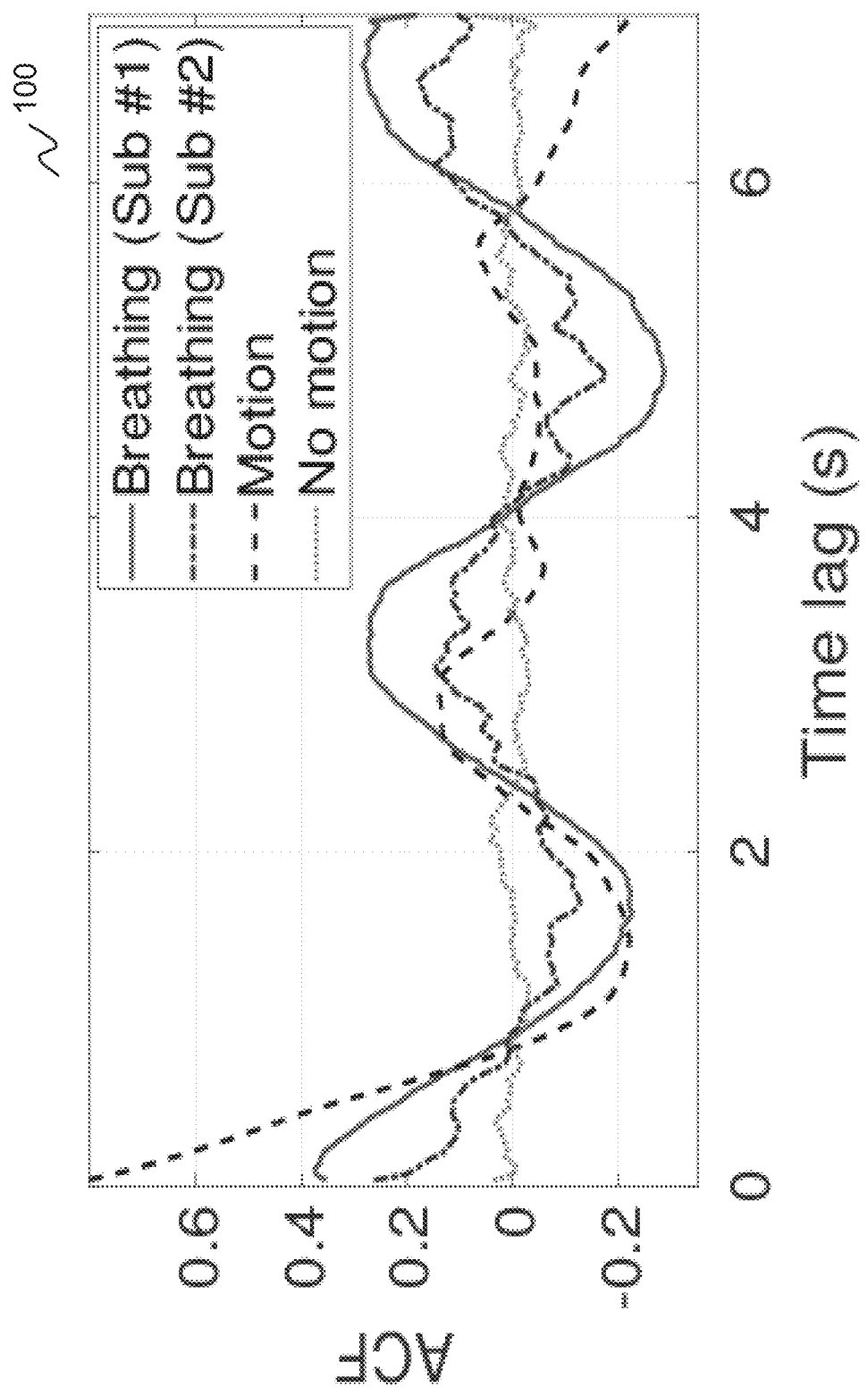
FIG. 1 illustrates exemplary autocorrelation functions of the received signals under different scenarios, according to one embodiment of the present teaching.

In the following detailed description, numerous specific details are set forth by way of examples in order to provide a thorough understanding of the relevant teachings. However, it should be apparent to those skilled in the art that the present teachings may be practiced without such details. In other instances, well known methods, procedures, components, and/or circuitry have been described at a relatively high-level, without detail, in order to avoid unnecessarily obscuring aspects of the present teachings.

In one embodiment, the present teaching discloses a method, apparatus, device, system, and/or software (method/apparatus/device/system/software) of a wireless monitoring system. A time series of channel information (CI) of a wireless multipath channel (channel) may be obtained (e.g. dynamically) using a processor, a memory communicatively coupled with the processor and a set of instructions stored in the memory. The time series of CI (TSCI) may be extracted from a wireless signal (signal) transmitted between a Type 1 heterogeneous wireless device (e.g. wireless transmitter, TX) and a Type 2 heterogeneous wireless device (e.g. wireless receiver, RX) in a venue through the channel. The channel may be impacted by an expression (e.g. motion, movement, expression, and/or change in position/pose/shape/expression) of an object in the venue. A characteristics and/or a spatial-temporal information (STI, e.g. motion information) of the object and/or of the motion of the object may be monitored based on the TSCI. A task may be performed based on the characteristics and/or STI. A presentation associated with the task may be generated in a user-interface (UI) on a device of a user. The TSCI may be a wireless signal stream. The TSCI or each CI may be preprocessed. A device may be a station (STA). The symbol "A/B" means "A and/or B" in the present teaching.

The expression may comprise placement, placement of moveable parts, location, position, orientation, identifiable place, region, spatial coordinate, presentation, state, static expression, size, length, width, height, angle, scale, shape, curve, surface, area, volume, pose, posture, manifestation, body language, dynamic expression, motion, motion sequence, gesture, extension, contraction, distortion, deformation, body expression (e.g. head, face, eye, mouth, tongue, hair, voice, neck, limbs, arm, hand, leg, foot, muscle, moveable parts), surface expression (e.g. shape, texture, material, color, electromagnetic (EM) characteristics, visual pattern, wetness, reflectance, translucency, flexibility), material property (e.g. living tissue, hair, fabric, metal, wood, leather, plastic, artificial material, solid, liquid, gas, temperature), movement, activity, behavior, change of expression, and/or some combination.

The wireless signal may comprise: transmitted/received signal, EM radiation, RF signal/transmission, signal in licensed/unlicensed/ISM band, bandlimited signal, baseband signal, wireless/mobile/cellular communication signal, wireless/mobile/cellular network signal, mesh signal, light signal/communication, downlink/uplink signal, unicast/multicast/broadcast signal, standard (e.g. WLAN, WWAN, WPAN, WBAN, international, national, industry, defacto, IEEE, IEEE 802, 802.11/15/16, WiFi, 802.11n/ac/ax/be, 3G/4G/LTE/5G/6G/7G/8G, 3GPP, Bluetooth, BLE, Zigbee, RFID, UWB, WiMax) compliant signal, protocol signal, standard frame, beacon/pilot/probe/enquiry/acknowledgement/handshake/synchronization signal, management/control/data frame, management/control/data signal, standardized wireless/cellular communication protocol, reference signal, source signal, motion probe/detection/sensing signal, and/or series of signals. The wireless signal may comprise a line-of-sight (LOS), and/or a non-LOS component (or path/link). Each CI may be extracted/generated/computed/sensed at a layer (e.g. PHY/MAC layer in OSI model) of Type 2 device and may be obtained by an application (e.g. software, firmware, driver, app, wireless monitoring software/system).

The wireless multipath channel may comprise: a communication channel, analog frequency channel (e.g. with analog carrier frequency near 700/800/900 MHz, 1.8/1.8/2.4/3/5/6/27/60 GHz), coded channel (e.g. in CDMA), and/or channel of a wireless network/system (e.g. WLAN, WiFi, mesh, LTE, 4G/5G, Bluetooth, Zigbee, UWB, RFID, microwave). It may comprise more than one channel. The channels may be consecutive (e.g. with adjacent/overlapping bands) or non-consecutive channels (e.g. non-overlapping WiFi channels, one at 2.4 GHz and one at 5 GHz).

The TSCI may be extracted from the wireless signal at a layer of the Type 2 device (e.g. a layer of OSI reference model, physical layer, data link layer, logical link control layer, media access control (MAC) layer, network layer, transport layer, session layer, presentation layer, application layer, TCP/IP layer, internet layer, link layer). The TSCI may be extracted from a derived signal (e.g. baseband signal, motion detection signal, motion sensing signal) derived from the wireless signal (e.g. RF signal). It may be (wireless) measurements sensed by the communication protocol (e.g. standardized protocol) using existing mechanism (e.g. wireless/cellular communication standard/network, 3G/LTE/4G/5G/6G/7G/8G, WiFi, IEEE 802.11/15/16). The derived signal may comprise a packet with at least one of: a preamble, a header and a payload (e.g. for data/control/management in wireless links/networks). The TSCI may be extracted from a probe signal (e.g. training sequence, STF, LTF, L-STF, L-LTF, L-SIG, HE-STF, HE-LTF, HE-SIG-A, HE-SIG-B, CEF) in the packet. A motion detection/sensing signal may be recognized/identified base on the probe signal. The packet may be a standard-compliant protocol frame, management frame, control frame, data frame, sounding frame, excitation frame, illumination frame, null data frame, beacon frame, pilot frame, probe frame, request frame, response frame, association frame, reassociation frame, disassociation frame, authentication frame, action frame, report frame, poll frame, announcement frame, extension frame, enquiry frame, acknowledgement frame, RTS frame, CTS frame, QoS frame, CF-Poll frame, CF-Ack frame, block acknowledgement frame, reference frame, training frame, and/or synchronization frame.

The packet may comprise a control data and/or a motion detection probe. A data (e.g. ID/parameters/characteristics/settings/control signal/command/instruction/notification/broadcasting-related information of the Type 1 device) may be obtained from the payload. The wireless signal may be transmitted by the Type 1 device. It may be received by the Type 2 device. A database (e.g. in local server, hub device, cloud server, storage network) may be used to store the TSCI, characteristics, STI, signatures, patterns, behaviors, trends, parameters, analytics, output responses, identification information, user information, device information, channel information, venue (e.g. map, environmental model, network, proximity devices/networks) information, task information, class/category information, presentation (e.g. UI) information, and/or other information.

The Type 1/Type 2 device may comprise at least one of: electronics, circuitry, transmitter (TX)/receiver (RX)/transceiver, RF interface, "Origin Satellite"/"Tracker Bot", unicast/multicast/broadcasting device, wireless source device, source/destination device, wireless node, hub device, target device, motion detection device, sensor device, remote/wireless sensor device, wireless communication device, wireless-enabled device, standard compliant device, and/or receiver. The Type 1 (or Type 2) device may be heterogeneous because, when there are more than one instances of Type 1 (or Type 2) device, they may have different circuitry, enclosure, structure, purpose, auxiliary functionality, chip/IC, processor, memory, software, firmware, network connectivity, antenna, brand, model, appearance, form, shape, color, material, and/or specification. The Type 1/Type 2 device may comprise: access point, router, mesh router, internet-of-things (IoT) device, wireless terminal, one or more radio/RF subsystem/wireless interface (e.g. 2.4 GHz radio, 5 GHz radio, front haul radio, backhaul radio), modem, RF front end, RF/radio chip or integrated circuit (IC).

At least one of: Type 1 device, Type 2 device, a link between them, the object, the characteristics, the STI, the monitoring of the motion, and the task may be associated with an identification (ID) such as UUID. The Type 1/Type 2/another device may obtain/store/retrieve/access/preprocess/condition/process/analyze/monitor/apply the TSCI. The Type 1 and Type 2 devices may communicate network traffic in another channel (e.g. Ethernet, HDMI, USB, Bluetooth, BLE, WiFi, LTE, other network, the wireless multipath channel) in parallel to the wireless signal. The Type 2 device may passively observe/monitor/receive the wireless signal from the Type 1 device in the wireless multipath channel without establishing connection (e.g. association/authentication) with, or requesting service from, the Type 1 device.

The transmitter (i.e. Type 1 device) may function as (play role of) receiver (i.e. Type 2 device) temporarily, sporadically, continuously, repeatedly, interchangeably, alternately, simultaneously, concurrently, and/or contemporaneously; and vice versa. A device may function as Type 1 device (transmitter) and/or Type 2 device (receiver) temporarily, sporadically, continuously, repeatedly, simultaneously, concurrently, and/or contemporaneously. There may be multiple wireless nodes each being Type 1 (TX) and/or Type 2 (RX) device. A TSCI may be obtained between every two nodes when they exchange/communicate wireless signals. The characteristics and/or STI of the object may be monitored individually based on a TSCI, or jointly based on two or more (e.g. all) TSCI. The motion of the object may be monitored actively (in that Type 1 device, Type 2 device, or both, are wearable of/associated with the object) and/or passively (in that both Type 1 and Type 2 devices are not wearable of/associated with the object). It may be passive because the object may not be associated with the Type 1 device and/or the Type 2 device. The object (e.g. user, an automated guided vehicle or AGV) may not need to carry/install any wearables/fixtures (i.e. the Type 1 device and the Type 2 device are not wearable/attached devices that the object needs to carry in order perform the task). It may be active because the object may be associated with either the Type 1 device and/or the Type 2 device. The object may carry (or installed) a wearable/a fixture (e.g. the Type 1 device, the Type 2 device, a device communicatively coupled with either the Type 1 device or the Type 2 device).

The presentation may be visual, audio, image, video, animation, graphical presentation, text, etc. A computation of the task may be performed by a processor (or logic unit) of the Type 1 device, a processor (or logic unit) of an IC of the Type 1 device, a processor (or logic unit) of the Type 2 device, a processor of an IC of the Type 2 device, a local server, a cloud server, a data analysis subsystem, a signal analysis subsystem, and/or another processor. The task may be performed with/without reference to a wireless fingerprint or a baseline (e.g. collected, processed, computed, transmitted and/or stored in a training phase/survey/current survey/previous survey/recent survey/initial wireless survey, a passive fingerprint), a training, a profile, a trained profile, a static profile, a survey, an initial wireless survey, an initial setup, an installation, a retraining, an updating and a reset.

The Type 1 device (TX device) may comprise at least one heterogeneous wireless transmitter. The Type 2 device (RX device) may comprise at least one heterogeneous wireless receiver. The Type 1 device and the Type 2 device may be collocated. The Type 1 device and the Type 2 device may be the same device. Any device may have a data processing unit/apparatus, a computing unit/system, a network unit/system, a processor (e.g. logic unit), a memory communicatively coupled with the processor, and a set of instructions stored in the memory to be executed by the processor. Some processors, memories and sets of instructions may be coordinated. There may be multiple Type 1 devices interacting (e.g. communicating, exchange signal/control/notification/other data) with the same Type 2 device (or multiple Type 2 devices), and/or there may be multiple Type 2 devices interacting with the same Type 1 device. The multiple Type 1 devices/Type 2 devices may be synchronized and/or asynchronous, with same/different window width/size and/or time shift, same/different synchronized start time, synchronized end time, etc. Wireless signals sent by the multiple Type 1 devices may be sporadic, temporary, continuous, repeated, synchronous, simultaneous, concurrent, and/or contemporaneous. The multiple Type 1 devices/Type 2 devices may operate independently and/or collaboratively. A Type 1 and/or Type 2 device may have/comprise/be heterogeneous hardware circuitry (e.g. a heterogeneous chip or a heterogeneous IC capable of generating/receiving the wireless signal, extracting CI from received signal, or making the CI available). They may be communicatively coupled to same or different servers (e.g. cloud server, edge server, local server, hub device).

Operation of one device may be based on operation, state, internal state, storage, processor, memory output, physical location, computing resources, network of another device. Difference devices may communicate directly, and/or via another device/server/hub device/cloud server. The devices may be associated with one or more users, with associated settings. The settings may be chosen once, pre-programmed, and/or changed (e.g. adjusted, varied, modified)/varied over time. There may be additional steps in the method. The steps and/or the additional steps of the method may be performed in the order shown or in another order. Any steps may be performed in parallel, iterated, or otherwise repeated or performed in another manner. A user may be human, adult, older adult, man, woman, juvenile, child, baby, pet, animal, creature, machine, computer module/software, etc.

In the case of one or multiple Type 1 devices interacting with one or multiple Type 2 devices, any processing (e.g. time domain, frequency domain) may be different for different devices. The processing may be based on locations, orientation, direction, roles, user-related characteristics, settings, configurations, available resources, available bandwidth, network connection, hardware, software, processor, co-processor, memory, battery life, available power, antennas, antenna types, directional/unidirectional characteristics of the antenna, power setting, and/or other parameters/characteristics of the devices.

The wireless receiver (e.g. Type 2 device) may receive the signal and/or another signal from the wireless transmitter (e.g. Type 1 device). The wireless receiver may receive another signal from another wireless transmitter (e.g. a second Type 1 device). The wireless transmitter may transmit the signal and/or another signal to another wireless receiver (e.g. a second Type 2 device). The wireless transmitter, wireless receiver, another wireless receiver and/or another wireless transmitter may be moving with the object and/or another object. The another object may be tracked.

The Type 1 and/or Type 2 device may be capable of wirelessly coupling with at least two Type 2 and/or Type 1 devices. The Type 1 device may be caused/controlled to switch/establish wireless coupling (e.g. association, authentication) from the Type 2 device to a second Type 2 device at another location in the venue. Similarly, the Type 2 device may be caused/controlled to switch/establish wireless coupling from the Type 1 device to a second Type 1 device at yet another location in the venue. The switching may be controlled by a server (or a hub device), the processor, the Type 1 device, the Type 2 device, and/or another device. The radio used before and after switching may be different. A second wireless signal (second signal) may be caused to be transmitted between the Type 1 device and the second Type 2 device (or between the Type 2 device and the second Type 1 device) through the channel. A second TSCI of the channel extracted from the second signal may be obtained. The second signal may be the first signal. The characteristics, STI and/or another quantity of the object may be monitored based on the second TSCI. The Type 1 device and the Type 2 device may be the same. The characteristics, STI and/or another quantity with different time stamps may form a waveform. The waveform may be displayed in the presentation.

The wireless signal and/or another signal may have data embedded. The wireless signal may be a series of probe signals (e.g. a repeated transmission of probe signals, a re-use of one or more probe signals). The probe signals may change/vary over time. A probe signal may be a standard compliant signal, protocol signal, standardized wireless protocol signal, control signal, data signal, wireless communication network signal, cellular network signal, WiFi signal, LTE/5G/6G/7G signal, reference signal, beacon signal, motion detection signal, and/or motion sensing signal. A probe signal may be formatted according to a wireless network standard (e.g. WiFi), a cellular network standard (e.g. LTE/5G/6G), or another standard. A probe signal may comprise a packet with a header and a payload. A probe signal may have data embedded. The payload may comprise data. A probe signal may be replaced by a data signal. The probe signal may be embedded in a data signal. The wireless receiver, wireless transmitter, another wireless receiver and/or another wireless transmitter may be associated with at least one processor, memory communicatively coupled with respective processor, and/or respective set of instructions stored in the memory which when executed cause the processor to perform any and/or all steps needed to determine the STI (e.g. motion information), initial ST, initial time, direction, instantaneous location, instantaneous angle, and/or speed, of the object. The processor, the memory and/or the set of instructions may be associated with the Type 1 device, one of the at least one Type 2 device, the object, a device associated with the object, another device associated with the venue, a cloud server, a hub device, and/or another server.

The Type 1 device may transmit the signal in a broadcasting manner to at least one Type 2 device(s) through the channel in the venue. The signal is transmitted without the Type 1 device establishing wireless connection (e.g. association, authentication) with any Type 2 device, and without any Type 2 device requesting services from the Type 1 device. The Type 1 device may transmit to a particular media access control (MAC) address common for more than one Type 2 devices. Each Type 2 device may adjust its MAC address to the particular MAC address. The particular MAC address may be associated with the venue. The association may be recorded in an association table of an Association Server (e.g. hub device). The venue may be identified by the Type 1 device, a Type 2 device and/or another device based on the particular MAC address, the series of probe signals, and/or the at least one TSCI extracted from the probe signals. For example, a Type 2 device may be moved to a new location in the venue (e.g. from another venue). The Type 1 device may be newly set up in the venue such that the Type 1 and Type 2 devices are not aware of each other. During set up, the Type 1 device may be instructed/guided/caused/controlled (e.g. using dummy receiver, using hardware pin setting/connection, using stored setting, using local setting, using remote setting, using downloaded setting, using hub device, or using server) to send the series of probe signals to the particular MAC address. Upon power up, the Type 2 device may scan for probe signals according to a table of MAC addresses (e.g. stored in a designated source, server, hub device, cloud server) that may be used for broadcasting at different locations (e.g. different MAC address used for different venue such as house, office, enclosure, floor, multi-storey building, store, airport, mall, stadium, hall, station, subway, lot, area, zone, region, district, city, country, continent). When the Type 2 device detects the probe signals sent to the particular MAC address, the Type 2 device can use the table to identify the venue based on the MAC address. A location of a Type 2 device in the venue may be computed based on the particular MAC address, the series of probe signals, and/or the at least one TSCI obtained by the Type 2 device from the probe signals. The computing may be performed by the Type 2 device. The particular MAC address may be changed (e.g. adjusted, varied, modified) over time. It may be changed according to a time table, rule, policy, mode, condition, situation and/or change. The particular MAC address may be selected based on availability of the MAC address, a pre-selected list, collision pattern, traffic pattern, data traffic between the Type 1 device and another device, effective bandwidth, random selection, and/or a MAC address switching plan. The particular MAC address may be the MAC address of a second wireless device (e.g. a dummy receiver, or a receiver that serves as a dummy receiver).

The Type 1 device may transmit the probe signals in a channel selected from a set of channels. At least one CI of the selected channel may be obtained by a respective Type 2 device from the probe signal transmitted in the selected channel. The selected channel may be changed (e.g. adjusted, varied, modified) over time. The change may be according to a time table, rule, policy, mode, condition, situation, and/or change. The selected channel may be selected based on availability of channels, random selection, a pre-selected list, co-channel interference, inter-channel interference, channel traffic pattern, data traffic between the Type 1 device and another device, effective bandwidth associated with channels, security criterion, channel switching plan, a criterion, a quality criterion, a signal quality condition, and/or consideration.

The particular MAC address and/or an information of the selected channel may be communicated between the Type 1 device and a server (e.g. hub device) through a network. The particular MAC address and/or the information of the selected channel may also be communicated between a Type 2 device and a server (e.g. hub device) through another network. The Type 2 device may communicate the particular MAC address and/or the information of the selected channel to another Type 2 device (e.g. via mesh network, Bluetooth, WiFi, NFC, ZigBee, etc.). The particular MAC address and/or selected channel may be chosen by a server (e.g. hub device). The particular MAC address and/or selected channel may be signaled in an announcement channel by the Type 1 device, the Type 2 device and/or a server (e.g. hub device). Before being communicated, any information may be pre-processed.

Wireless connection (e.g. association, authentication) between the Type 1 device and another wireless device may be established (e.g. using a signal handshake). The Type 1 device may send a first handshake signal (e.g. sounding frame, probe signal, request-to-send RTS) to the another device. The another device may reply by sending a second handshake signal (e.g. a command, or a clear-to-send CTS) to the Type 1 device, triggering the Type 1 device to transmit the signal (e.g. series of probe signals) in the broadcasting manner to multiple Type 2 devices without establishing connection with any Type 2 device. The second handshake signals may be a response or an acknowledge (e.g. ACK) to the first handshake signal. The second handshake signal may contain a data with information of the venue, and/or the Type 1 device. The another device may be a dummy device with a purpose (e.g. primary purpose, secondary purpose) to establish the wireless connection with the Type 1 device, to receive the first signal, and/or to send the second signal. The another device may be physically attached to the Type 1 device.

In another example, the another device may send a third handshake signal to the Type 1 device triggering the Type 1 device to broadcast the signal (e.g. series of probe signals) to multiple Type 2 devices without establishing connection (e.g. association, authentication) with any Type 2 device. The Type 1 device may reply to the third special signal by transmitting a fourth handshake signal to the another device. The another device may be used to trigger more than one Type 1 devices to broadcast. The triggering may be sequential, partially sequential, partially parallel, or fully parallel. The another device may have more than one wireless circuitries to trigger multiple transmitters in parallel. Parallel trigger may also be achieved using at least one yet another device to perform the triggering (similar to what as the another device does) in parallel to the another device. The another device may not communicate (or suspend communication) with the Type 1 device after establishing connection with the Type 1 device. Suspended communication may be resumed. The another device may enter an inactive mode, hibernation mode, sleep mode, stand-by mode, low-power mode, OFF mode and/or power-down mode, after establishing the connection with the Type 1 device. The another device may have the particular MAC address so that the Type 1 device sends the signal to the particular MAC address. The Type 1 device and/or the another device may be controlled and/or coordinated by a first processor associated with the Type 1 device, a second processor associated with the another device, a third processor associated with a designated source and/or a fourth processor associated with another device. The first and second processors may coordinate with each other.

A first series of probe signals may be transmitted by a first antenna of the Type 1 device to at least one first Type 2 device through a first channel in a first venue. A second series of probe signals may be transmitted by a second antenna of the Type 1 device to at least one second Type 2 device through a second channel in a second venue. The first series and the second series may/may not be different. The at least one first Type 2 device may/may not be different from the at least one second Type 2 device. The first and/or second series of probe signals may be broadcasted without connection (e.g. association, authentication) established between the Type 1 device and any Type 2 device. The first and second antennas may be same/different. The two venues may have different sizes, shape, multipath characteristics. The first and second venues may overlap. The respective immediate areas around the first and second antennas may overlap. The first and second channels may be same/different. For example, the first one may be WiFi while the second may be LTE. Or, both may be WiFi, but the first one may be 2.4 GHz WiFi and the second may be 5 GHz WiFi. Or, both may be 2.4 GHz WiFi, but have different channel numbers, SSID names, and/or WiFi settings.

Each Type 2 device may obtain at least one TSCI from the respective series of probe signals, the CI being of the respective channel between the Type 2 device and the Type 1 device. Some first Type 2 device(s) and some second Type 2 device(s) may be the same. The first and second series of probe signals may be synchronous/asynchronous. A probe signal may be transmitted with data or replaced by a data signal. The first and second antennas may be the same. The first series of probe signals may be transmitted at a first rate (e.g. 30 Hz). The second series of probe signals may be transmitted at a second rate (e.g. 200 Hz). The first and second rates may be same/different. The first and/or second rate may be changed (e.g. adjusted, varied, modified) over time. The change may be according to a time table, rule, policy, mode, condition, situation, and/or change. Any rate may be changed (e.g. adjusted, varied, modified) over time. The first and/or second series of probe signals may be transmitted to a first MAC address and/or second MAC address respectively. The two MAC addresses may be same/different. The first series of probe signals may be transmitted in a first channel. The second series of probe signals may be transmitted in a second channel. The two channels may be same/different. The first or second MAC address, first or second channel may be changed over time. Any change may be according to a time table, rule, policy, mode, condition, situation, and/or change.

The Type 1 device and another device may be controlled and/or coordinated, physically attached, or may be of/in/of a common device. They may be controlled by/connected to a common data processor, or may be connected to a common bus interconnect/network/LAN/Bluetooth network/NFC network/BLE network wired network/wireless network mesh network/mobile network cloud. They may share a common memory, or be associated with a common user, user device, profile, account, identity (ID), identifier, household, house, physical address, location, geographic coordinate, IP subnet, SSID, home device, office device, and/or manufacturing device. Each Type 1 device may be a signal source of a set of respective Type 2 devices (i.e. it sends a respective signal (e.g. respective series of probe signals) to the set of respective Type 2 devices). Each respective Type 2 device chooses the Type 1 device from among all Type 1 devices as its signal source. Each Type 2 device may choose asynchronously. At least one TSCI may be obtained by each respective Type 2 device from the respective series of probe signals from the Type 1 device, the CI being of the channel between the Type 2 device and the Type 1 device. The respective Type 2 device chooses the Type 1 device from among all Type 1 devices as its signal source based on identity (ID) or identifier of Type 1/Type 2 device, task to be performed, past signal source, history (e.g. of past signal source, Type 1 device, another Type 1 device, respective Type 2 receiver, and/or another Type 2 receiver), threshold for switching signal source, and/or information of a user, account, access info, parameter, characteristics, and/or signal strength (e.g. associated with the Type 1 device and/or the respective Type 2 receiver). Initially, the Type 1 device may be signal source of a set of initial respective Type 2 devices (i.e. the Type 1 device sends a respective signal (series of probe signals) to the set of initial respective Type 2 devices) at an initial time.

Each initial respective Type 2 device chooses the Type 1 device from among all Type 1 devices as its signal source.

The signal source (Type 1 device) of a particular Type 2 device may be changed (e.g. adjusted, varied, modified) when (1) time interval between two adjacent probe signals (e.g. between current probe signal and immediate past probe signal, or between next probe signal and current probe signal) received from current signal source of the Type 2 device exceeds a first threshold; (2) signal strength associated with current signal source of the Type 2 device is below a second threshold; (3) a processed signal strength associated with current signal source of the Type 2 device is below a third threshold, the signal strength processed with low pass filter, band pass filter, median filter, moving average filter, weighted averaging filter, linear filter and/or non-linear filter; and/or (4) signal strength (or processed signal strength) associated with current signal source of the Type 2 device is below a fourth threshold for a significant percentage of a recent time window (e.g. 70%, 80%, 90%). The percentage may exceed a fifth threshold. The first, second, third, fourth and/or fifth thresholds may be time varying.

Condition (1) may occur when the Type 1 device and the Type 2 device become progressively far away from each other, such that some probe signal from the Type 1 device becomes too weak and is not received by the Type 2 device. Conditions (2)-(4) may occur when the two devices become far from each other such that the signal strength becomes very weak.

The signal source of the Type 2 device may not change if other Type 1 devices have signal strength weaker than a factor (e.g. 1, 1.1, 1.2, or 1.5) of the current signal source. If the signal source is changed (e.g. adjusted, varied, modified), the new signal source may take effect at a near future time (e.g. the respective next time). The new signal source may be the Type 1 device with strongest signal strength, and/or processed signal strength. The current and new signal source may be same/different.

A list of available Type 1 devices may be initialized and maintained by each Type 2 device. The list may be updated by examining signal strength and/or processed signal strength associated with the respective set of Type 1 devices. A Type 2 device may choose between a first series of probe signals from a first Type 1 device and a second series of probe signals from a second Type 1 device based on: respective probe signal rate, MAC addresses, channels, characteristics/properties/states, task to be performed by the Type 2 device, signal strength of first and second series, and/or another consideration.

The series of probe signals may be transmitted at a regular rate (e.g. 100 Hz). The series of probe signals may be scheduled at a regular interval (e.g. 0.01 s for 100 Hz), but each probe signal may experience small time perturbation, perhaps due to timing requirement, timing control, network control, handshaking, message passing, collision avoidance, carrier sensing, congestion, availability of resources, and/or another consideration. The rate may be changed (e.g. adjusted, varied, modified). The change may be according to a time table (e.g. changed once every hour), rule, policy, mode, condition and/or change (e.g. changed whenever some event occur). For example, the rate may normally be 100 Hz, but changed to 1000 Hz in demanding situations, and to 1 Hz in low power/standby situation. The probe signals may be sent in burst.

The probe signal rate may change based on a task performed by the Type 1 device or Type 2 device (e.g. a task may need 100 Hz normally and 1000 Hz momentarily for 20 seconds). In one example, the transmitters (Type 1 devices), receivers (Type 2 device), and associated tasks may be associated adaptively (and/or dynamically) to classes (e.g. classes that are: low-priority, high-priority, emergency, critical, regular, privileged, non-subscription, subscription, paying, and/or non-paying). A rate (of a transmitter) may be adjusted for the sake of some class (e.g. high priority class). When the need of that class changes, the rate may be changed (e.g. adjusted, varied, modified). When a receiver has critically low power, the rate may be reduced to reduce power consumption of the receiver to respond to the probe signals. In one example, probe signals may be used to transfer power wirelessly to a receiver (Type 2 device), and the rate may be adjusted to control the amount of power transferred to the receiver.

The rate may be changed by (or based on): a server (e.g. hub device), the Type 1 device and/or the Type 2 device. Control signals may be communicated between them. The server may monitor, track, forecast and/or anticipate the needs of the Type 2 device and/or the tasks performed by the Type 2 device, and may control the Type 1 device to change the rate. The server may make scheduled changes to the rate according to a time table. The server may detect an emergency situation and change the rate immediately. The server may detect a developing condition and adjust the rate gradually. The characteristics and/or STI (e.g. motion information) may be monitored individually based on a TSCI associated with a particular Type 1 device and a particular Type 2 device, and/or monitored jointly based on any TSCI associated with the particular Type 1 device and any Type 2 device, and/or monitored jointly based on any TSCI associated with the particular Type 2 device and any Type 1 device, and/or monitored globally based on any TSCI associated with any Type 1 device and any Type 2 device. Any joint monitoring may be associated with: a user, user account, profile, household, map of venue, environmental model of the venue, and/or user history, etc.

A first channel between a Type 1 device and a Type 2 device may be different from a second channel between another Type 1 device and another Type 2 device. The two channels may be associated with different frequency bands, bandwidth, carrier frequency, modulation, wireless standards, coding, encryption, payload characteristics, networks, network ID, SSID, network characteristics, network settings, and/or network parameters, etc. The two channels may be associated with different kinds of wireless system (e.g. two of the following: WiFi, LTE, LTE-A, LTE-U, 2.5G, 3G, 3.5G, 4G, beyond 4G, 5G, 6G, 7G, a cellular network standard, UMTS, 3GPP, GSM, EDGE, TDMA, FDMA, CDMA, WCDMA, TD-SCDMA, 802.11 system, 802.15 system, 802.16 system, mesh network, Zigbee, NFC, WiMax, Bluetooth, BLE, RFID, UWB, microwave system, radar like system). For example, one is WiFi and the other is LTE. The two channels may be associated with similar kinds of wireless system, but in different network. For example, the first channel may be associated with a WiFi network named "Pizza and Pizza" in the 2.4 GHz band with a bandwidth of 20 MHz while the second may be associated with a WiFi network with SSID of "StarBud hotspot" in the 5 GHz band with a bandwidth of 40 MHz. The two channels may be different channels in same network (e.g. the "StarBud hotspot" network).

In one embodiment, a wireless monitoring system may comprise training a classifier of multiple events in a venue based on training TSCI associated with the multiple events. A CI or TSCI associated with an event may be considered/may comprise a wireless sample/characteristics/fingerprint associated with the event (and/or the venue, the environment, the object, the motion of the object, a state/emotional state/mental state condition/stage/gesture/gait/action/movement/activity/daily activity/history/event of the object, etc.). For each of the multiple known events happening in the venue in a respective training (e.g. surveying, wireless survey, initial wireless survey) time period associated with the known event, a respective training wireless signal (e.g. a respective series of training probe signals) may be transmitted by an antenna of a first Type 1 heterogeneous wireless device using a processor, a memory and a set of instructions of the first Type 1 device to at least one first Type 2 heterogeneous wireless device through a wireless multipath channel in the venue in the respective training time period.

At least one respective time series of training CI (training TSCI) may be obtained asynchronously by each of the at least one first Type 2 device from the (respective) training signal. The CI may be CI of the channel between the first Type 2 device and the first Type 1 device in the training time period associated with the known event. The at least one training TSCI may be preprocessed. The training may be a wireless survey (e.g. during installation of Type 1 device and/or Type 2 device).

For a current event happening in the venue in a current time period, a current wireless signal (e.g. a series of current probe signals) may be transmitted by an antenna of a second Type 1 heterogeneous wireless device using a processor, a memory and a set of instructions of the second Type 1 device to at least one second Type 2 heterogeneous wireless device through the channel in the venue in the current time period associated with the current event. At least one time series of current CI (current TSCI) may be obtained asynchronously by each of the at least one second Type 2 device from the current signal (e.g. the series of current probe signals). The CI may be CI of the channel between the second Type 2 device and the second Type 1 device in the current time period associated with the current event. The at least one current TSCI may be preprocessed.

The classifier may be applied to classify at least one current TSCI obtained from the series of current probe signals by the at least one second Type 2 device, to classify at least one portion of a particular current TSCI, and/or to classify a combination of the at least one portion of the particular current TSCI and another portion of another TSCI. The classifier may partition TSCI (or the characteristics/STI or other analytics or output responses) into clusters and associate the clusters to specific events/objects/subjects/locations/movements/activities. Labels/tags may be generated for the clusters. The clusters may be stored and retrieved. The classifier may be applied to associate the current TSCI (or characteristics/STI or the other analytics/output response, perhaps associated with a current event) with: a cluster, a known/specific event, a class/category/group/grouping/list/cluster/set of known events/subjects/locations/movements/activities, an unknown event, a class/category/group/grouping/list/cluster/set of unknown events/subjects/locations/movements/activities, and/or another event/subject/location/movement/activity/class/category/group/grouping/list/cluster/set. Each TSCI may comprise at least one CI each associated with a respective timestamp. Two TSCI associated with two Type 2 devices may be different with different: starting time, duration, stopping time, amount of CI, sampling frequency, sampling period. Their CI may have different features. The first and second Type 1 devices may be at same location in the venue. They may be the same device. The at least one second Type 2 device (or their locations) may be a permutation of the at least one first Type 2 device (or their locations). A particular second Type 2 device and a particular first Type 2 device may be the same device. A subset of the first Type 2 device and a subset of the second Type 2 device may be the same. The at least one second Type 2 device and/or a subset of the at least one second Type 2 device may be a subset of the at least one first Type 2 device. The at least one first Type 2 device and/or a subset of the at least one first Type 2 device may be a permutation of a subset of the at least one second Type 2 device. The at least one second Type 2 device and/or a subset of the at least one second Type 2 device may be a permutation of a subset of the at least one first Type 2 device. The at least one second Type 2 device and/or a subset of the at least one second Type 2 device may be at same respective location as a subset of the at least one first Type 2 device. The at least one first Type 2 device and/or a subset of the at least one first Type 2 device may be at same respective location as a subset of the at least one second Type 2 device.

The antenna of the Type 1 device and the antenna of the second Type 1 device may be at same location in the venue. Antenna(s) of the at least one second Type 2 device and/or antenna(s) of a subset of the at least one second Type 2 device may be at same respective location as respective antenna(s) of a subset of the at least one first Type 2 device. Antenna(s) of the at least one first Type 2 device and/or antenna(s) of a subset of the at least one first Type 2 device may be at same respective location(s) as respective antenna(s) of a subset of the at least one second Type 2 device.

A first section of a first time duration of the first TSCI and a second section of a second time duration of the second section of the second TSCI may be aligned. A map between items of the first section and items of the second section may be computed. The first section may comprise a first segment (e.g. subset) of the first TSCI with a first starting/ending time, and/or another segment (e.g. subset) of a processed first TSCI. The processed first TSCI may be the first TSCI processed by a first operation. The second section may comprise a second segment (e.g. subset) of the second TSCI with a second starting time and a second ending time, and another segment (e.g. subset) of a processed second TSCI. The processed second TSCI may be the second TSCI processed by a second operation. The first operation and/or the second operation may comprise: subsampling, re-sampling, interpolation, filtering, transformation, feature extraction, pre-processing, and/or another operation.

A first item of the first section may be mapped to a second item of the second section. The first item of the first section may also be mapped to another item of the second section. Another item of the first section may also be mapped to the second item of the second section. The mapping may be one-to-one, one-to-many, many-to-one, many-to-many. At least one function of at least one of: the first item of the first section of the first TSCI, another item of the first TSCI, timestamp of the first item, time difference of the first item, time differential of the first item, neighboring timestamp of the first item, another timestamp associated with the first item, the second item of the second section of the second TSCI, another item of the second TSCI, timestamp of the second item, time difference of the second item, time differential of the second item, neighboring timestamp of the second item, and another timestamp associated with the second item, may satisfy at least one constraint.

One constraint may be that a difference between the timestamp of the first item and the timestamp of the second item may be upper-bounded by an adaptive (and/or dynamically adjusted) upper threshold and lower-bounded by an adaptive lower threshold.

The first section may be the entire first TSCI. The second section may be the entire second TSCI. The first time duration may be equal to the second time duration. A section of a time duration of a TSCI may be determined adaptively (and/or dynamically). A tentative section of the TSCI may be computed. A starting time and an ending time of a section (e.g. the tentative section, the section) may be determined. The section may be determined by removing a beginning portion and an ending portion of the tentative section. A beginning portion of a tentative section may be determined as follows. Iteratively, items of the tentative section with increasing timestamp may be considered as a current item, one item at a time.

In each iteration, at least one activity measure/index may be computed and/or considered. The at least one activity measure may be associated with at least one of: the current item associated with a current timestamp, past items of the tentative section with timestamps not larger than the current timestamp, and/or future items of the tentative section with timestamps not smaller than the current timestamp. The current item may be added to the beginning portion of the tentative section if at least one criterion (e.g. quality criterion, signal quality condition) associated with the at least one activity measure is satisfied.

The at least one criterion associated with the activity measure may comprise at least one of: (a) the activity measure is smaller than an adaptive (e.g. dynamically adjusted) upper threshold, (b) the activity measure is larger than an adaptive lower threshold, (c) the activity measure is smaller than an adaptive upper threshold consecutively for at least a predetermined amount of consecutive timestamps, (d) the activity measure is larger than an adaptive lower threshold consecutively for at least another predetermined amount of consecutive timestamps, (e) the activity measure is smaller than an adaptive upper threshold consecutively for at least a predetermined percentage of the predetermined amount of consecutive timestamps, (f) the activity measure is larger than an adaptive lower threshold consecutively for at least another predetermined percentage of the another predetermined amount of consecutive timestamps, (g) another activity measure associated with another timestamp associated with the current timestamp is smaller than another adaptive upper threshold and larger than another adaptive lower threshold, (h) at least one activity measure associated with at least one respective timestamp associated with the current timestamp is smaller than respective upper threshold and larger than respective lower threshold, (i) percentage of timestamps with associated activity measure smaller than respective upper threshold and larger than respective lower threshold in a set of timestamps associated with the current timestamp exceeds a threshold, and (j) another criterion (e.g. a quality criterion, signal quality condition).

An activity measure/index associated with an item at time T1 may comprise at least one of: (1) a first function of the item at time T1 and an item at time T1−D1, wherein D1 is a pre-determined positive quantity (e.g. a constant time offset), (2) a second function of the item at time T1 and an item at time T1+D1, (3) a third function of the item at time T1 and an item at time T2, wherein T2 is a pre-determined quantity (e.g. a fixed initial reference time; T2 may be changed (e.g. adjusted, varied, modified) over time; T2 may be updated periodically: T2 may be the beginning of a time period and T1 may be a sliding time in the time period), and (4) a fourth function of the item at time T1 and another item.

At least one of: the first function, the second function, the third function, and/or the fourth function may be a function (e.g. F(X, Y, ... )) with at least two arguments: X and Y. The two arguments may be scalars. The function (e.g. F) may be a function of at least one of: X, Y, (X−Y), (Y−X), abs(X−Y), X^a, Y^B, abs(X$^{\rightarrow}$a−Y$^{\rightarrow}$B), (X−Y)^a, (X/Y), (X+a)/(Y+b), (X^a/Y^B), and ((X/Y)^a−b), wherein a and b are may be some predetermined quantities. For example, the function may simply be abs(X−Y), or (X−Y)^2, (X−Y)^4. The function may be a robust function. For example, the function may be (X−Y)^2 when abs (X−Y) is less than a threshold T, and (X−Y)+a when abs(X−Y) is larger than T. Alternatively, the function may be a constant when abs(X−Y) is larger than T. The function may also be bounded by a slowly increasing function when abs(X−y) is larger than T, so that outliers cannot severely affect the result. Another example of the function may be (abs(X/Y)−a), where a=. In this way, if X=Y (i.e. no change or no activity), the function will give a value of 0. If X is larger than Y, (X/Y) will be larger than 1 (assuming X and Y are positive) and the function will be positive. And if X is less than Y, (X/Y) will be smaller than 1 and the function will be negative. In another example, both arguments X and Y may be n-tuples such that X=(x_1, x_2, ... , x_n) and Y=(y_1, y_2, ... , y_n). The function may be a function of at least one of x_i, y_i, (x_i−y_i), (y_i−x_i), abs(x_i−y_i), x_i^a, y_i^b, abs(x_i^a−y_i^B), (x_i−y_i)^a, (x_i/y_i), (x_i+a)/(y_i+b), (x_i^a/y_i^b), and ((x_i/y_i)^a−b), wherein i is a component index of the n-tuple X and Y, and 1<=i<=n. E.g. component index of x_1 is i=1, component index of x_2 is i=2. The function may comprise a component-by-component summation of another function of at least one of the following: x_i, y_i, (x_i−y_i), (y_i−x_i), abs(x_i−y_i), x_i^a, y_i^B, abs(x_i^a−y_i^b), (x_i−y_i)^a, (x_i/y_i), (x_i+a)/(y_i+b), (x_i^a/y_i^b), and ((x_i/y_i)^a−b), wherein i is the component index of the n-tuple X and Y. For example, the function may be in a form of sum_(i=1)^n (abs(x_i/y_i)−1)/n, or sum_{i=1}^n w_i* (abs(x_i/y_i)−1), where w_i is some weight for component i.

The map may be computed using dynamic time warping (DTW). The DTW may comprise a constraint on at least one of: the map, the items of the first TSCI, the items of the second TSCI, the first time duration, the second time duration, the first section, and/or the second section. Suppose in the map, the i^{th} domain item is mapped to the j^{th} range item. The constraint may be on admissible combination of i and j (constraint on relationship between i and j). Mismatch cost between a first section of a first time duration of a first TSCI and a second section of a second time duration of a second TSCI may be computed.

The first section and the second section may be aligned such that a map comprising more than one links may be established between first items of the first TSCI and second items of the second TSCI. With each link, one of the first items with a first timestamp may be associated with one of the second items with a second timestamp. A mismatch cost between the aligned first section and the aligned second section may be computed. The mismatch cost may comprise a function of: an item-wise cost between a first item and a second item associated by a particular link of the map, and a link-wise cost associated with the particular link of the map.

The aligned first section and the aligned second section may be represented respectively as a first vector and a second vector of same vector length. The mismatch cost may comprise at least one of: an inner product, inner-product-like quantity, quantity based on correlation, correlation indicator, quantity based on covariance, discriminating score, distance, Euclidean distance, absolute distance, Lk distance (e.g. L1, L2, . . . ), weighted distance, distance-like quantity and/or another similarity value, between the first vector and the second vector. The mismatch cost may be normalized by the respective vector length.

A parameter derived from the mismatch cost between the first section of the first time duration of the first TSCI and the second section of the second time duration of the second TSCI may be modeled with a statistical distribution. At least one of: a scale parameter, location parameter and/or another parameter, of the statistical distribution may be estimated. The first section of the first time duration of the first TSCI may be a sliding section of the first TSCI. The second section of the second time duration of the second TSCI may be a sliding section of the second TSCI. A first sliding window may be applied to the first TSCI and a corresponding second sliding window may be applied to the second TSCI. The first sliding window of the first TSCI and the corresponding second sliding window of the second TSCI may be aligned.

Mismatch cost between the aligned first sliding window of the first TSCI and the corresponding aligned second sliding window of the second TSCI may be computed. The current event may be associated with at least one of: the known event, the unknown event and/or the another event, based on the mismatch cost.

The classifier may be applied to at least one of: each first section of the first time duration of the first TSCI, and/or each second section of the second time duration of the second TSCI, to obtain at least one tentative classification results. Each tentative classification result may be associated with a respective first section and a respective second section.

The current event may be associated with at least one of: the known event, the unknown event, a class/category/group/grouping/list/set of unknown events, and/or the another event, based on the mismatch cost. The current event may be associated with at least one of: the known event, the unknown event and/or the another event, based on a largest number of tentative classification results in more than one sections of the first TSCI and corresponding more than sections of the second TSCI. For example, the current event may be associated with a particular known event if the mismatch cost points to the particular known event for N consecutive times (e.g. N=10). In another example, the current event may be associated with a particular known event if the percentage of mismatch cost within the immediate past N consecutive N pointing to the particular known event exceeds a certain threshold (e.g. >80%). In another example, the current event may be associated with a known event that achieves smallest mismatch cost for the most times within a time period. The current event may be associated with a known event that achieves smallest overall mismatch cost, which is a weighted average of at least one mismatch cost associated with the at least one first sections. The current event may be associated with a particular known event that achieves smallest of another overall cost. The current event may be associated with the "unknown event" if none of the known events achieve mismatch cost lower than a first threshold T1 in a sufficient percentage of the at least one first section. The current event may also be associated with the "unknown event" if none of the events achieve an overall mismatch cost lower than a second threshold T2. The current event may be associated with at least one of: the known event, the unknown event and/or the another event, based on the mismatch cost and additional mismatch cost associated with at least one additional section of the first TSCI and at least one additional section of the second TSCI. The known events may comprise at least one of: a door closed event, door open event, window closed event, window open event, multi-state event, on-state event, off-state event, intermediate state event, continuous state event, discrete state event, human-present event, human-absent event, sign-of-life-present event, and/or a sign-of-life-absent event.

A projection for each CI may be trained using a dimension reduction method based on the training TSCI. The dimension reduction method may comprise at least one of: principal component analysis (PCA), PCA with different kernel, independent component analysis (ICA), Fisher linear discriminant, vector quantization, supervised learning, unsupervised learning, self-organizing maps, auto-encoder, neural network, deep neural network, and/or another method. The projection may be applied to at least one of: the training TSCI associated with the at least one event, and/or the current TSCI, for the classifier. The classifier of the at least one event may be trained based on the projection and the training TSCI associated with the at least one event. The at least one current TSCI may be classified/categorized based on the projection and the current TSCI. The projection may be re-trained using at least one of: the dimension reduction method, and another dimension reduction method, based on at least one of: the training TSCI, at least one current TSCI before retraining the projection, and/or additional training TSCI. The another dimension reduction method may comprise at least one of: principal component analysis (PCA), PCA with different kernels, independent component analysis (ICA), Fisher linear discriminant, vector quantization, supervised learning, unsupervised learning, self-organizing maps, auto-encoder, neural network, deep neural network, and/or yet another method. The classifier of the at least one event may be re-trained based on at least one of: the re-trained projection, the training TSCI associated with the at least one events, and/or at least one current TSCI. The at least one current TSCI may be classified based on: the re-trained projection, the re-trained classifier, and/or the current TSCI.

Each CI may comprise a vector of complex values. Each complex value may be preprocessed to give the magnitude of the complex value. Each CI may be preprocessed to give a vector of non-negative real numbers comprising the magnitude of corresponding complex values. Each training TSCI may be weighted in the training of the projection. The projection may comprise more than one projected components. The projection may comprise at least one most significant projected component. The projection may comprise at least one projected component that may be beneficial for the classifier.

The channel information (CI) may be associated with/may comprise signal strength, signal amplitude, signal phase, spectral power measurement, modem parameters (e.g. used in relation to modulation/demodulation in digital communication systems such as WiFi, 4G/LTE), dynamic beamforming information, transfer function components, radio state (e.g. used in digital communication systems to decode digital data, baseband processing state, RF processing state, etc.), measurable variables, sensed data, coarse-grained/fine-grained information of a layer (e.g. physical layer, data link layer, MAC layer, etc.), digital setting, gain setting, RF filter setting, RF front end switch setting, DC offset setting, DC correction setting, IQ compensation setting, effect(s) on the wireless signal by the environment (e.g. venue) during propagation, transformation of an input signal (the wireless signal transmitted by the Type 1 device) to an output signal (the wireless signal received by the Type 2 device), a stable behavior of the environment, a state profile, wireless channel measurements, received signal strength indicator (RSSI), channel state information (CSI), channel impulse response (CIR), channel frequency response (CFR), characteristics of frequency components (e.g. subcarriers) in a bandwidth, channel characteristics, channel filter response, timestamp, auxiliary information, data, meta data, user data, account data, access data, security data, session data, status data, supervisory data, household data, identity (ID), identifier, device data, network data, neighborhood data, environment data, real-time data, sensor data, stored data, encrypted data, compressed data, protected data, and/or another channel information. Each CI may be associated with a time stamp, and/or an arrival time. A CS can be used to equalize/undo/minimize/reduce the multipath channel effect (of the transmission channel) to demodulate a signal similar to the one transmitted by the transmitter through the multipath channel. The CI may be associated with information associated with a frequency band, frequency signature, frequency phase, frequency amplitude, frequency trend, frequency characteristics, frequency-like characteristics, time domain element, frequency domain element, time-frequency domain element, orthogonal decomposition characteristics, and/or non-orthogonal decomposition characteristics of the signal through the channel. The TSCI may be a stream of wireless signals (e.g. CI).

The CI may be preprocessed, processed, postprocessed, stored (e.g. in local memory, portable/mobile memory, removable memory, storage network, cloud memory, in a volatile manner, in a non-volatile manner), retrieved, transmitted and/or received. One or more modem parameters and/or radio state parameters may be held constant. The modem parameters may be applied to a radio subsystem. The modem parameters may represent a radio state. A motion detection signal (e.g. baseband signal, and/or packet decoded/demodulated from the baseband signal, etc.) may be obtained by processing (e.g. down-converting) the first wireless signal (e.g. RF/WiFi/LTE/5G signal) by the radio subsystem using the radio state represented by the stored modem parameters. The modem parameters/radio state may be updated (e.g. using previous modem parameters or previous radio state). Both the previous and updated modem parameters/radio states may be applied in the radio subsystem in the digital communication system. Both the previous and updated modem parameters/radio states may be compared/analyzed processed/monitored in the task.

The channel information may also be modem parameters (e.g. stored or freshly computed) used to process the wireless signal. The wireless signal may comprise a plurality of probe signals. The same modem parameters may be used to process more than one probe signals. The same modem parameters may also be used to process more than one wireless signals. The modem parameters may comprise parameters that indicate settings or an overall configuration for the operation of a radio subsystem or a baseband subsystem of a wireless sensor device (or both). The modem parameters may include one or more of; a gain setting, an RF filter setting, an RF front end switch setting, a DC offset setting, or an IQ compensation setting for a radio subsystem, or a digital DC correction setting, a digital gain setting, and/or a digital filtering setting (e.g. for a baseband subsystem). The CI may also be associated with information associated with a time period, time signature, timestamp, time amplitude, time phase, time trend, and/or time characteristics of the signal. The CI may be associated with information associated with a time-frequency partition, signature, amplitude, phase, trend, and/or characteristics of the signal. The CI may be associated with a decomposition of the signal. The CI may be associated with information associated with a direction, angle of arrival (AoA), angle of a directional antenna, and/or a phase of the signal through the channel. The CI may be associated with attenuation patterns of the signal through the channel. Each CI may be associated with a Type 1 device and a Type 2 device. Each CI may be associated with an antenna of the Type 1 device and an antenna of the Type 2 device.

The CI may be obtained from a communication hardware (e.g. of Type 2 device, or Type 1 device) that is capable of providing the CI. The communication hardware may be a WiFi-capable chip/IC (integrated circuit), chip compliant with a 802.11 or 802.16 or another wireless/radio standard, next generation WiFi-capable chip, LTE-capable chip, 5G-capable chip, 6G/7G/8G-capable chip, Bluetooth-enabled chip, NFC (near field communication)-enabled chip, BLE (Bluetooth low power)-enabled chip, UWB chip, another communication chip (e.g. Zigbee, WiMax, mesh network), etc. The communication hardware computes the CI and stores the CI in a buffer memory and make the CI available for extraction. The CI may comprise data and/or at least one matrices related to channel state information (CSI). The at least one matrices may be used for channel equalization, and/or beam forming, etc. The channel may be associated with a venue. The attenuation may be due to signal propagation in the venue, signal propagating/reflection refraction/diffraction through/at/around air (e.g. air of venue), refraction medium/reflection surface such as wall, doors, furniture, obstacles and/or barriers, etc. The attenuation may be due to reflection at surfaces and obstacles (e.g. reflection surface, obstacle) such as floor, ceiling, furniture, fixtures, objects, people, pets, etc. Each CI may be associated with a timestamp. Each CI may comprise N1 components (e.g. N1 frequency domain components in CFR, N1 time domain components in CIR, or N1 decomposition components). Each component may be associated with a component index. Each component may be a real, imaginary, or complex quantity, magnitude, phase, flag, and/or set. Each CI may comprise a vector or matrix of complex numbers, a set of mixed quantities, and/or a multi-dimensional collection of at least one complex numbers.

Components of a TSCI associated with a particular component index may form a respective component time series associated with the respective index. A TSCI may be divided into N1 component time series. Each respective component time series is associated with a respective component index. The characteristics/STI of the motion of the object may be monitored based on the component time series. In one example, one or more ranges of CIC (e.g. one range being from component 11 to component 23, a second range being from component 44 to component 50, and a third range having only one component) may be selected based on some criteria/cost function/signal quality metric (e.g. based on signal-to-noise ratio, and/or interference level) for further processing.

A component-wise characteristic of a component-feature time series of a TSCI may be computed. The component-wise characteristics may be a scalar (e.g. energy) or a function with a domain and a range (e.g. an autocorrelation function, transform, inverse transform). The characteristics/STI of the motion of the object may be monitored based on the component-wise characteristics. A total characteristics (e.g. aggregate characteristics) of the TSCI may be computed based on the component-wise characteristics of each component time series of the TSCI. The total characteristics may be a weighted average of the component-wise characteristics. The characteristics/STI of the motion of the object may be monitored based on the total characteristics. An aggregate quantity may be a weighted average of individual quantities.

The Type 1 device and Type 2 device may support WiFi, WiMax, 3G/beyond 3G, 4G/beyond 4G, LTE, LTE-A, 5G, 6G, 7G, Bluetooth, NFC, BLE, Zigbee, UWB, UMTS, 3GPP, GSM, EDGE, TDMA, FDMA, CDMA, WCDMA, TD-SCDMA, mesh network, proprietary wireless system, IEEE 802.11 standard, 802.15 standard, 802.16 standard, 3GPP standard, and/or another wireless system.

A common wireless system and/or a common wireless channel may be shared by the Type 1 transceiver and/or the at least one Type 2 transceiver. The at least one Type 2 transceiver may transmit respective signal contemporaneously (or: asynchronously, synchronously, sporadically, continuously, repeatedly, concurrently, simultaneously and/or temporarily) using the common wireless system and/or the common wireless channel. The Type 1 transceiver may transmit a signal to the at least one Type 2 transceiver using the common wireless system and/or the common wireless channel.

Each Type 1 device and Type 2 device may have at least one transmitting/receiving antenna. Each CI may be associated with one of the transmitting antenna of the Type 1 device and one of the receiving antenna of the Type 2 device. Each pair of a transmitting antenna and a receiving antenna may be associated with a link, a path, a communication path, signal hardware path, etc. For example, if the Type 1 device has M (e.g. 3) transmitting antennas, and the Type 2 device has N (e.g. 2) receiving antennas, there may be M×N (e.g. 3×2=6) links or paths. Each link or path may be associated with a TSCI.

The at least one TSCI may correspond to various antenna pairs between the Type 1 device and the Type 2 device. The Type 1 device may have at least one antenna. The Type 2 device may also have at least one antenna. Each TSCI may be associated with an antenna of the Type 1 device and an antenna of the Type 2 device. Averaging or weighted averaging over antenna links may be performed. The averaging or weighted averaging may be over the at least one TSCI. The averaging may optionally be performed on a subset of the at least one TSCI corresponding to a subset of the antenna pairs.

Timestamps of CI of a portion of a TSCI may be irregular and may be corrected so that corrected timestamps of time-corrected CI may be uniformly spaced in time. In the case of multiple Type 1 devices and/or multiple Type 2 devices, the corrected timestamp may be with respect to the same or different clock. An original timestamp associated with each of the CI may be determined. The original timestamp may not be uniformly spaced in time. Original timestamps of all CI of the particular portion of the particular TSCI in the current sliding time window may be corrected so that corrected timestamps of time-corrected CI may be uniformly spaced in time.

The characteristics and/or STI (e.g. motion information) may comprise: location, location coordinate, change in location, position (e.g. initial position, new position), position on map, height, horizontal location, vertical location, distance, displacement, speed, acceleration, rotational speed, rotational acceleration, direction, angle of motion, azimuth, direction of motion, rotation, path, deformation, transformation, shrinking, expanding, gait, gait cycle, head motion, repeated motion, periodic motion, pseudo-periodic motion, impulsive motion, sudden motion, fall-down motion, transient motion, behavior, transient behavior, period of motion, frequency of motion, time trend, temporal profile, temporal characteristics, occurrence, change, temporal change, change of CI, change in frequency, change in timing, change of gait cycle, timing, starting time, initiating time, ending time, duration, history of motion, motion type, motion classification, frequency, frequency spectrum, frequency characteristics, presence, absence, proximity, approaching, receding, identity/identifier of the object, composition of the object, head motion rate, head motion direction, mouth-related rate, eye-related rate, breathing rate, heart rate, tidal volume, depth of breath, inhale time, exhale time, inhale time to exhale time ratio, airflow rate, heart heat-to-beat interval, heart rate variability, hand motion rate, hand motion direction, leg motion, body motion, walking rate, hand motion rate, positional characteristics, characteristics associated with movement (e.g. change in position/location) of the object, tool motion, machine motion, complex motion, and/or combination of multiple motions, event, signal statistics, signal dynamics, anomaly, motion statistics, motion parameter, indication of motion detection, motion magnitude, motion phase, similarity score, distance score, Euclidean distance, weighted distance, $L\_1$ norm, $L\_2$ norm, $L\_k$ norm for k>2, statistical distance, correlation, correlation indicator, auto-correlation, covariance, auto-covariance, cross-covariance, inner product, outer product, motion signal transformation, motion feature, presence of motion, absence of motion, motion localization, motion identification, motion recognition, presence of object, absence of object, entrance of object, exit of object, a change of object, motion cycle, motion count, gait cycle, motion rhythm, deformation motion, gesture, handwriting, head motion, mouth motion, heart motion, internal organ motion, motion trend, size, length, area, volume, capacity, shape, form, tag, starting/initiating location, ending location, starting/initiating quantity, ending quantity, event, fall-down event, security event, accident event, home event, office event, factory event, warehouse event, manufacturing event, assembly line event, maintenance event, car-related event, navigation event, tracking event, door event, door-open event, door-close event, window event, window-open event, window-close event, repeatable event, one-time event, consumed quantity, unconsumed quantity, state, physical state, health state, well-being state, emotional state, mental state, another event, analytics, output responses, and/or another information. The characteristics and/or STI may be computed/monitored based on a feature computed from a CI or a TSCI (e.g. feature computation/extraction). A static segment or profile (and/or a dynamic segment/profile) may be identified/computed/analyzed/monitored/extracted/obtained/marked/disclosed/indicated/highlighted/stored/communicated based on an analysis of the feature. The analysis may comprise a motion detection/movement assessment/presence detection. Computational workload may be shared among the Type 1 device, the Type 2 device and another processor.

The Type 1 device and/or Type 2 device may be a local device. The local device may be: a smart phone, smart device, TV, sound bar, set-top box, access point, router, repeater, wireless signal repeater/extender, remote control, speaker, fan, refrigerator, microwave, oven, coffee machine, hot water pot, utensil, table, chair, light, lamp, door lock, camera, microphone, motion sensor, security device, fire hydrant, garage door, switch, power adapter, computer, dongle, computer peripheral, electronic pad, sofa, tile, accessory, home device, vehicle device, office device, building device, manufacturing device, watch, glasses, clock, television, oven, air-conditioner, accessory, utility, appliance, smart machine, smart vehicle, internet-of-thing (IoT) device, internet-enabled device, computer, portable computer, tablet, smart house, smart office, smart building, smart parking lot, smart system, and/or another device.

Each Type 1 device may be associated with a respective identifier (e.g. ID). Each Type 2 device may also be associated with a respective identify (ID). The ID may comprise: numeral, combination of text and numbers, name, password, account, account ID, web link, web address, index to some information, and/or another ID. The ID may be assigned. The ID may be assigned by hardware (e.g. hardwired, via dongle and/or other hardware), software and/or firmware. The ID may be stored (e.g. in database, in memory, in server (e.g. hub device), in the cloud, stored locally, stored remotely, stored permanently, stored temporarily) and may be retrieved. The ID may be associated with at least one record, account, user, household, address, phone number, social security number, customer number, another ID, another identifier, timestamp, and/or collection of data. The ID and/or part of the ID of a Type 1 device may be made available to a Type 2 device. The ID may be used for registration, initialization, communication, identification, verification, detection, recognition, authentication, access control, cloud access, networking, social networking, logging, recording, cataloging, classification, tagging, association, pairing, transaction, electronic transaction, and/or intellectual property control, by the Type 1 device and/or the Type 2 device.

The object may be person, user, subject, passenger, child, older person, baby, sleeping baby, baby in vehicle, patient, worker, high-value worker, expert, specialist, waiter, customer in mall, traveler in airport/train station/bus terminal/shipping terminals, staff/worker/customer service personnel in factory/mall/supermarket/office/workplace, serviceman in sewage/air ventilation system/lift well, lifts in lift wells, elevator, inmate, people to be tracked/monitored, animal, plant, living object, pet, dog, cat, smart phone, phone accessory, computer, tablet, portable computer, dongle, computing accessory, networked devices, WiFi devices, IoT devices, smart watch, smart glasses, smart devices, speaker, keys, smart key, wallet, purse, handbag, backpack, goods, cargo, luggage, equipment, motor, machine, air conditioner, fan, air conditioning equipment, light fixture, moveable light, television, camera, audio and/or video equipment, stationary, surveillance equipment, parts, signage, tool, cart, ticket, parking ticket, toll ticket, airplane ticket, credit card, plastic card, access card, food packaging, utensil, table, chair, cleaning equipment/tool, vehicle, car, cars in parking facilities, merchandise in warehouse/store/supermarket/distribution center, boat, bicycle, airplane, drone, remote control car/plane/boat, robot, manufacturing device, assembly line, material/unfinished part/robot/wagon/transports on factory floor, object to be tracked in airport/shopping mart/supermarket, non-object, absence of an object, presence of an object, object with form, object with changing form, object with no form, mass of fluid, mass of liquid, mass of gas/smoke, fire, flame, electromagnetic (EM) source, EM medium, and/or another object. The object itself may be communicatively coupled with some network, such as WiFi, MiFi, 3G 4G/LTE/5G/6G/7G, Bluetooth, NFC, BLE, WiMax, Zigbee, UMTS, 3GPP, GSM, EDGE, TDMA, FDMA, CDMA, WCDMA, TD-SCDMA, mesh network, adhoc network, and/or other network. The object itself may be bulky with AC power supply, but is moved during installation, cleaning, maintenance, renovation, etc. It may also be installed in moveable platform such as lift, pad, movable, platform, elevator, conveyor belt, robot, drone, forklift, car, boat, vehicle, etc. The object may have multiple parts, each part with different movement (e.g. change in position/location). For example, the object may be a person walking forward. While walking, his left hand and right hand may move in different direction, with different instantaneous speed, acceleration, motion, etc.

The wireless transmitter (e.g. Type 1 device), the wireless receiver (e.g. Type 2 device), another wireless transmitter and/or another wireless receiver may move with the object and/or another object (e.g. in prior movement, current movement and/or future movement. They may be communicatively coupled to one or more nearby device. They may transmit TSCI and/or information associated with the TSCI to the nearby device, and/or each other. They may be with the nearby device. The wireless transmitter and/or the wireless receiver may be part of a small (e.g. coin-size, cigarette box size, or even smaller), light-weight portable device. The portable device may be wirelessly coupled with a nearby device.

The nearby device may be smart phone, iPhone, Android phone, smart device, smart appliance, smart vehicle, smart gadget, smart TV, smart refrigerator, smart speaker, smart watch, smart glasses, smart pad, iPad, computer, wearable computer, notebook computer, gateway. The nearby device may be connected to a cloud server, local server (e.g. hub device) and/or other server via internet, wired internet connection and/or wireless internet connection. The nearby device may be portable. The portable device, the nearby device, a local server (e.g. hub device) and/or a cloud server may share the computation and/or storage for a task (e.g. obtain TSCI, determine characteristics/STI of the object associated with the movement (e.g. change in position/location) of the object, computation of time series of power (e.g. signal strength) information, determining/computing the particular function, searching for local extremum, classification, identifying particular value of time offset, denoising, processing, simplification, cleaning, wireless smart sensing task, extract CI from signal, switching, segmentation, estimate trajectory/path/track, process the map, processing trajectory/path/track based on environment models/constraints/limitations, correction, corrective adjustment, adjustment, map-based (or model-based) correction, detecting error, checking for boundary hitting, thresholding) and information (e.g. TSCI). The nearby device may/may not move with the object. The nearby device may be portable/not portable/moveable/non-moveable. The nearby device may use battery power, solar power, AC power and/or other power source. The nearby device may have replaceable/non-replaceable battery, and/or rechargeable/non-rechargeable battery. The nearby device may be similar to the object. The nearby device may have identical (and/or similar) hardware and/or software to the object. The nearby device may be a smart device, network enabled device, device with connection to WiFi/3G/4G/5G/6G/Zigbee/Bluetooth/NFC/UMTS/3GPP/GSM/EDGE/TDMA/FDMA/CDMA/WCDMA/TD-SCDMA/adhoc network/other network, smart speaker, smart watch, smart clock, smart appliance, smart machine, smart equipment, smart tool, smart vehicle, internet-of-thing (IoT) device, internet-enabled device, computer, portable computer, tablet, and another device. The nearby device and/or at least one processor associated with the wireless receiver, the wireless transmitter, the another wireless receiver, the another wireless transmitter and/or a cloud server (in the cloud) may determine the initial STI of the object. Two or more of them may determine the initial spatial-temporal info jointly. Two or more of them may share intermediate information in the determination of the initial STI (e.g. initial position).

In one example, the wireless transmitter (e.g. Type 1 device, or Tracker Bot) may move with the object. The wireless transmitter may send the signal to the wireless receiver (e.g. Type 2 device, or Origin Register) or determining the initial STI (e.g. initial position) of the object. The wireless transmitter may also send the signal and/or another signal to another wireless receiver (e.g. another Type 2 device, or another Origin Register) for the monitoring of the motion (spatial-temporal info) of the object. The wireless receiver may also receive the signal and/or another signal from the wireless transmitter and/or the another wireless transmitter for monitoring the motion of the object. The location of the wireless receiver and/or the another wireless receiver may be known. In another example, the wireless receiver (e.g. Type 2 device, or Tracker Bot) may move with the object. The wireless receiver may receive the signal transmitted from the wireless transmitter (e.g. Type 1 device, or Origin Register) for determining the initial spatial-temporal info (e.g. initial position) of the object. The wireless receiver may also receive the signal and/or another signal from another wireless transmitter (e.g. another Type 1 device, or another Origin Register) for the monitoring of the current motion (e.g. spatial-temporal info) of the object. The wireless transmitter may also transmit the signal and/or another signal to the wireless receiver and/or the another wireless receiver (e.g. another Type 2 device, or another Tracker Bot) for monitoring the motion of the object. The location of the wireless transmitter and/or the another wireless transmitter may be known.

The venue may be a space such as a sensing area, room, house, office, property, workplace, hallway, walkway, lift, lift well, escalator, elevator, sewage system, air ventilations system, staircase, gathering area, duct, air duct, pipe, tube, enclosed space, enclosed structure, semi-enclosed structure, enclosed area, area with at least one wall, plant, machine, engine, structure with wood, structure with glass, structure with metal, structure with walls, structure with doors, structure with gaps, structure with reflection surface, structure with fluid, building, roof top, store, factory, assembly line, hotel room, museum, classroom, school, university, government building, warehouse, garage, mall, airport, train station, bus terminal, hub, transportation hub, shipping terminal, government facility, public facility, school, university, entertainment facility, recreational facility, hospital, pediatric/neonatal wards, seniors home, elderly care facility, geriatric facility, community center, stadium, playground, park, field, sports facility, swimming facility, track and/or field, basketball court, tennis court, soccer stadium, baseball stadium, gymnasium, hall, garage, shopping mart, mall, supermarket, manufacturing facility, parking facility, construction site, mining facility, transportation facility, highway, road, valley, forest, wood, terrain, landscape, den, patio, land, path, amusement park, urban area, rural area, suburban area, metropolitan area, garden, square, plaza, music hall, downtown facility, over-air facility, semi-open facility, closed area, train platform, train station, distribution center, warehouse, store, distribution center, storage facility, underground facility, space (e.g. above ground, outer-space) facility, floating facility, cavern, tunnel facility, indoor facility, open-air facility, outdoor facility with some walls/doors/reflective barriers, open facility, semi-open facility, car, truck, bus, van, container, ship/boat, submersible, train, tram, airplane, vehicle, mobile home, cave, tunnel, pipe, channel, metropolitan area, downtown area with relatively tall buildings, valley, well, duct, pathway, gas line, oil line, water pipe, network of interconnecting pathways/alleys/roads/tubes/cavities/caves/pipe-like structure/air space/fluid space, human body, animal body, body cavity, organ, bone, teeth, soft tissue, hard tissue, rigid tissue, non-rigid tissue, blood/body fluid vessel, windpipe, air duct, den, etc. The venue may be indoor space, outdoor space, The venue may include both the inside and outside of the space. For example, the venue may include both the inside of a building and the outside of the building. For example, the venue can be a building that has one floor or multiple floors, and a portion of the building can be underground. The shape of the building can be, e.g., round, square, rectangular, triangle, or irregular-shaped. These are merely examples. The disclosure can be used to detect events in other types of venue or spaces.

The wireless transmitter (e.g. Type 1 device) and/or the wireless receiver (e.g. Type 2 device) may be embedded in a portable device (e.g. a module, or a device with the module) that may move with the object (e.g. in prior movement and/or current movement). The portable device may be communicatively coupled with the object using a wired connection (e.g. through USB, microUSB, Firewire, HDMI, serial port, parallel port, and other connectors) and/or a connection (e.g. Bluetooth, Bluetooth Low Energy (BLE), WiFi, LTE, NFC, ZigBee). The portable device may be a lightweight device. The portable may be powered by battery, rechargeable battery and/or AC power. The portable device may be very small (e.g. at sub-millimeter scale and/or sub-centimeter scale), and/or small (e.g. coin-size, card-size, pocket-size, or larger). The portable device may be large, sizable, and/or bulky (e.g. heavy machinery to be installed). The portable device may be a WiFi hotspot, access point, mobile WiFi (MiFi), dongle with USB/micro USB/Firewire/other connector, smartphone, portable computer, computer, tablet, smart device, internet-of-thing (IoT) device, WiFi-enabled device, LTE-enabled device, a smart watch, smart glass, smart mirror, smart antenna, smart battery, smart light, smart pen, smart ring, smart door, smart window, smart clock, small battery, smart wallet, smart belt, smart handbag, smart clothing/garment, smart ornament, smart packaging, smart paper/book/magazine/poster/printed matter/signage/display/lighted system/lighting system, smart key/tool, smart bracelet/chain/necklace/wearable/accessory, smart pad/cushion, smart tile/block/brick/building material/other material, smart garbage can/waste container, smart food carriage/storage, smart ball/racket, smart chair/sofa/bed, smart shoe/footwear/carpet/mat/shoe rack, smart glove/hand wear/ring/hand ware, smart hat/headwear/makeup/sticker/tattoo, smart mirror, smart toy, smart pill, smart utensil, smart bottle/food container, smart tool, smart device, IoT device, WiFi enabled device, network enabled device, 3G/4G/5G/6G enabled device, UMTS devices, 3GPP devices, GSM devices, EDGE devices, TDMA devices, FDMA devices, CDMA devices, WCDMA devices, TD-SCDMA devices, embeddable device, implantable device, air conditioner, refrigerator, heater, furnace, furniture, oven, cooking device, television/set-top box (STB)/DVD player/audio player video player/remote control, hi-fi, audio device, speaker, lamp/light, wall, door, window, roof, roof tile shingle/structure/attic structure/device/feature/installation/fixtures, lawn mower/garden tools/yard tools/mechanics tools garage tools/, garbage can/container, 20-ft/40-ft container, storage container, factory/manufacturing/production device, repair tools, fluid container, machine, machinery to be installed, vehicle, cart, wagon, warehouse vehicle, car, bicycle, motorcycle, boat, vessel, airplane, basket/box/bag/ bucket/container, smart plate/cup/bowl/pot/mat utensils/ kitchen tools/kitchen devices/kitchen accessories/cabinets/ tables/chairs/tiles/lights/water pipes/taps/gas range/oven/ dishwashing machine/etc. The portable device may have a battery that may be replaceable, irreplaceable, rechargeable, and/or non-rechargeable. The portable device may be wirelessly charged. The portable device may be a smart payment card. The portable device may be a payment card used in parking lots, highways, entertainment parks, or other venues/facilities that need payment. The portable device may have an identity (ID)/identifier as described above.

An event may be monitored based on the TSCI. The event may be an object related event, such as fall-down of the object (e.g. an person and/or a sick person), rotation, hesitation, pause, impact (e.g. a person hitting a sandbag, door, window, bed, chair, table, desk, cabinet, box, another person, animal, bird, fly, table, chair, ball, bowling ball, tennis ball, football, soccer ball, baseball, basketball, volley ball), two-body action (e.g. a person letting go a balloon, catching a fish, molding a clay, writing a paper, person typing on a computer), car moving in a garage, person carrying a smart phone and walking around an airport/mall/government building/office/etc., autonomous moveable object/machine moving around (e.g. vacuum cleaner, utility vehicle, car, drone, self-driving car). The task or the wireless smart sensing task may comprise: object detection, presence detection, proximity detection, object recognition, activity recognition, object verification, object counting, daily activity monitoring, well-being monitoring, vital sign monitoring, health condition monitoring, baby monitoring, elderly monitoring, sleep monitoring, sleep stage monitoring, walking monitoring, exercise monitoring, tool detection, tool recognition, tool verification, patient detection, patient monitoring, patient verification, machine detection, machine recognition, machine verification, human detection, human recognition, human verification, baby detection, baby recognition, baby verification, human breathing detection, human breathing recognition, human breathing estimation, human breathing verification, human heart beat detection, human heart beat recognition, human heart beat estimation, human heart beat verification, fall-down detection, fall-down recognition, fall-down estimation, fall-down verification, emotion detection, emotion recognition, emotion estimation, emotion verification, motion detection, motion degree estimation, motion recognition, motion estimation, motion verification, periodic motion detection, periodic motion recognition, periodic motion estimation, periodic motion verification, repeated motion detection, repeated motion recognition, repeated motion estimation, repeated motion verification, stationary motion detection, stationary motion recognition, stationary motion estimation, stationary motion verification, cyclo-stationary motion detection, cyclo-stationary motion recognition, cyclo-stationary motion estimation, cyclo-stationary motion verification, transient motion detection, transient motion recognition, transient motion estimation, transient motion verification, trend detection, trend recognition, trend estimation, trend verification, breathing detection, breathing recognition, breathing estimation, breathing estimation, human biometrics detection, human biometric recognition, human biometrics estimation, human biometrics verification, environment informatics detection, environment informatics recognition, environment informatics estimation, environment informatics verification, gait detection, gait recognition, gait estimation, gait verification, gesture detection, gesture recognition, gesture estimation, gesture verification, machine learning, supervised learning, unsupervised learning, semi-supervised learning, clustering, feature extraction, featuring training, principal component analysis, eigen-decomposition, frequency decomposition, time decomposition, time-frequency decomposition, functional decomposition, other decomposition, training, discriminative training, supervised training, unsupervised training, semi-supervised training, neural network, sudden motion detection, fall-down detection, danger detection, life-threat detection, regular motion detection, stationary motion detection, cyclo-stationary motion detection, intrusion detection, suspicious motion detection, security, safety monitoring, navigation, guidance, map-based processing, map-based correction, model-based processing/ correction, irregularity detection, locationing, room sensing, tracking, multiple object tracking, indoor tracking, indoor position, indoor navigation, energy management, power transfer, wireless power transfer, object counting, car tracking in parking garage, activating a device/system (e.g. security system, access system, alarm, siren, speaker, television, entertaining system, camera, heater/air-conditioning (HVAC) system, ventilation system, lighting system, gaming system, coffee machine, cooking device, cleaning device, housekeeping device), geometry estimation, augmented reality, wireless communication, data communication, signal broadcasting, networking, coordination, administration, encryption, protection, cloud computing, other processing and/or other task. The task may be performed by the Type 1 device, the Type 2 device, another Type 1 device, another Type 2 device, a nearby device, a local server (e.g. hub device), edge server, a cloud server, and/or another device. The task may be based on TSCI between any pair of Type 1 device and Type 2 device. A Type 2 device may be a Type 1 device, and vice versa. A Type 2 device may play/perform the role (e.g. functionality) of Type 1 device temporarily, continuously, sporadically, simultaneously, and/or contemporaneously, and vice versa. A first part of the task may comprise at least one of: preprocessing, processing, signal conditioning, signal processing, post-processing, processing sporadically/continuously/simultaneously/contemporaneously/dynamically/adaptive/on-demand/as-needed, calibrating, denoising, feature extraction, coding, encryption, transformation, mapping, motion detection, motion estimation, motion change detection, motion pattern detection, motion pattern estimation, motion pattern recognition, vital sign detection, vital sign estimation, vital sign recognition, periodic motion detection, periodic motion estimation, repeated motion detection/estimation, breathing rate detection, breathing rate estimation, breathing pattern detection, breathing pattern estimation, breathing pattern recognition, heart beat detection, heart beat estimation, heart pattern detection, heart pattern estimation, heart pattern recognition, gesture detection, gesture estimation, gesture recognition, speed detection, speed estimation, object locationing, object tracking, navigation, acceleration estimation, acceleration detection, fall-down detection, change detection, intruder (and/or illegal action) detection, baby detection, baby monitoring, patient monitoring, object recognition, wireless power transfer, and/or wireless charging.

A second part of the task may comprise at least one of a smart home task, smart office task, smart building task, smart factory task (e.g. manufacturing using a machine or an assembly line), smart internet-of-thing (IoT) task, smart system task, smart home operation, smart office operation, smart building operation, smart manufacturing operation (e.g. moving supplies/parts/raw material to a machine/an assembly line), IoT operation, smart system operation, turning on a light, turning off the light, controlling the light in at least one of: a room, region, and/or the venue, playing a sound clip, playing the sound clip in at least one of the room, the region, and/or the venue, playing the sound clip of at least one of: a welcome, greeting, farewell, first message, and/or a second message associated with the first part of the task, turning on an appliance, turning off the appliance, controlling the appliance in at least one of: the room, the region, and/or the venue, turning on an electrical system, turning off the electrical system, controlling the electrical system in at least one of: the room, the region, and/or the venue, turning on a security system, turning off the security system, controlling the security system in at least one of: the room, the region, and/or the venue, turning on a mechanical system, turning off a mechanical system, controlling the mechanical system in at least one of: the room, the region, and/or the venue, and/or controlling at least one of: an air conditioning system, heating system, ventilation system, lighting system, heating device, stove, entertainment system, door, fence, window, garage, computer system, networked device, networked system, home appliance, office equipment, lighting device, robot (e.g. robotic arm), smart vehicle, smart machine, assembly line, smart device, internet-of-thing (IoT) device, smart home device, and/or a smart office device.

The task may include: detect a user returning home, detect a user leaving home, detect a user moving from one room to another, detect/control/lock/unlock/open/close/partially open a window/door/garage door/blind/curtain/panel/solar panel/sun shade, detect a pet, detect/monitor a user doing something (e.g. sleeping on sofa, sleeping in bedroom, running on treadmill, cooking, sitting on sofa, watching TV, eating in kitchen, eating in dining room, going upstairs/downstairs, going outside/coming back, in the rest room), monitor/detect location of a user/pet, do something (e.g. send a message, notify/report to someone) automatically upon detection, do something for the user automatically upon detecting the user, turn on/off/dim a light, turn on/off/music/radio/home entertainment system, turn on/off/adjust/control TV/HiFi/set-top-box (STB)/home entertainment system/smart speaker/smart device, turn on/off/adjust air conditioning system, turn on/off/adjust ventilation system, turn on/off/adjust heating system, adjust/control curtains/light shades, turn on/off/wake a computer, turn on/off/pre-heat/control coffee machine/hot water pot, turn on/off/control/preheat cooker/oven/microwave oven/another cooking device, check/adjust temperature, check weather forecast, check telephone message box, check mail, do a system check, control/adjust a system, check/control/arm/disarm security system/baby monitor, check/control refrigerator, give a report (e.g. through a speaker such as Google home, Amazon Echo, on a display/screen, via a webpage/email/messaging system/notification system).

For example, when a user arrives home in his car, the task may be to, automatically, detect the user or his car approaching, open the garage door upon detection, turn on the driveway/garage light as the user approaches the garage, turn on air conditioner/heater/fan, etc. As the user enters the house, the task may be to, automatically, turn on the entrance light, turn off driveway/garage light, play a greeting message to welcome the user, turn on the music, turn on the radio and tuning to the user's favorite radio news channel, open the curtain/blind, monitor the user's mood, adjust the lighting and sound environment according to the user's mood or the current/imminent event (e.g. do romantic lighting and music because the user is scheduled to eat dinner with girlfriend in 1 hour) on the user's daily calendar, warm the food in microwave that the user prepared in the morning, do a diagnostic check of all systems in the house, check weather forecast for tomorrow's work, check news of interest to the user, check user's calendar and to-do list and play reminder, check telephone answer system/messaging system/email and give a verbal report using dialog system/speech synthesis, remind (e.g. using audible tool such as speakers/HiFi/speech synthesis/sound/voice/music/song/sound field/background sound field/dialog system, using visual tool such as TV/entertainment system/computer/notebook/smart pad/display/light/color/brightness/patterns/symbols, using haptic tool/virtual reality tool/gesture/tool, using a smart device/appliance/material/furniture/fixture, using web tool/server/hub device/cloud server/fog server/edge server/home network/mesh network, using messaging tool/notification tool/communication tool/scheduling tool/email, using user interface/GUI, using scent/smell/fragrance/taste, using neural tool/nervous system tool, using a combination) the user of his mother's birthday and to call her, prepare a report, and give the report (e.g. using a tool for reminding as discussed above). The task may turn on the air conditioner/heater/ventilation system in advance, or adjust temperature setting of smart thermostat in advance, etc. As the user moves from the entrance to the living room, the task may be to turn on the living room light, open the living room curtain, open the window, turn off the entrance light behind the user, turn on the TV and set-top box, set TV to the user's favorite channel, adjust an appliance according to the user's preference and conditions/states (e.g. adjust lighting and choose/play music to build a romantic atmosphere), etc.

Another example may be: When the user wakes up in the morning, the task may be to detect the user moving around in the bedroom, open the blind/curtain, open the window, turn off the alarm clock, adjust indoor temperature from night-time temperature profile to day-time temperature profile, turn on the bedroom light, turn on the restroom light as the user approaches the restroom, check radio or streaming channel and play morning news, turn on the coffee machine and preheat the water, turn off security system, etc. When the user walks from bedroom to kitchen, the task may be to turn on the kitchen and hallway lights, turn off the bedroom and restroom lights, move the music/message/reminder from the bedroom to the kitchen, turn on the kitchen TV, change TV to morning news channel, lower the kitchen blind and open the kitchen window to bring in fresh air, unlock backdoor for the user to check the backyard, adjust temperature setting for the kitchen, etc. Another example may be: When the user leaves home for work, the task may be to detect the user leaving, play a farewell and/or have-a-good-day message, open/close garage door, turn on/off garage light and driveway light, turn off/dim lights to save energy (just in case the user forgets), close/lock all windows/doors (just in case the user forgets), turn off appliance (especially stove, oven, microwave oven), turn on/arm the home security system to guard the home against any intruder, adjust air conditioning/heating/ventilation systems to "away-from-home" profile to save energy, send alerts/reports/updates to the user's smart phone, etc.

A motion may comprise at least one of; a no-motion, resting motion, non-moving motion, movement, change in position/location, deterministic motion, transient motion, fall-down motion, repeating motion, periodic motion, pseudo-periodic motion, periodic/repeated motion associated with breathing, periodic/repeated motion associated with heartbeat, periodic/repeated motion associated with living object, periodic/repeated motion associated with machine, periodic/repeated motion associated with man-made object, periodic/repeated motion associated with nature, complex motion with transient element and periodic element, repetitive motion, non-deterministic motion, probabilistic motion, chaotic motion, random motion, complex motion with non-deterministic element and deterministic element, stationary random motion, pseudo-stationary random motion, cyclo-stationary random motion, non-stationary random motion, stationary random motion with periodic autocorrelation function (ACF), random motion with periodic ACF for period of time, random motion that is pseudo-stationary for a period of time, random motion of which an instantaneous ACF has a pseudo-periodic/repeating element for a period of time, machine motion, mechanical motion, vehicle motion, drone motion, air-related motion, wind-related motion, weather-related motion, water-related motion, fluid-related motion, ground-related motion, change in electro-magnetic characteristics, sub-surface motion, seismic motion, plant motion, animal motion, human motion, normal motion, abnormal motion, dangerous motion, warning motion, suspicious motion, rain, fire, flood, tsunami, explosion, collision, imminent collision, human body motion, head motion, facial motion, eye motion, mouth motion, tongue motion, neck motion, finger motion, hand motion, arm motion, shoulder motion, body motion, chest motion, abdominal motion, hip motion, leg motion, foot motion, body joint motion, knee motion, elbow motion, upper body motion, lower body motion, skin motion, below-skin motion, subcutaneous tissue motion, blood vessel motion, intravenous motion, organ motion, heart motion, lung motion, stomach motion, intestine motion, bowel motion, eating motion, breathing motion, facial expression, eye expression, mouth expression, talking motion, singing motion, eating motion, gesture, hand gesture, arm gesture, keystroke, typing stroke, user-interface gesture, man-machine interaction, gait, dancing movement, coordinated movement, and/or coordinated body movement.

The heterogeneous IC of the Type 1 device and/or any Type 2 receiver may comprise low-noise amplifier (LNA), power amplifier, transmit-receive switch, media access controller, baseband radio, 2.4 GHz radio, 3.65 GHz radio, 4.9 GHz radio, 5 GHz radio, 5.9 GHz radio, below 6 GHz radio, below 60 GHz radio and/or another radio. The heterogeneous IC may comprise a processor, a memory communicatively coupled with the processor, and a set of instructions stored in the memory to be executed by the processor. The IC and/or any processor may comprise at least one of general purpose processor, special purpose processor, microprocessor, multi-processor, multi-core processor, parallel processor, CISC processor, RISC processor, microcontroller, central processing unit (CPU), graphical processor unit (GPU), digital signal processor (DSP), application specific integrated circuit (ASIC), field programmable gate array (FPGA), embedded processor (e.g. ARM), logic circuit, other programmable logic device, discrete logic, and/or a combination. The heterogeneous IC may support broadband network, wireless network, mobile network, mesh network, cellular network, wireless local area network (WLAN), wide area network (WAN), and metropolitan area network (MAN), WLAN standard, WiFi, LTE, LTE-A, LTE-U, 802.11 standard, 802.11a, 802.11b, 802.11g, 802.11n, 802.11ac, 802.11ad, 802.11af, 802.11ah, 802.11ax, 802.11ay, mesh network standard, 802.15 standard, 802.16 standard, cellular network standard, 3G, 3.5G, 4G, beyond 4G, 4.5G, 5G, 6G, 7G, 8G, 9G, UMTS, 3GPP, GSM, EDGE, TDMA, FDMA, CDMA, WCDMA, TD-SCDMA, Bluetooth, Bluetooth Low-Energy (BLE), NFC, Zigbee, WiMax, and/or another wireless network protocol.

The processor may comprise general purpose processor, special purpose processor, microprocessor, microcontroller, embedded processor, digital signal processor, central processing unit (CPU), graphical processing unit (GPU), multi-processor, multi-core processor, and/or processor with graphics capability, and/or a combination. The memory may be volatile, non-volatile, random access memory (RAM), Read Only Memory (ROM), Electrically Programmable ROM (EPROM), Electrically Erasable Programmable ROM (EEPROM), hard disk, flash memory, CD-ROM, DVD-ROM, magnetic storage, optical storage, organic storage, storage system, storage network, network storage, cloud storage, edge storage, local storage, external storage, internal storage, or other form of non-transitory storage medium known in the art. The set of instructions (machine executable code) corresponding to the method steps may be embodied directly in hardware, in software, in firmware, or in combinations thereof. The set of instructions may be embedded, pre-loaded, loaded upon boot up, loaded on the fly, loaded on demand, pre-installed, installed, and/or downloaded.

The presentation may be a presentation in an audio-visual way (e.g. using combination of visual, graphics, text, symbols, color, shades, video, animation, sound, speech, audio, etc.), graphical way (e.g. using GUI, animation, video), textual way (e.g. webpage with text, message, animated text), symbolic way (e.g. emoticon, signs, hand gesture), or mechanical way (e.g. vibration, actuator movement, haptics, etc.).

Computational workload associated with the method is shared among the processor, the Type 1 heterogeneous wireless device, the Type 2 heterogeneous wireless device, a local server (e.g. hub device), a cloud server, and another processor.

An operation, pre-processing, processing and/or postprocessing may be applied to data (e.g. TSCI, autocorrelation, features of TSCI). An operation may be preprocessing, processing and/or postprocessing. The preprocessing, processing and/or postprocessing may be an operation. An operation may comprise preprocessing, processing, postprocessing, scaling, computing a confidence factor, computing a line-of-sight (LOS) quantity, computing a non-LOS (NLOS) quantity, a quantity comprising LOS and NLOS, computing a single link (e.g. path, communication path, link between a transmitting antenna and a receiving antenna) quantity, computing a quantity comprising multiple links, computing a function of the operands, filtering, linear filtering, nonlinear filtering, folding, grouping, energy computation, lowpass filtering, bandpass filtering, highpass filtering, median filtering, rank filtering, quartile filtering, percentile filtering, mode filtering, finite impulse response (FIR) filtering, infinite impulse response (IIR) filtering, moving average (MA) filtering, autoregressive (AR) filtering, autoregressive moving averaging (ARMA) filtering, selective filtering, adaptive filtering, interpolation, decimation, subsampling, upsampling, resampling, time correction, time base correction, phase correction, magnitude correction, phase cleaning, magnitude cleaning, matched filtering, enhancement, restoration, denoising, smoothing, signal conditioning, enhancement, restoration, spectral analysis, linear transform, nonlinear transform, inverse transform, frequency transform, inverse frequency transform, Fourier transform (FT), discrete time FT (DTFT), discrete FT (DFT), fast FT (FFT), wavelet transform, Laplace transform, Hilbert transform, Hadamard transform, trigonometric transform, sine transform, cosine transform, DCT, power-of-2 transform, sparse transform, graph-based transform, graph signal processing, fast transform, a transform combined with zero padding, cyclic padding, padding, zero padding, feature extraction, decomposition, projection, orthogonal projection, non-orthogonal projection, over-complete projection, eigen-decomposition, singular value decomposition (SVD), principle component analysis (PCA), independent component analysis (ICA), grouping, sorting, thresholding, soft thresholding, hard thresholding, clipping, soft clipping, first derivative, second order derivative, high order derivative, convolution, multiplication, division, addition, subtraction, integration, maximization, minimization, least mean square error, recursive least square, constrained least square, batch least square, least absolute error, least mean square deviation, least absolute deviation, local maximization, local minimization, optimization of a cost function, neural network, recognition, labeling, training, clustering, machine learning, supervised learning, unsupervised learning, semi-supervised learning, comparison with another TSCI, similarity score computation, quantization, vector quantization, matching pursuit, compression, encryption, coding, storing, transmitting, normalization, temporal normalization, frequency domain normalization, classification, clustering, labeling, tagging, learning, detection, estimation, learning network, mapping, remapping, expansion, storing, retrieving, transmitting, receiving, representing, merging, combining, splitting, tracking, monitoring, matched filtering, Kalman filtering, particle filter, intrapolation, extrapolation, histogram estimation, importance sampling, Monte Carlo sampling, compressive sensing, representing, merging, combining, splitting, scrambling, error protection, forward error correction, doing nothing, time varying processing, conditioning averaging, weighted averaging, arithmetic mean, geometric mean, harmonic mean, averaging over selected frequency, averaging over antenna links, logical operation, permutation, combination, sorting, AND, OR, XOR, union, intersection, vector addition, vector subtraction, vector multiplication, vector division, inverse, norm, distance, and/or another operation. The operation may be the preprocessing, processing, and/or post-processing. Operations may be applied jointly on multiple time series or functions.

The function (e.g. function of operands) may comprise: scalar function, vector function, discrete function, continuous function, polynomial function, characteristics, feature, magnitude, phase, exponential function, logarithmic function, trigonometric function, transcendental function, logical function, linear function, algebraic function, nonlinear function, piecewise linear function, real function, complex function, vector-valued function, inverse function, derivative of function, integration of function, circular function, function of another function, one-to-one function, one-to-many function, many-to-one function, many-to-many function, zero crossing, absolute function, indicator function, mean, mode, median, range, statistics, histogram, variance, standard deviation, measure of variation, spread, dispersion, deviation, divergence, range, interquartile range, total variation, absolute deviation, total deviation, arithmetic mean, geometric mean, harmonic mean, trimmed mean, percentile, square, cube, root, power, sine, cosine, tangent, cotangent, secant, cosecant, elliptical function, parabolic function, hyperbolic function, game function, zeta function, absolute value, thresholding, limiting function, floor function, rounding function, sign function, quantization, piecewise constant function, composite function, function of function, time function processed with an operation (e.g. filtering), probabilistic function, stochastic function, random function, ergodic function, stationary function, deterministic function, periodic function, repeated function, transformation, frequency transform, inverse frequency transform, discrete time transform, Laplace transform, Hilbert transform, sine transform, cosine transform, triangular transform, wavelet transform, integer transform, power-of-2 transform, sparse transform, projection, decomposition, principle component analysis (PCA), independent component analysis (ICA), neural network, feature extraction, moving function, function of moving window of neighboring items of time series, filtering function, convolution, mean function, histogram, variance/standard deviation function, statistical function, short-time transform, discrete transform, discrete Fourier transform, discrete cosine transform, discrete sine transform, Hadamard transform, eigen-decomposition, eigenvalue, singular value decomposition (SVD), singular value, orthogonal decomposition, matching pursuit, sparse transform, sparse approximation, any decomposition, graph-based processing, graph-based transform, graph signal processing, classification, identifying a class/group/category, labeling, learning, machine learning, detection, estimation, feature extraction, learning network, feature extraction, denoising, signal enhancement, coding, encryption, mapping, remapping, vector quantization, lowpass filtering, highpass filtering, bandpass filtering, matched filtering, Kalman filtering, preprocessing, postprocessing, particle filter, FIR filtering, HR filtering, autoregressive (AR) filtering, adaptive filtering, first order derivative, high order derivative, integration, zero crossing, smoothing, median filtering, mode filtering, sampling, random sampling, resampling function, downsampling, down-converting, upsampling, up-converting, interpolation, extrapolation, importance sampling, Monte Carlo sampling, compressive sensing, statistics, short term statistics, long term statistics, autocorrelation function, cross correlation, moment generating function, time averaging, weighted averaging, special function, Bessel function, error function, complementary error function, Beta function, Gamma function, integral function, Gaussian function, Poisson function, etc. Machine learning, training, discriminative training, deep learning, neural network, continuous time processing, distributed computing, distributed storage, acceleration using GPU/DSP/coprocessor/multicore/multi-processing may be applied to a step (or each step) of this disclosure.

A frequency transform may include Fourier transform, Laplace transform, Hadamard transform, Hilbert transform, sine transform, cosine transform, triangular transform, wavelet transform, integer transform, power-of-2 transform, combined zero padding and transform, Fourier transform with zero padding, and/or another transform. Fast versions and/or approximated versions of the transform may be performed. The transform may be performed using floating point, and/or fixed point arithmetic.

An inverse frequency transform may include inverse Fourier transform, inverse Laplace transform, inverse Hadamard transform, inverse Hilbert transform, inverse sine transform, inverse cosine transform, inverse triangular transform, inverse wavelet transform, inverse integer transform, inverse power-of-2 transform, combined zero padding and transform, inverse Fourier transform with zero padding, and/or another transform. Fast versions and/or approximated versions of the transform may be performed. The transform may be performed using floating point, and/or fixed point arithmetic.

A quantity/feature from a TSCI may be computed. The quantity may comprise statistic of at least one of: motion, location, map coordinate, height, speed, acceleration, movement angle, rotation, size, volume, time trend, pattern, one-time pattern, repeating pattern, evolving pattern, time pattern, mutually excluding patterns, related/correlated patterns, cause-and-effect, correlation, short-term/long-term correlation, tendency, inclination, statistics, typical behavior, atypical behavior, time trend, time profile, periodic motion, repeated motion, repetition, tendency, change, abrupt change, gradual change, frequency, transient, breathing, gait, action, event, suspicious event, dangerous event, alarming event, warning, belief, proximity, collision, power, signal, signal power, signal strength, signal intensity, received signal strength indicator (RSSI), signal amplitude, signal phase, signal frequency component, signal frequency band component, channel state information (CSI), map, time, frequency, time-frequency, decomposition, orthogonal decomposition, non-orthogonal decomposition, tracking, breathing, heart beat, statistical parameters, cardiopulmonary statistics/analytics (e.g. output responses), daily activity statistics/analytics, chronic disease statistics/analytics, medical statistics/analytics, an early (or instantaneous or contemporaneous or delayed) indication/suggestion/sign/indicator/verifier/detection/symptom of a disease/condition/situation, biometric, baby, patient, machine, device, temperature, vehicle, parking lot, venue, lift, elevator, spatial, road, fluid flow, home, room, office, house, building, warehouse, storage, system, ventilation, fan, pipe, duct, people, human, car, boat, truck, airplane, drone, downtown, crowd, impulsive event, cyclo-stationary, environment, vibration, material, surface, 3-dimensional, 2-dimensional, local, global, presence, and/or another measurable quantity/variable.

Sliding time window may have time varying window width. It may be smaller at the beginning to enable fast acquisition and may increase over time to a steady-state size. The steady-state size may be related to the frequency, repeated motion, transient motion, and/or STI to be monitored. Even in steady state, the window size may be adaptively (and/or dynamically) changed (e.g. adjusted, varied, modified) based on battery life, power consumption, available computing power, change in amount of targets, the nature of motion to be monitored, etc.

The time shift between two sliding time windows at adjacent time instance may be constant/variable/locally adaptive/dynamically adjusted over time. When shorter time shift is used, the update of any monitoring may be more frequent which may be used for fast changing situations, object motions, and/or objects. Longer time shift may be used for slower situations, object motions, and/or objects. The window width/size and/or time shift may be changed (e.g. adjusted, varied, modified) upon a user request/choice. The time shift may be changed automatically (e.g. as controlled by processor/computer/server/hub device/cloud server) and/or adaptively (and/or dynamically).

At least one characteristics (e.g. characteristic value, or characteristic point) of a function (e.g. auto-correlation function, auto-covariance function, cross-correlation function, cross-covariance function, power spectral density, time function, frequency domain function, frequency transform) may be determined (e.g. by an object tracking server, the processor, the Type 1 heterogeneous device, the Type 2 heterogeneous device, and/or another device). The at least one characteristics of the function may include: a maximum, minimum, extremum, local maximum, local minimum, local extremum, local extremum with positive time offset, first local extremum with positive time offset, n^th local extremum with positive time offset, local extremum with negative time offset, first local extremum with negative time offset, n^th local extremum with negative time offset, constrained maximum, constrained minimum, constrained extremum, significant maximum, significant minimum, significant extremum, slope, derivative, higher order derivative, maximum slope, minimum slope, local maximum slope, local maximum slope with positive time offset, local minimum slope, constrained maximum slope, constrained minimum slope, maximum higher order derivative, minimum higher order derivative, constrained higher order derivative, zero-crossing, zero crossing with positive time offset, n^th zero crossing with positive time offset, zero crossing with negative time offset, n^th zero crossing with negative time offset, constrained zero-crossing, zero-crossing of slope, zero-crossing of higher order derivative, and/or another characteristics. At least one argument of the function associated with the at least one characteristics of the function may be identified. Some quantity (e.g. spatial-temporal information of the object) may be determined based on the at least one argument of the function.

A characteristics (e.g. characteristics of motion of an object in the venue) may comprise at least one of: an instantaneous characteristics, short-term characteristics, repetitive characteristics, recurring characteristics, history, incremental characteristics, changing characteristics, deviational characteristics, phase, magnitude, degree, time characteristics, frequency characteristics, time-frequency characteristics, decomposition characteristics, orthogonal decomposition characteristics, non-orthogonal decomposition characteristics, deterministic characteristics, probabilistic characteristics, stochastic characteristics, autocorrelation function (ACF), mean, variance, standard deviation, measure of variation, spread, dispersion, deviation, divergence, range, interquartile range, total variation, absolute deviation, total deviation, statistics, duration, timing, trend, periodic characteristics, repetition characteristics, long-term characteristics, historical characteristics, average characteristics, current characteristics, past characteristics, future characteristics, predicted characteristics, location, distance, height, speed, direction, velocity, acceleration, change of the acceleration, angle, angular speed, angular velocity, angular acceleration of the object, change of the angular acceleration, orientation of the object, angular of rotation, deformation of the object, shape of the object, change of shape of the object, change of size of the object, change of structure of the object, and/or change of characteristics of the object.

At least one local maximum and at least one local minimum of the function may be identified. At least one local signal-to-noise-ratio-like (SNR-like) parameter may be computed for each pair of adjacent local maximum and local minimum. The SNR-like parameter may be a function (e.g. linear, log, exponential function, monotonic function) of a fraction of a quantity (e.g. power, magnitude) of the local maximum over the same quantity of the local minimum. It may also be the function of a difference between the quantity of the local maximum and the same quantity of the local minimum. Significant local peaks may be identified or selected. Each significant local peak may be a local maximum with SNR-like parameter greater than a threshold T1 and/or a local maximum with amplitude greater than a threshold T2. The at least one local minimum and the at least one local minimum in the frequency domain may be identified/computed using a persistence-based approach.

A set of selected significant local peaks may be selected from the set of identified significant local peaks based on a selection criterion (e.g. a quality criterion, a signal quality condition). The characteristics/STI of the object may be computed based on the set of selected significant local peaks and frequency values associated with the set of selected significant local peaks. In one example, the selection criterion may always correspond to select the strongest peaks in a range. While the strongest peaks may be selected, the unselected peaks may still be significant (rather strong).

Unselected significant peaks may be stored and/or monitored as "reserved" peaks for use in future selection in future sliding time windows. As an example, there may be a particular peak (at a particular frequency) appearing consistently over time. Initially, it may be significant but not selected (as other peaks may be stronger). But in later time, the peak may become stronger and more dominant and may be selected. When it became "selected", it may be back-traced in time and made "selected" in the earlier time when it was significant but not selected. In such case, the back-traced peak may replace a previously selected peak in an early time. The replaced peak may be the relatively weakest, or a peak that appear in isolation in time (i.e. appearing only briefly in time).

In another example, the selection criterion may not correspond to select the strongest peaks in the range. Instead, it may consider not only the "strength" of the peak, but the "trace" of the peak—peaks that may have happened in the past, especially those peaks that have been identified for a long time. For example, if a finite state machine (FSM) is used, it may select the peak(s) based on the state of the FSM. Decision thresholds may be computed adaptively (and/or dynamically) based on the state of the FSM.

A similarity score and/or component similarity score may be computed (e.g. by a server (e.g. hub device), the processor, the Type 1 device, the Type 2 device, a local server, a cloud server, and/or another device) based on a pair of temporally adjacent CI of a TSCI. The pair may come from the same sliding window or two different sliding windows. The similarity score may also be based on a pair of, temporally adjacent or not so adjacent, CI from two different TSCI. The similarity score and/or component similar score may be/comprise: time reversal resonating strength (TRRS), correlation, cross-correlation, auto-correlation, correlation indicator, covariance, cross-covariance, auto-covariance, inner product of two vectors, distance score, norm, metric, quality metric, signal quality condition, statistical characteristics, discrimination score, neural network, deep learning network, machine learning, training, discrimination, weighted averaging, preprocessing, denoising, signal conditioning, filtering, time correction, timing compensation, phase offset compensation, transformation, component-wise operation, feature extraction, finite state machine, and/or another score. The characteristics and/or STI may be determined/computed based on the similarity score.

Any threshold may be pre-determined, adaptively (and/or dynamically) determined and/or determined by a finite state machine. The adaptive determination may be based on time, space, location, antenna, path, link, state, battery life, remaining battery life, available power, available computational resources, available network bandwidth, etc.

A threshold to be applied to a test statistics to differentiate two events (or two conditions, or two situations, or two states), A and B, may be determined. Data (e.g. CI, channel state information (CSI), power parameter) may be collected under A and/or under B in a training situation. The test statistics may be computed based on the data. Distributions of the test statistics under A may be compared with distributions of the test statistics under B (reference distribution), and the threshold may be chosen according to some criteria. The criteria may comprise: maximum likelihood (ML), maximum aposterior probability (MAP), discriminative training, minimum Type 1 error for a given Type 2 error, minimum Type 2 error for a given Type 1 error, and/or other criteria (e.g. a quality criterion, signal quality condition). The threshold may be adjusted to achieve different sensitivity to the A, B and/or another event/condition/situation/state. The threshold adjustment may be automatic, semi-automatic and/or manual. The threshold adjustment may be applied once, sometimes, often, periodically, repeatedly, occasionally, sporadically, and/or on demand. The threshold adjustment may be adaptive (and/or dynamically adjusted). The threshold adjustment may depend on the object, object movement/location/direction/action, object characteristics/STI/size/property/trait/habit/behavior, the venue, feature/fixture/furniture/barrier/material/machine/living thing/thing/object/boundary/surface/medium that is in/at/of the venue, map, constraint of the map (or environmental model), the event/state/situation/condition, time, timing, duration, current state, past history, user, and/or a personal preference, etc.

A stopping criterion (or skipping or bypassing or blocking or pausing or passing or rejecting criterion) of an iterative algorithm may be that change of a current parameter (e.g. offset value) in the updating in an iteration is less than a threshold. The threshold may be 0.5, 1, 1.5, 2, or another number. The threshold may be adaptive (and/or dynamically adjusted). It may change as the iteration progresses. For the offset value, the adaptive threshold may be determined based on the task, particular value of the first time, the current time offset value, the regression window, the regression analysis, the regression function, the regression error, the convexity of the regression function, and/or an iteration number.

The local extremum may be determined as the corresponding extremum of the regression function in the regression window. The local extremum may be determined based on a set of time offset values in the regression window and a set of associated regression function values. Each of the set of associated regression function values associated with the set of time offset values may be within a range from the corresponding extremum of the regression function in the regression window.

The searching for a local extremum may comprise robust search, minimization, maximization, optimization, statistical optimization, dual optimization, constraint optimization, convex optimization, global optimization, local optimization an energy minimization, linear regression, quadratic regression, higher order regression, linear programming, nonlinear programming, stochastic programming, combinatorial optimization, constraint programming, constraint satisfaction, calculus of variations, optimal control, dynamic programming, mathematical programming, multi-objective optimization, multi-modal optimization, disjunctive programming, space mapping, infinite-dimensional optimization, heuristics, metaheuristics, convex programming, semidefinite programming, conic programming, cone programming, integer programming, quadratic programming, fractional programming, numerical analysis, simplex algorithm, iterative method, gradient descent, subgradient method, coordinate descent, conjugate gradient method, Newton's algorithm, sequential quadratic programming, interior point method, ellipsoid method, reduced gradient method, quasi-Newton method, simultaneous perturbation stochastic approximation, interpolation method, pattern search method, line search, non-differentiable optimization, genetic algorithm, evolutionary algorithm, dynamic relaxation, hill climbing, particle swarm optimization, gravitation search algorithm, simulated annealing, memetic algorithm, differential evolution, dynamic relaxation, stochastic tunneling, Tabu search, reactive search optimization, curve fitting, least square, simulation based optimization, variational calculus, and/or variant. The search for local extremum may be associated with an objective function, loss function, cost function, utility function, fitness function, energy function, and/or an energy function.

Regression may be performed using regression function to fit sampled data (e.g. CI, feature of CI, component of CI) or another function (e.g. autocorrelation function) in a regression window. In at least one iteration, a length of the regression window and/or a location of the regression window may change. The regression function may be linear function, quadratic function, cubic function, polynomial function, and/or another function. The regression analysis may minimize at least one of error, aggregate error, component error, error in projection domain, error in selected axes, error in selected orthogonal axes, absolute error, square error, absolute deviation, square deviation, higher order error (e.g. third order, fourth order), robust error (e.g. square error for smaller error magnitude and absolute error for larger error magnitude, or first kind of error for smaller error magnitude and second kind of error for larger error magnitude), another error, weighted sum (or weighted mean) of absolute/square error (e.g. for wireless transmitter with multiple antennas and wireless receiver with multiple antennas, each pair of transmitter antenna and receiver antenna form a link), mean absolute error, mean square error, mean absolute deviation, and/or mean square deviation. Error associated with different links may have different weights. One possibility is that some links and/or some components with larger noise or lower signal quality metric may have smaller or bigger weight.), weighted sum of square error, weighted sum of higher order error, weighted sum of robust error, weighted sum of the another error, absolute cost, square cost, higher order cost, robust cost, another cost, weighted sum of absolute cost, weighted sum of square cost, weighted sum of higher order cost, weighted sum of robust cost, and/or weighted sum of another cost. The regression error determined may be an absolute error, square error, higher order error, robust error, yet another error, weighted sum of absolute error, weighted sum of square error, weighted sum of higher order error, weighted sum of robust error, and/or weighted sum of the yet another error.

The time offset associated with maximum regression error (or minimum regression error) of the regression function with respect to the particular function in the regression window may become the updated current time offset in the iteration.

A local extremum may be searched based on a quantity comprising a difference of two different errors (e.g. a difference between absolute error and square error). Each of the two different errors may comprise an absolute error, square error, higher order error, robust error, another error, weighted sum of absolute error, weighted sum of square error, weighted sum of higher order error, weighted sum of robust error, and/or weighted sum of the another error.

The quantity may be compared with a reference data or a reference distribution, such as an F-distribution, central F-distribution, another statistical distribution, threshold, threshold associated with probability/histogram, threshold associated with probability/histogram of finding false peak, threshold associated with the F-distribution, threshold associated the central F-distribution, and/or threshold associated with the another statistical distribution.

The regression window may be determined based on at least one of: the movement (e.g. change in position/location) of the object, quantity associated with the object, the at least one characteristics and/or STI of the object associated with the movement of the object, estimated location of the local extremum, noise characteristics, estimated noise characteristics, signal quality metric, F-distribution, central F-distribution, another statistical distribution, threshold, preset threshold, threshold associated with probability/histogram, threshold associated with desired probability, threshold associated with probability of finding false peak, threshold associated with the F-distribution, threshold associated the central F-distribution, threshold associated with the another statistical distribution, condition that quantity at the window center is largest within the regression window, condition that the quantity at the window center is largest within the regression window, condition that there is only one of the local extremum of the particular function for the particular value of the first time in the regression window, another regression window, and/or another condition.

The width of the regression window may be determined based on the particular local extremum to be searched. The local extremum may comprise first local maximum, second local maximum, higher order local maximum, first local maximum with positive time offset value, second local maximum with positive time offset value, higher local maximum with positive time offset value, first local maximum with negative time offset value, second local maximum with negative time offset value, higher local maximum with negative time offset value, first local minimum, second local minimum, higher local minimum, first local minimum with positive time offset value, second local minimum with positive time offset value, higher local minimum with positive time offset value, first local minimum with negative time offset value, second local minimum with negative time offset value, higher local minimum with negative time offset value, first local extremum, second local extremum, higher local extremum, first local extremum with positive time offset value, second local extremum with positive time offset value, higher local extremum with positive time offset value, first local extremum with negative time offset value, second local extremum with negative time offset value, and/or higher local extremum with negative time offset value.

A current parameter (e.g. time offset value) may be initialized based on a target value, target profile, trend, past trend, current trend, target speed, speed profile, target speed profile, past speed trend, the motion or movement (e.g. change in position/location) of the object, at least one characteristics and/or STI of the object associated with the movement of object, positional quantity of the object, initial speed of the object associated with the movement of the object, predefined value, initial width of the regression window, time duration, value based on carrier frequency of the signal, value based on subcarrier frequency of the signal, bandwidth of the signal, amount of antennas associated with the channel, noise characteristics, signal h metric, and/or an adaptive (and/or dynamically adjusted) value. The current time offset may be at the center, on the left side, on the right side, and/or at another fixed relative location, of the regression window.

In the presentation, information may be displayed with a map (or environmental model) of the venue. The information may comprise: location, zone, region, area, coverage area, corrected location, approximate location, location with respect to (w.r.t.) a map of the venue, location w.r.t. a segmentation of the venue, direction, path, path w.r.t. the map and/or the segmentation, trace (e.g. location within a time window such as the past 5 seconds, or past 10 seconds; the time window duration may be adjusted adaptively (and/or dynamically); the time window duration may be adaptively (and/or dynamically) adjusted w.r.t. speed, acceleration, etc.), history of a path, approximate regions/zones along a path, history/summary of past locations, history of past locations of interest, frequently-visited areas, customer traffic, crowd distribution, crowd behavior, crowd control information, speed, acceleration, motion statistics, breathing rate, heart rate, presence/absence of motion, presence/absence of people or pets or object, presence/absence of vital sign, gesture, gesture control (control of devices using gesture), location-based gesture control, information of a location-based operation, identity (ID) or identifier of the respect object (e.g. pet, person, self-guided machine/device, vehicle, drone, car, boat, bicycle, self-guided vehicle, machine with fan, air-conditioner, TV, machine with movable part), identification of a user (e.g. person), information of the user, location/speed/acceleration/direction/motion/gesture/gesture control/motion trace of the user, ID or identifier of the user, activity of the user, state of the user, sleeping/resting characteristics of the user, emotional state of the user, vital sign of the user, environment information of the venue, weather information of the venue, earthquake, explosion, storm, rain, fire, temperature, collision, impact, vibration, event, door-open event, door-close event, window-open event, window-close event, fall-down event, burning event, freezing event, water-related event, wind-related event, air-movement event, accident event, pseudo-periodic event (e.g. running on treadmill, jumping up and down, skipping rope, somersault, etc.), repeated event, crowd event, vehicle event, gesture of the user (e.g. hand gesture, arm gesture, foot gesture, leg gesture, body gesture, head gesture, face gesture, mouth gesture, eye gesture, etc.). The location may be 2-dimensional (e.g. with 2D coordinates), 3-dimensional (e.g. with 3D coordinates). The location may be relative (e.g. w.r.t. a map or environmental model) or relational (e.g. halfway between point A and point B, around a corner, up the stairs, on top of table, at the ceiling, on the floor, on a sofa, close to point A, a distance R from point A, within a radius of R from point A, etc.). The location may be expressed in rectangular coordinate, polar coordinate, and/or another representation.

The information (e.g. location) may be marked with at least one symbol. The symbol may be time varying. The symbol may be flashing and/or pulsating with or without changing color/intensity. The size may change over time. The orientation of the symbol may change over time. The symbol may be a number that reflects an instantaneous quantity (e.g. vital sign/breathing rate/heart rate/gesture/state/status/action/motion of a user, temperature, network traffic, network connectivity, status of a device/machine, remaining power of a device, status of the device, etc.). The rate of change, the size, the orientation, the color, the intensity and/or the symbol may reflect the respective motion. The information may be disclosed visually and/or described verbally (e.g. using pre-recorded voice, or voice synthesis). The information may be described in text. The information may also be disclosed in a mechanical way (e.g. an animated gadget, a movement of a movable part).

The user-interface (UI) device may be a smart phone (e.g. iPhone, Android phone), tablet (e.g. iPad), laptop (e.g. notebook computer), personal computer (PC), device with graphical user interface (GUT), smart speaker, device with voice/audio/speaker capability, virtual reality (VR) device, augmented reality (AR) device, smart car, display in the car, voice assistant, voice assistant in a car, etc. The map (or environmental model) may be 2-dimensional, 3-dimensional and/or higher-dimensional. (e.g. a time varying 2D/3D map/environmental model) Walls, windows, doors, entrances, exits, forbidden areas may be marked on the map or the model. The map may comprise floor plan of a facility. The map or model may have one or more layers (overlays). The map/model may be a maintenance map/model comprising water pipes, gas pipes, wiring, cabling, air ducts, crawl-space, ceiling layout, and/or underground layout. The venue may be segmented/subdivided/zoned/grouped into multiple zones/regions/geographic regions/sectors/sections/territories/districts/precincts/localities/neighborhoods/areas/stretches/expanse such as bedroom, living room, storage room, walkway, kitchen, dining room, foyer, garage, first floor, second floor, rest room, offices, conference room, reception area, various office areas, various warehouse regions, various facility areas, etc. The segments/regions/areas may be disclosed in a map/model. Different regions may be color-coded. Different regions may be disclosed with a characteristic (e.g. color, brightness, color intensity, texture, animation, flashing, flashing rate, etc.). Logical segmentation of the venue may be done using the at least one heterogeneous Type 2 device, or a server (e.g. hub device), or a cloud server, etc.

Here is an example of the disclosed system, apparatus, and method. Stephen and his family want to install the disclosed wireless motion detection system to detect motion in their 2000 sqft two-storey town house in Seattle, Wash. Because his house has two storeys, Stephen decided to use one Type 2 device (named A) and two Type 1 devices (named B and C) in the ground floor. His ground floor has predominantly three rooms: kitchen, dining room and living room arranged in a straight line, with the dining room in the middle. The kitchen and the living rooms are on opposite end of the house. He put the Type 2 device (A) in the dining room, and put one Type 1 device (B) in the kitchen and the other Type 1 device (C) in the living room. With this placement of the devices, he is practically partitioning the ground floor into 3 zones (dining room, living room and kitchen) using the motion detection system. When motion is detected by the AB pair and the AC pair, the system would analyze the motion information and associate the motion with one of the 3 zones.

When Stephen and his family go out on weekends (e.g. to go for a camp during a long weekend), Stephen would use a mobile phone app (e.g. Android phone app or iPhone app) to turn on the motion detection system. When the system detects motion, a warning signal is sent to Stephen (e.g. an SMS text message, an email, a push message to the mobile phone app, etc.). If Stephen pays a monthly fee (e.g. $10/month), a service company (e.g. security company) will receive the warning signal through wired network (e.g. broadband) or wireless network (e.g. home WiFi, LTE, 3G, 2.5G, etc.) and perform a security procedure for Stephen (e.g. call him to verify any problem, send someone to check on the house, contact the police on behalf of Stephen, etc.). Stephen loves his aging mother and cares about her well-being when she is alone in the house. When the mother is alone in the house while the rest of the family is out (e.g. go to work, or shopping, or go on vacation), Stephen would turn on the motion detection system using his mobile app to ensure the mother is ok. He then uses the mobile app to monitor his mother's movement in the house. When Stephen uses the mobile app to see that the mother is moving around the house among the 3 regions, according to her daily routine, Stephen knows that his mother is doing ok. Stephen is thankful that the motion detection system can help him monitor his mother's well-being while he is away from the house.

On a typical day, the mother would wake up at around 7 AM. She would cook her breakfast in the kitchen for about 20 minutes. Then she would eat the breakfast in the dining room for about 30 minutes. Then she would do her daily exercise in the living room, before sitting down on the sofa in the living room to watch her favorite TV show. The motion detection system enables Stephen to see the timing of the movement in each of the 3 regions of the house. When the motion agrees with the daily routine, Stephen knows roughly that the mother should be doing fine. But when the motion pattern appears abnormal (e.g. there is no motion until 10 AM, or she stayed in the kitchen for too long, or she remains motionless for too long, etc.), Stephen suspects something is wrong and would call the mother to check on her. Stephen may even get someone (e.g. a family member, a neighbor, a paid personnel, a friend, a social worker, a service provider) to check on his mother.

At some time, Stephen feels like repositioning the Type 2 device. He simply unplugs the device from the original AC power plug and plug it into another AC power plug. He is happy that the wireless motion detection system is plug-and-play and the repositioning does not affect the operation of the system. Upon powering up, it works right away. Sometime later, Stephen is convinced that the disclosed wireless motion detection system can really detect motion with very high accuracy and very low alarm, and he really can use the mobile app to monitor the motion in the ground floor. He decides to install a similar setup (i.e. one Type 2 device and two Type 1 devices) in the second floor to monitor the bedrooms in the second floor. Once again, he finds that the system set up is extremely easy as he simply needs to plug the Type 2 device and the Type 1 devices into the AC power plug in the second floor. No special installation is needed. And he can use the same mobile app to monitor motion in the ground floor and the second floor. Each Type 2 device in the ground floor/second floor can interact with all the Type 1 devices in both the ground floor and the second floor. Stephen is happy to see that, as he doubles his investment in the Type 1 and Type 2 devices, he has more than double the capability of the combined systems.

According to various embodiments, each CI (CI) may comprise at least one of: channel state information (CSI), frequency domain CSI, frequency representation of CSI, frequency domain CSI associated with at least one sub-band, time domain CSI, CSI in domain, channel response, estimated channel response, channel impulse response (CIR), channel frequency response (CFR), channel characteristics, channel filter response, CSI of the wireless multipath channel, information of the wireless multipath channel, timestamp, auxiliary information, data, meta data, user data, account data, access data, security data, session data, status data, supervisory data, household data, identity (ID), identifier, device data, network data, neighborhood data, environment data, real-time data, sensor data, stored data, encrypted data, compressed data, protected data, and/or another CI. In one embodiment, the disclosed system has hardware components (e.g. wireless transmitter/receiver with antenna, analog circuitry, power supply, processor, memory) and corresponding software components. According to various embodiments of the present teaching, the disclosed system includes Bot (referred to as a Type 1 device) and Origin (referred to as a Type 2 device) for vital sign detection and monitoring. Each device comprises a transceiver, a processor and a memory.

The disclosed system can be applied in many cases. In one example, the Type 1 device (transmitter) may be a small WiFi-enabled device resting on the table. It may also be a WiFi-enabled television (TV), set-top box (STB), a smart speaker (e.g. Amazon echo), a smart refrigerator, a smart microwave oven, a mesh network router, a mesh network satellite, a smart phone, a computer, a tablet, a smart plug, etc. In one example, the Type 2 (receiver) may be a WiFi-enabled device resting on the table. It may also be a WiFi-enabled television (TV), set-top box (STB), a smart speaker (e.g. Amazon echo), a smart refrigerator, a smart microwave oven, a mesh network router, a mesh network satellite, a smart phone, a computer, a tablet, a smart plug, etc. The Type 1 device and Type 2 devices may be placed in/near a conference room to count people. The Type 1 device and Type 2 devices may be in a well-being monitoring system for older adults to monitor their daily activities and any sign of symptoms (e.g. dementia, Alzheimer's disease). The Type 1 device and Type 2 device may be used in baby monitors to monitor the vital signs (breathing) of a living baby. The Type 1 device and Type 2 devices may be placed in bedrooms to monitor quality of sleep and any sleep apnea. The Type 1 device and Type 2 devices may be placed in cars to monitor well-being of passengers and driver, detect any sleeping of driver and detect any babies left in a car. The Type 1 device and Type 2 devices may be used in logistics to prevent human trafficking by monitoring any human hidden in trucks and containers. The Type 1 device and Type 2 devices may be deployed by emergency service at disaster area to search for trapped victims in debris. The Type 1 device and Type 2 devices may be deployed in an area to detect breathing of any intruders. There are numerous applications of wireless breathing monitoring without wearables.

Hardware modules may be constructed to contain the Type 1 transceiver and/or the Type 2 transceiver. The hardware modules may be sold to/used by variable brands to design, build and sell final commercial products. Products using the disclosed system and/or method may be home/office security products, sleep monitoring products, WiFi products, mesh products, TV, STB, entertainment system, HiFi, speaker, home appliance, lamps, stoves, oven, microwave oven, table, chair, bed, shelves, tools, utensils, torches, vacuum cleaner, smoke detector, sofa, piano, fan, door, window, door/window handle, locks, smoke detectors, car accessories, computing devices, office devices, air conditioner, heater, pipes, connectors, surveillance camera, access point, computing devices, mobile devices, LTE devices, 3G/4G/5G/6G devices, UMTS devices, 3GPP devices, GSM devices, EDGE devices, TDMA devices, FDMA devices, CDMA devices, WCDMA devices, TD-SCDMA devices, gaming devices, eyeglasses, glass panels, VR goggles, necklace, watch, waist band, belt, wallet, pen, hat, wearables, implantable device, tags, parking tickets, smart phones, etc.

The summary may comprise: analytics, output response, selected time window, subsampling, transform, and/or projection. The presenting may comprise presenting at least one of; monthly/weekly/daily view, simplified/detailed view, cross-sectional view, small/large form-factor view, color-coded view, comparative view, summary view, animation, web view, voice announcement, and another presentation related to the periodic/repetition characteristics of the repeating motion.

A Type 1/Type 2 device may be an antenna, a device with antenna, a device with a housing (e.g. for radio, antenna, data/signal processing unit, wireless IC, circuits), device that has interface to attach/connect to/link antenna, device that is interfaced to/attached to/connected to/linked to another device/system/computer/phone/network/data aggregator, device with a user interface(UI)/graphical UI/display, device with wireless transceiver, device with wireless transmitter, device with wireless receiver, internet-of-thing (IoT) device, device with wireless network, device with both wired networking and wireless networking capability, device with wireless integrated circuit (IC), Wi-Fi device, device with Wi-Fi chip (e.g. 802.11a/b/g/n/ac/ax standard compliant), Wi-Fi access point (AP), Wi-Fi client, Wi-Fi router, Wi-Fi repeater, Wi-Fi hub, Wi-Fi mesh network router/hub/AP, wireless mesh network router, adhoc network device, wireless mesh network device, mobile device (e.g. 2G/2.5G/3G/3.5G/4G/LTE/5G/6G/7G, UMTS, 3GPP, GSM, EDGE, TDMA, FDMA, CDMA, WCDMA, TD-SCDMA), cellular device, base station, mobile network base station, mobile network hub, mobile network compatible device, LTE device, device with LTE module, mobile module (e.g. circuit board with mobile-enabling chip (IC) such as Wi-Fi chip, LTE chip, BLE chip), Wi-Fi chip (IC), LTE chip, BLE chip, device with mobile module, smart phone, companion device (e.g. dongle, attachment, plugin) for smart phones, dedicated device, plug-in device, AC-powered device, battery-powered device, device with processor/memory/set of instructions, smart device/gadget/items: clock, stationary, pen, user-interface, paper, mat, camera, television (TV), set-top-box, microphone, speaker, refrigerator, oven, machine, phone, wallet, furniture, door, window, ceiling, floor, wall, table, chair, bed, night-stand, air-conditioner, heater, pipe, duct, cable, carpet, decoration, gadget, USB device, plug, dongle, lamp/light, tile, ornament, bottle, vehicle, car, AGV, drone, robot, laptop, tablet, computer, harddisk, network card, instrument, racket, ball, shoe, wearable, clothing, glasses, hat, necklace, food, pill, small device that moves in the body of creature (e.g. in blood vessels, in lymph fluid, digestive system), and/or another device. The Type 1 device and/or Type 2 device may be communicatively coupled with: the internet, another device with access to internet (e.g. smart phone), cloud server (e.g. hub device), edge server, local server, and/or storage. The Type 1 device and/or the Type 2 device may operate with local control, can be controlled by another device via a wired/wireless connection, can operate automatically, or can be controlled by a central system that is remote (e.g. away from home).

In one embodiment, a Type B device may be a transceiver that may perform as both Origin (a Type 2 device, a Rx device) and Bot (a Type 1 device, a Tx device), i.e., a Type B device may be both Type 1 (Tx) and Type 2 (Rx) devices (e.g. simultaneously or alternately), for example, mesh devices, a mesh router, etc. In one embodiment, a Type A device may be a transceiver that may only function as Bot (a Tx device), i.e., Type 1 device only or Tx only, e.g., simple IoT devices. It may have the capability of Origin (Type 2 device, Rx device), but somehow it is functioning only as Bot in the embodiment. All the Type A and Type B devices form a tree structure. The root may be a Type B device with network (e.g. internet) access. For example, it may be connected to broadband service through a wired connection (e.g. Ethernet, cable modem, ADSL/HDSL modem) connection or a wireless connection (e.g. LTE, 3G/4G/5G, WiFi, Bluetooth, microwave link, satellite link, etc.). In one embodiment, all the Type A devices are leaf node. Each Type B device may be the root node, non-leaf node, or leaf node.

Type 1 device (transmitter, or Tx) and Type 2 device (receiver, or Rx) may be on same device (e.g. RF chip/IC) or simply the same device. The devices may operate at high frequency band, such as 28 GHz, 60 GHz, 77 GHz, etc. The RF chip may have dedicated Tx antennas (e.g. 32 antennas) and dedicated Rx antennas (e.g. another 32 antennas).

One Tx antenna may transmit a wireless signal (e.g. a series of probe signal, perhaps at 100 Hz). Alternatively, all Tx antennas may be used to transmit the wireless signal with beamforming (in Tx), such that the wireless signal is focused in certain direction (e.g. for energy efficiency or boosting the signal to noise ratio in that direction, or low power operation when "scanning" that direction, or low power operation if object is known to be in that direction).

The wireless signal hits an object (e.g. a living human lying on a bed 4 feet away from the Tx/Rx antennas, with breathing and heart beat) in a venue (e.g. a room). The object motion (e.g. lung movement according to breathing rate, or blood-vessel movement according to heart beat) may impact/modulate the wireless signal. All Rx antennas may be used to receive the wireless signal.

Beamforming (in Rx and/or Tx) may be applied (digitally) to "scan" different directions. Many directions can be scanned or monitored simultaneously. With beamforming, "sectors" (e.g. directions, orientations, bearings, zones, regions, segments) may be defined related to the Type 2 device (e.g. relative to center location of antenna array). For each probe signal (e.g. a pulse, an ACK, a control packet, etc.), a channel information or CI (e.g. channel impulse response/CIR, CSI, CFR) is obtained/computed for each sector (e.g. from the RF chip). In breathing detection, one may collect CIR in a sliding window (e.g. 30 sec, and with 100 Hz sounding/probing rate, one may have 3000 CIR over 30 sec).

The CIR may have many taps (e.g. N1 components/taps). Each tap may be associated with a time lag, or a time-of-flight (tof, e.g. time to hit the human 4 feet away and back). When a person is breathing in a certain direction at a certain distance (e.g. 4 ft), one may search for the CIR in the "certain direction". Then one may search for the tap corresponding to the "certain distance". Then one may compute the breathing rate and heart rate from that tap of that CIR.

One may consider each tap in the sliding window (e.g. 30 second window of "component time series") as a time function (e.g. a "tap function", the "component time series"). One may examine each tap function in search of a strong periodic behavior (e.g. corresponds to breathing, perhaps in the range of 10 bpm to 40 bpm).

The Type 1 device and/or the Type 2 device may have external connections/links and/or internal connections/inks. The external connections (e.g. connection 1110) may be associated with 2G/2.5G/3G/3.5G/4G/LTE/5G/6G/7G/NBIoT, UWB, WiMax, Zigbee, 802.16 etc. The internal connections (e.g., 1114A and 1114B, 1116, 1118, 1120) may be associated with WiFi, an IEEE 802.11 standard, 802.11a/b/g/n/ac/ad/af/ag/ah/ai/aj/aq/ax/ay, Bluetooth, Bluetooth 1.0/1.1/1.2/2.0/2.1/3.0/4.0/4.1/4.2/5, BLE, mesh network, an IEEE 802.16/1/1a/1b/2/2a/a/b/c/d/e/f/g/h/i/j/k/m/n/o/p/ standard.

The Type 1 device and/or Type 2 device may be powered by battery (e.g. AA battery, AAA battery, coin cell battery, button cell battery, miniature battery, bank of batteries, power bank, car battery, hybrid battery, vehicle battery, container battery, non-rechargeable battery, rechargeable battery, NiCd battery, NiMH battery, Lithium ion battery, Zinc carbon battery, Zinc chloride battery, lead acid battery, alkaline battery, battery with wireless charger, smart battery, solar battery, boat battery, plane battery, other battery, temporary energy storage device, capacitor, fly wheel).

Any device may be powered by DC or direct current (e.g. from battery as described above, power generator, power convertor, solar panel, rectifier, DC-DC converter, with various voltages such as 1.2V, 1.5V, 3V, 5V, 6V, 9V, 12V, 24V, 40V, 42V, 48V, 110V, 220V, 380V, etc.) and may thus have a DC connector or a connector with at least one pin for DC power.

Any device may be powered by AC or alternating current (e.g. wall socket in a home, transformer, invertor, shore-power, with various voltages such as 100V, 110V, 120V, 100-127V, 200V, 220V, 230V, 240V, 220-240V, 100-240V, 250V, 380V, 50 Hz, 60 Hz, etc.) and thus may have an AC connector or a connector with at least one pin for AC power. The Type 1 device and/or the Type 2 device may be positioned (e.g. installed, placed, moved to) in the venue or outside the venue.

For example, in a vehicle (e.g. a car, truck, lorry, bus, special vehicle, tractor, digger, excavator, teleporter, bulldozer, crane, forklift, electric trolley, AGV, emergency vehicle, freight, wagon, trailer, container, boat, ferry, ship, submersible, airplane, air-ship, lift, mono-rail, train, tram, rail-vehicle, railcar, etc.), the Type 1 device and/or Type 2 device may be an embedded device embedded in the vehicle, or an add-on device (e.g. aftermarket device) plugged into a port in the vehicle (e.g. OBD port/socket, USB port/socket, accessory port/socket, 12V auxiliary power outlet, and/or 12V cigarette lighter port/socket).

For example, one device (e.g. Type 2 device) may be plugged into 12V cigarette lighter/accessory port or OBD port or the USB port (e.g. of a car/truck/vehicle) while the other device (e.g. Type 1 device) may be plugged into 12V cigarette lighter/accessory port or the OBD port or the USB port. The OBD port and/or USB port can provide power, signaling and/or network (of the car/truck/vehicle). The two devices may jointly monitor the passengers including children/babies in the car. They may be used to count the passengers, recognize the driver, detect presence of passenger in a particular seat/position in the vehicle.

In another example, one device may be plugged into 12V cigarette lighter/accessory port or OBD port or the USB port of a car/truck/vehicle while the other device may be plugged into 12V cigarette lighter/accessory port or OBD port or the USB port of another car/truck/vehicle.

In another example, there may be many devices of the same type A (e.g. Type 1 or Type 2) in many heterogeneous vehicles/portable devices/smart gadgets (e.g. automated guided vehicle/AGV, shopping/luggage/moving cart, parking ticket, golf cart, bicycle, smart phone, tablet, camera, recording device, smart watch, roller skate, shoes, jackets, goggle, hat, eye-wear, wearable, Segway, scooter, luggage tag, cleaning machine, vacuum cleaner, pet tag/collar/wearable/implant), each device either plugged into 12V accessory port/OBD port/USB port of a vehicle or embedded in a vehicle. There may be one or more device of the other type B (e.g. B is Type 1 if A is Type 2, or B is Type 2 if A is Type 1) installed at locations such as gas stations, street lamp post, street corners, tunnels, multi-storey parking facility, scattered locations to cover a big area such as factory/stadium/train station/shopping mall/construction site. The Type A device may be located, tracked or monitored based on the TSCI.

The area/venue may have no local connectivity, e.g., broadband services, WiFi, etc. The Type 1 and/or Type 2 device may be portable. The Type 1 and/or Type 2 device may support plug and play.

Pairwise wireless links may be established between many pairs of devices, forming the tree structure. In each pair (and the associated link), a device (second device) may be a non-leaf (Type B). The other device (first device) may be a leaf (Type A or Type B) or non-leaf (Type B). In the link, the first device functions as a bot (Type 1 device or a Tx device) to send a wireless signal (e.g. probe signal) through the wireless multipath channel to the second device. The second device may function as an Origin (Type 2 device or Rx device) to receive the wireless signal, obtain the TSCI and compute a "linkwise analytics" based on the TSCI.

In one embodiment, a disclosed method of a sleep monitoring system comprises: obtaining a time series of channel information (CI) of a wireless multipath channel using a processor, a memory communicatively coupled with the processor and a set of instructions stored in the memory, and monitoring the sleep-related motion of the user based on the time series of CI.

The time series of CI is extracted from a wireless signal transmitted between a Type 1 heterogeneous wireless device and a Type 2 heterogeneous wireless device in a venue through the wireless multipath channel. The wireless multipath channel is impacted by a sleep-related motion of a user in the venue.

Monitoring the sleep-related motion comprises monitoring at least one of the following of the user: sleep timings, sleep durations, sleep stages, sleep quality, sleep apnea, sleep problems, sleep disorders, breathing problems, gasping, choking, teeth-grinding, pause of sleep, absence of sleep, insomnia, restlessness during sleep, hypersomnia, parasomnia, day-time sleepiness, sleep locations, sleep-while-driving, sleep disruptions, nightmares, night terrors, sleep walking, REM sleep behavior disorder, Circadian rhythm disorder, non-24-hour sleep-wake disorder, periodic limb movement disorder, shift-work sleep disorder, narcolepsy, confusional arousals, sleep paralysis, another sleep-related condition, and/or another sleep-related behavior.

Sleep timings comprises timings of at least one of: go-to-bed, sleep-onset, wake-up, REM-onset, NREM-onset, onset of sleep stage transitions, sleep disorders, sleep problems, breathing problems, insomnia, hypersomnia, parasomnia, sleep hypnogram-related events, sleep disruptions, sleep apnea, snoring during sleep, sleeping-not-on-a-bed, day-time sleep, sleep-walking, sleep-related events, sleep-related condition, and/or, sleep-related behavior, etc.

Sleep stages comprises at least one of: wake-up, rapid-eye-movement (REM) and/or non-REM (NREM).

At least one of: a time function of breathing rate, and a time function of motion statistics, of the user may be computed based on the series of CI. If breathing is not detected at time t, the breathing rate at time t may be computed as zero. The sleep-related motion of the user may be monitored based on at least one of: the time function of breathing rate, and/or the time function of motion statistics, of the user.

At least one of: a time function of breathing ratio, and a time function of motion ratio, of the user may be computed based on the series of CI. The breathing ratio at time t may be computed as percentage of time when the time function of breathing rate is non-zero in a first time window comprising the time t. The motion ratio at time t may be computed as percentage of time when the time function of motion statistics is larger than a first threshold within a second time window comprising the time t. The sleep-related motion of the user may be monitored based on at least one of: the time function of breathing ratio, and/or the time function of motion ratio, of the user.

A sleep stage may be classified as "awake" if at least one of: the motion ratio is greater than a second threshold, and/or the breathing ratio is less than a third threshold. The sleep stage may be classified as "asleep" if at least one of: the motion ratio is less than the second threshold, and/or the breathing ratio is greater than the third threshold. The "asleep" stage may comprise at least one of: rapid-eye-movement (REM) stage, and/or non-REM (NREM) stage.

A breathing rate trend function may be computed by low-pass filtering the time function of breathing rate. A detrended breathing rate function may be computed by subtracting the breathing rate trend function from the time function of breathing rate. A time function of breathing rate variance may be computed by computing variance of the detrended breathing rate function within a sliding time window. The sleep-related motion of the user may be monitored based on the time function of breathing rate variance.

An average NREM breathing rate may be computed by identifying a peak of a histogram of the time function of breathing rate in "asleep" stage in an overnight period. (e.g. the whole night, or the whole night subtracting any "awake" periods). A time function of breathing rate deviation may be computed by computing a distance between the average NREM and a percentile of the breathing rate within a sliding time window. The sleep stage may be classified as at least one of: REM stage and/or NREM stage, based on the time function of breathing rate deviation.

A time function of breathing rate variance may be computed by computing variance of a detrended breathing rate function within a first sliding time window. A time function of breathing rate deviation may be computed by computing a distance between an average NREM and a percentile of the breathing rate within a second sliding time window. The sleep stage may be classified as at least one of: REM stage, and/or NREM stage, based on the time function of breathing rate variance and the time function of breathing rate deviation.

A classifier may be trained based on at least one of: breathing rate variance, and breathing rate deviation, using machine learning. The machine learning may comprise at least one of: supervised learning, unsupervised learning, semi-supervised learning, active learning, reinforcement learning, support vector machine, deep learning, feature learning, clustering, regression, and/or dimensionality reduction. The sleep stage may be classified as at least one of: REM stage, and/or NREM stage, based on the classifier.

A quantity related to the sleep-related motion of the user may be computed based on the time series of CI. The sleep-related motion of the user may be monitored based on the quantity.

The quantity may comprise at least one of: the time the user goes to bed, the time the user gets out of bed, the sleep onset time, total time it takes the user to fall asleep, the wake up time, sleep disruption time, number of sleep disruption period, mean disruption duration, variance of disruption duration, total time in bed, total time the user is asleep, time periods of REM, time periods of NREM, time periods of awake, total time of REM, total time of NREM, number of REM periods, number of NREM periods, time of toss and turn in bed, duration of tossing and turning, hypnogram, periods of apnea, periods of snore, total duration of apnea, number of apnea periods, average duration of apnea period, periods of breathing problems, sleep quality score, daytime sleep, time periods of daytime sleep, total duration of daytime sleep, number of period of daytime sleep, average duration of period of daytime sleep, and another quantity.

The present teaching discloses the model, design, and implementation of SMARS (Sleep Monitoring via Ambient Radio Signals), which is the first practical sleep monitoring system that exploits commodity Ambient Radio Signals to recognize sleep stages and assess the otherwise elusive sleep quality. Different from prevailing solutions, the disclosed solution looks forward to a future smart home that monitors daily sleep in a ubiquitous, non-invasive, contactless, and accurate manner, without instrumenting the body or the bed. One can observe an opportunity towards such a system by two perspectives: 1) Clinical study has shown that physiological activity varies among different sleep stages. For example, breathing rate becomes irregular and fast since brain oxygen consumption increases during REM sleep, and is more stable and slower during NREM sleep, rendering the feasibility of sleep staging based on breathing monitoring. 2) Recent advances in wireless technology have demonstrated non-contact sensing of body motions in the environments. Chest and abdomen motions caused by breathing can alter radio signal propagations and thus modulate the received signals, from which it is then possible to decipher breathing. One can explore a synergy between the two perspectives, resulting in a system to leverage ambient radio signals (e.g., WiFi) to capture a person's breathing and motion during sleep and further monitor the sleep behaviors.

SMARS works in a non-obtrusive way without any body contact. All that a user needs to do is to set up one single link between two commodity radios by, e.g., simply placing a receiver if a wireless router is already installed inside the home. SMARS advances the literature by a novel statistical model that allows highly accurate and instantaneous breathing estimation. On this basis, SMARS is able to distinguish different sleep stages, which is previously only obtainable by expensive dedicated hardware. Specifically, SMARS excels in three unique aspects to deliver practical sleep monitoring. First, one can devise a statistical model on motion in Channel State Information (CSI) that leverages all reflection and scattering multipaths indoors.

Second, SMARS achieves accurate respiratory rate estimation instantaneously and robustly. Most of previous breathing estimation schemes assume constant breathing rate during a relatively large time window to gain sufficient frequency resolution, losing fine-grained breathing variations during sleep. In addition, minute breathing motions can be easily buried in CSI measurement noises, rendering existing philosophies effective only in extraordinary close proximity (typically within 2~3 m) without any extraneous motions. To improve time resolution, SMARS exploits the time-domain Auto-Correlation Function (ACF) to estimate breathing rate, which can report real-time breathing rates as frequent as every one second and make it possible to capture instantaneous breathing rate changes. By using ACF, SMARS also circumvents the use of noisy phase and the usually handcrafted CSI denoising procedure. More importantly, by eliminating the frequency offsets and thus synchronizing breathing signal over different subcarriers, ACF allows us to perform Maximal Ratio Combining (MRC) to combine multiple subcarriers to combat measurement noises and maximize breathing signals in an optimal way. By doing so, one can push the limit of the breathing signal to noise ratio (SNR) and thus significantly increase the sensing sensitivity for larger coverage as well as weaker breathing. Specifically, SMARS can reliably detect breathing when a person is 10 m away from the link, or behind a wall, which is even better than specialized low-power radars.

Finally, based on the extracted breathing rates and motion statistics during sleep, one can recognize different sleep stages (including wake, REM and NREM) and comprehensively assess the overall sleep quantity and quality. Based on in-depth understanding of the relationship between breathing rates and sleep stages, one can extract distinctive breathing features for classification for sleep staging. None of existing works using off-the-shelf devices can achieve the same goal of staging sleep.

A real-time system has been implemented on different commercial WiFi chipsets and its performance is evaluated through extensive experiments. The evaluation includes two parts: 1) One can deploy SMARS in 6 homes with 6 healthy subjects and collect 32 nights of data, 5 out of which have PSG data recorded by commercial devices. The results show that SMARS achieves great performance, with a median breathing estimation error of 0.47 breath per minute (bpm) and a 95% tile error of 2.92 bmp. Regarding sleep staging, SMARS produces a remarkable accuracy of 85.2%, while commercial solutions, e.g., EMFIT based on contact sensors and ResMed using radar, have accuracies of only 69.8% and 83.7% respectively. 2) One can further validate SMARS on a recently released dataset on RF-based respiration monitoring. The dataset collected 20 patients' overnight sleep for comparative evaluation of four state-of-the-art breathing monitoring systems, using clinically labeled PSG data as ground truths. As reported, all the four systems (based on ZigBee, Sub-RSS radio, UWB radar, and WiFi CSI, respectively) produce significant median errors of about 2~3 bpm and 95% tile errors of around or above 10 bpm. As comparison, SMARS achieves significant improvements by decreasing the median error to 0.66 bpm and the 95% tile error to 3.79 bpm. By achieving promising performance, SMARS can deliver clinically meaningful sleep monitoring for daily and regular use in practice and takes an important step towards a future smart home that monitors personal health everyday life.

In a nutshell, the core contribution here is SMARS, the first system that enables a smart home to stage an inhabitant's sleep using commodity off-the-shelf WiFi devices, by achieving highly accurate and instantaneous breathing estimation in the wild. SMARS also contributes the first statistical model for understanding and capturing motions in CSI, which will renovate various applications in wireless sensing.

Different from controlled and short experiments conducted in previous studies, one can envision that SMARS can be deployed easily in a smart home to monitor a person's overnight breathing and movements in the wild, without body and bed instrumentation. SMARS can continuously track the subject's mild and immediate respiratory rate changes during different sleep stages, precisely with sub-bpm accuracy and instantaneously with sub-second time resolution. Furthermore, the disclosed system, built upon a single Tx-Rx link, can monitor breathing at distances up to 10 meters or behind a wall, providing a good coverage for common bedrooms. In addition, the breathing estimation is robust to various sleep positions and postures, and independent from different environments or subjects. Last, considering practical in-home use, SMARS is designed based on commodity off-the-shelf devices, especially those already existed in today's smart homes, e.g., WiFi routers. The system works with fairly low sampling rate of 30 Hz or even 10 Hz, producing negligible impacts on in-home wireless connections.

SMARS also provides super-sensitive capability to detect extraneous motions (walking or other body motions beyond breathing), which could dominate breathing motion and render it not recognizable. Even wearables like chest bands cannot get reliable estimates under large non-breathing motions since breathing is buried in such cases. With that, SMARS can detect arbitrary motions and uses the quasi-static periods without large motions for breathing estimation. SMARS then stages a person's overnight sleep by fusing both motion statistics and breathing rates.

Wireless sleep monitoring faces multiple fundamental challenges. A major limitation of existing works is their large errors and delays in breathing estimation, making them infeasible for sleep staging. Moreover, they are not practical for real-world deployment since most of them are validated only under controlled settings with short period and narrow coverage. Technically, the following two key challenges prohibit previous approaches from accurate and robust measurements. The first challenge is multipath. Existing works usually adopt simplified models that make unrealistic assumptions of indoor multipath propagation. For example, most of existing works assume one dominate mirror reflection path from human body under 2-ray models that are developed for and only hold in outdoor environments, and accordingly attempt to geometrically interpolate multipath constructive and destructive interferences. In reality, however, signals bouncing off human body may reflect, scatter, and diffract before finally superimpose at the receiver, producing up to hundreds of multipaths indoors. As a result, most of them can only work in clear LOS scenarios with strong breathing in proximity, where a dominant reflection path exists. A more realistic model is demanded for practical breathing estimation. The second challenge is low breathing SNR. Breathing signals (i.e., the signals modulated on the received signals by breathing) are typically very weak and would easily fade out when propagating a long distance or penetrating through a wall, resulting in extremely low breathing SNR at the receiver. To improve breathing estimation sensitivity, previously works resort to selecting one best subcarrier among others (usually using CSI amplitude or variance) or take the average over all subcarriers for breathing estimation. However, one can make the following observations, as will be further detailed below, that demonstrate the flaws of these methods: 1) any single subcarrier does not produce the optimal estimation, no matter what criteria is used for selection; 2) CSI amplitude or its variance is not an effective metric for subcarrier selection, where the subcarrier with largest amplitude or variance usually does not capture the breathing signal to the best; 3) due to frequency offsets across different subcarriers, CSI amplitudes responding to the person's breathing are unsynchronized and contain uncertain offsets. Consequently, the CSI on different subcarriers cannot be directly averaged, which does not necessarily amplify, yet may instead rule out breathing signals.

The present teaching overcomes the above challenges by a novel model that investigates the statistical characteristics of all reflection and scattering multipaths. The present teaching discloses an approach to synchronize the amplitude responses on all subcarriers and then optimally combine them to maximize the breathing SNR, making accurate and instantaneous breathing estimation and further sleep staging possible, for the first time, on commodity devices.

Instantaneous Breathing Rate Estimation

Given a wireless transmission pair each equipped with omnidirectional antennas, the channel frequency response (CFR), also called as Channel State Information (CSI), for the fading multipath channel at time t is commonly modeled as $$H(t,f) = \sum_{l \in \Omega} a_l(t) \exp(-j2\pi f \tau_l(t)), \quad (1)$$

where $a_l(t)$ and $\tau_l(t)$ denote the complex amplitude and propagation delay of the l-th multipath component (MPC), respectively, and $\Omega$ denotes the set of MPCs. The propagation delay is a function of the propagation distance:

$$\tau_l(t) = \frac{d_l(t)}{c},$$

where c is the speed of light and $d_l(t)$ is the traveled distance of the l-th MPC. f denotes the particular frequency where the channel is measured. For example, in an OFDM-based communication system, such as WiFi, LTE, 5G, etc., the CSI is measured at each subcarrier with frequency f.

CSI depicts how radio signals propagate from a Tx to a Rx, e.g., reflected or scattered off all reflectors in the space such as the walls, furniture, human bodies, etc., and is highly sensitive to environmental perturbations. Anybody motions, including minute chest and abdomen movements, will alter the paths of signal propagation and thus modulate the wireless signal before it arrives at the receiver, allowing SMARS to capture these motions and monitor human's sleep from the measured CSI time series.

Modeling Motion in CSI

Consider the case when there is a static person breathing indoors with a cycle of $T_b$ seconds. The MPCs can be classified into two sets: $\Omega_s(t)$ and $\Omega_d(t)$, where $\Omega_s(t)$ denotes the set of time-invariant MPCs, e.g., reflected off the floor and walls, and $\Omega_d(t)$ denotes the set of time-varying MPCs, e.g., reflected off the human body. Due to the periodic chest or abdomen movement during normal breathing, the propagation distance $d_l(t)$ of each MPC $\forall l \in \Omega_d(t)$ changes periodically with the same cycle as the breathing movement, i.e., $d_l(t+T_b)=d_l(t)$. Since the amplitude of breathing movement is small, the change in the propagation distance for each dynamic path is also small. Therefore, it is reasonable to assume that both the sets $\Omega_s(t)$, $\Omega_d(t)$ and the complex amplitude of each MPC $a_l(t)$ are time-invariant within a sufficiently short period. Thus the CSI can be written as $$H(t,f) = \sum_{l_s \in \Omega_s} a_{l_s} \exp\left(-j2\pi f \frac{d_{l_s}}{c}\right) + \sum_{l_d \in \Omega_d} a_{l_d} \exp\left(-j2\pi f \frac{d_{l_d}(t)}{c}\right) \triangleq \quad (2)$$

$$H_s(f) + H_d(t,f),$$

where $H_s(f)$ and $H_d(t,f)$ denote the contribution of the time-invariant MPCs and time-varying MPCs, respectively.

In real measurements, H(t, f) is corrupted by the phase noise, caused by the timing and frequency synchronization offsets, and the additive thermal noise n(t, f), and the reported CSI $\tilde{H}(t,f)$ can be expressed as $$\tilde{H}(t,f) = \exp(-j(\alpha(t)+\beta(t)f))H(t,f)+n(t,f), \quad (3)$$

where $\alpha(t)$ and $\beta(t)$ are the random initial and linear phase distortions at time t, respectively. Define the channel power response G(t, f) as the square of the magnitude of $\tilde{H}(t,f)$:

$$G(t,f) \triangleq |\tilde{H}(t,f)|^2 = |H(t,f)|^2 + 2Re\{n^*(t,f)H(t,f)$$

$$\exp(-j(\alpha(t)+\beta(t)f))\} + |n(t,f)|^2$$

$$\triangleq |H(t,f)|^2 + \varepsilon(t,f) \quad (4)$$

where the superscript * denotes the operator of complex conjugate, the operator Re{x} denotes the real part of x, and $\varepsilon(t, f)$ is defined as the noise term, which can be approximated as additive white Gaussian noise (AWGN) with variance $\sigma^2(f)$ and is statistically independent of H(t, f). From (2) and the fact that $d_l(t+T_b)=d_l(t)$, $\forall l \in \Omega_d$, one can have $|H(t+T_b, f)|^2 = |H(t, f)|^2$. Thus, G(t, f) is modeled as a noisy periodic signal with a period of $T_b$.

One can measure the CSI power response G(t, f) using a pair of commercial WiFi devices for both the two cases, when a subject breathing in a LOS and a NLOS location with respect to the transmission pair, respectively. For the LOS case, the strength of the measured breathing signal is strong and the periodic pattern can be easily observed by most of subcarriers. For the NLOS case, however, there are no apparent periodic patterns that can be observed since the breathing signal is much weaker.

Note that G(t, f) is a result of numerous multipath components adding up together in a complex way expressed in (2). Both the amplitudes and the phases of the breathing signal measured by CSI are different for different subcarriers. Accordingly, it is reasonable to express $|H(t, f)|^2$ in the following form:

$$|H(t,f)|^2 = g(f)b(t-\Delta t_f), \quad (5)$$

where b(t) denotes a periodic stationary breathing signal with zero mean, which is related to the movement of the chest and abdomen, and g(f) and $\Delta t_f$ stand for the gain and the random initial phase of the breathing signal measured at the frequency f, respectively.

Combining (4) and (5), the received signal at subcarrier with frequency f is expressed as $$G(t,f)=g(f)b(t-\Delta t)+\varepsilon(t,f). \quad (6)$$

Breathing estimation is then conducted based on the power response G(t, f), which circumvents the use of noisy CSI phase and the usually handcrafted phase cleaning step.

Observing that breathing signal is periodic, previous methods usually perform frequency analysis on a certain window to estimate breathing rate. As a result, large delay (e.g., more than 10 seconds) is incurred to gain better frequency resolution. In addition, immediate breathing rate changes are missed since breathing rate is assumed to be constant during the analyzing window. Differently in SMARS, one can adopt a statistical approach by examining the autocorrelation function (ACF) of CSI power response G(t, f). As a time-domain approach, ACF significantly shortens the time delay window required and produces instantaneous estimation.

ACF Calculation. The ACF for a stationary signal x(t) is defined as follows:

$$\rho(\tau) = \frac{\text{cov}[x(t), x(t+\tau)]}{\text{cov}[x(t), x(t)]}, \quad (7)$$

where $\tau$ denotes the time lag, and cov[•] denotes the covariance operator. Thus, the ACF of G(t, f) is computed as $$\rho_G(\tau, f) = \frac{g^2(f)}{g^2(f)+\sigma^2(f)} \rho_b(\tau) + \frac{\sigma^2(f)}{g^2(f)+\sigma^2(f)} \delta(\tau), \quad (8)$$

where $\rho_b(\tau)$ is that ACF of b(t), and $\delta(\tau)$ denotes the Dirichlet function. Define $$k(f) \triangleq \frac{g^2(f)}{g^2(f)+\sigma^2(f)}$$

as the normalized channel gain, and for $\tau \neq 0$, one can have $$\rho_G(\tau,f)=k(f)\rho_b(\tau). \quad (9)$$

In practice, the sample ACF is used instead, which is an estimate of the ACF, and one can use $n(\tau, f)$ to stand for the estimation noise of the ACF, i.e., $$\hat{\rho}_G(\tau,f)=k(f)\rho_b(\tau)+n(\tau,f). \quad (10)$$

FIG. 1 illustrates exemplary autocorrelation functions 100 of the received signals under different scenarios, according to one embodiment of the present teaching. As shown in FIG. 1, when there is a breathing signal, the ACF will exhibit a definite peak at a certain delay (although the peak value may differ over different subcarriers), contributed by the periodic breathing motions. On the contrary, no certain peaks can be observed on any subcarrier when there is no breathing (i.e., no periodic motions). In principle a time delay slightly longer than one breathing cycle (e.g., 5 to 7 seconds) is sufficient to pick up the first breathing rate and later on instantaneous estimates can be produced every one second.

Motion Statistics: In prior to breathing estimation, a key step is to examine whether there exists detectable breathing signal (i.e., whether breathing exists without extra big motions). As mentioned before, breathing will easily be buried in other large body motions, and should not be estimated if there is none. One can also investigate the property of the ACF for this purpose since, in addition to breathing, the calculated ACF actually offers indicators for detection of arbitrary motions.

Recall (9), when $\tau \to 0$, one can have $$\lim_{\tau \to 0} \rho_G(\tau, f) = k(f) \lim_{\tau \to 0} \rho_b(\tau). \quad (11)$$

Since the movement of chest and abdomen is continuous, the breathing signal b(t) is also continuous in time and one can have $\lim_{\tau \to 0} \rho_b(\tau) = 1$, which leads to the following result:

$$\lim_{\tau \to 0} \rho_G(\tau, f) = k(f). \quad (12)$$

As a result, when the channel sampling rate $F_s$ is high enough, the quantity $\hat{\rho}_G(\tau = 1/F_s, f)$ is close to the channel gain k(f). That is, k(f) can be estimated as $$\hat{k}(f) = \hat{\rho}_G(\tau = 1/F_s, f). \quad (13)$$

$\hat{k}(f)$ indicates the strength of total motions existing in the monitored area and is named as Motion Statistics in the following, quantifying the total dynamics of the environment, including periodic (e.g., breathing) and non-periodic motion. The larger motion statistics, the more sensitive one subcarrier is to motions.

Figure 2:
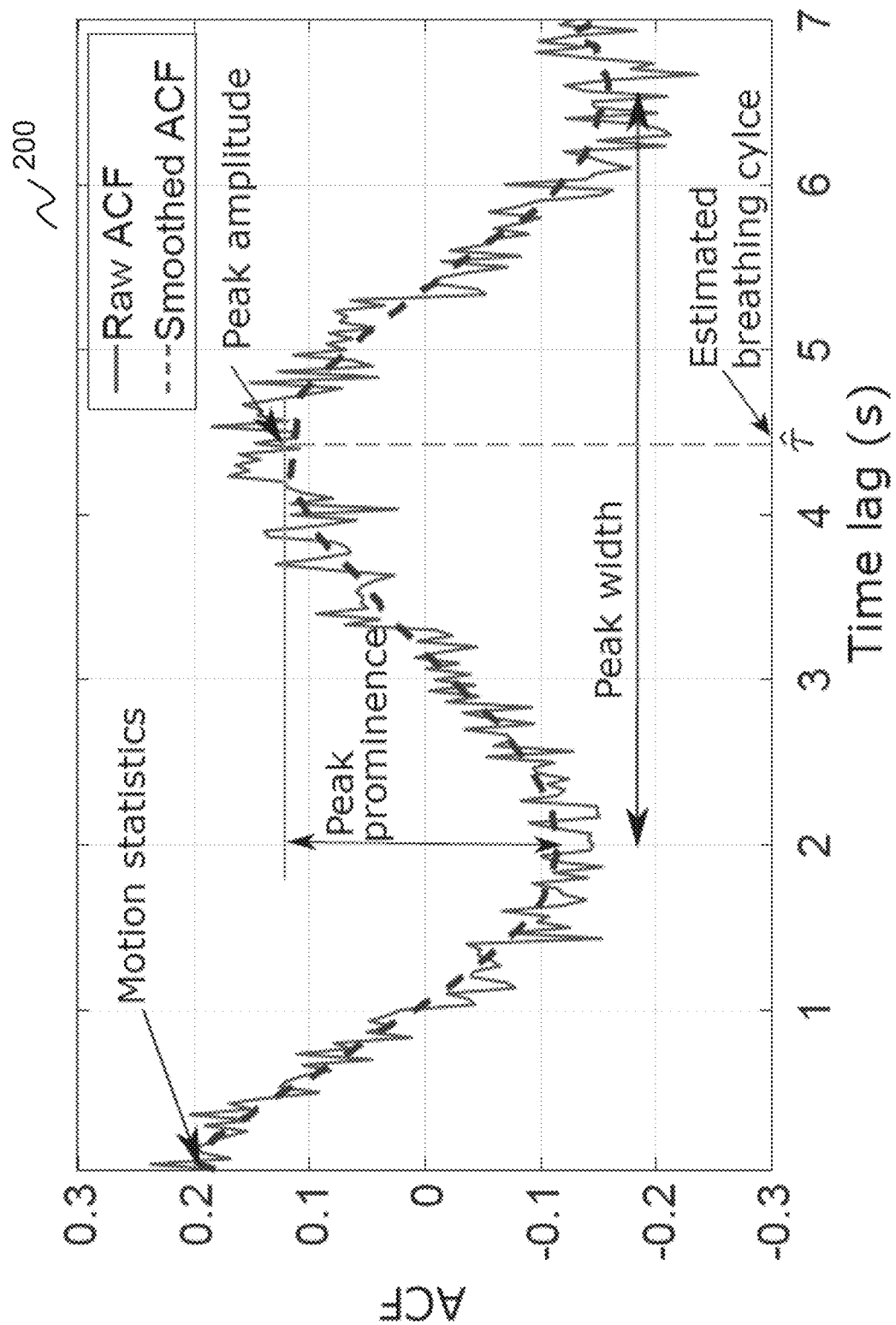
FIG. 2 illustrates exemplary features extracted from the derived autocorrelation functions for breathing detection and estimation, according to one embodiment of the present teaching.

Breathing Detection and Estimation: Based on the calculated ACF and its inherent characteristics, the system first detects the presence and absence of breathing and, if presented, then estimates the breathing rate, accurately and instantaneously. FIG. 2 illustrates exemplary features 200 extracted from the derived autocorrelation functions for breathing detection and estimation, according to one embodiment of the present teaching. As shown in FIG. 2, for a subcarrier with frequency f, one can extract several features from $\hat{\rho}_G(\tau, f)$ for breathing detection, in addition to the motion statistics. The first feature is Peak Prominence, which is the vertical distance between the peak value and the largest height of the adjacent valleys, which measures the likelihood of the existence of the peak. The second feature is Peak Width, which is the horizontal distance between the two adjacent valleys, which also measures the likelihood of the existence of the peak. The third feature is Peak Amplitude, which is the height of the peak, which measures the amplitude of the ACF of the breathing signal and will be comparable to the value of motion statistic in presence of only breathing motion. The fourth feature is Motion Interference Ratio, which is the ratio between the motion statistics and peak amplitude, which measures degree of the interference of the non-breathing motion, such as body movements, walking, standing up, typing keyboard, etc., in the environment. The fifth feature is Peak Location, which is the horizontal distance between the origin and the peak (i.e., time lags), which measures the breathing cycle. Other features may be computed.

In general, the larger the motion statistics, peak prominence, peak width, peak amplitude and the smaller the motion interference ratio, the more likely for the presence of the breathing signal. In one embodiment, the above features are jointly fused to claim the existence of breathing signal and the corresponding breathing rate. Once there is a breathing signal, the breathing rate can be estimated as BR=60/$\hat{\tau}$ breath per minute, where f is the location (i.e., time lags) of the first dominant peak of $\hat{\rho}_G(\tau, f)$.

Maximizing Breathing Signal

In practice, the SNR of the breathing signal on each subcarrier modulated by minute breathing motions is very low, especially when the person being monitored is far away from the link, covered by quilts, or behind the wall, resulting in limited coverage and vulnerable estimation that prevents the applications of the existing RF-based approaches. Previous approaches attempting to select a best subcarrier among others or to average over all to improve breathing signal do not produce reliable, not to mention optimal results.

To boost the breathing SNR, the system may combine the breathing signals measured on different subcarriers in the optimal way. In one embodiment, the disclosed design is based on Maximal Ratio Combining (MRC), a classical diversity combining method in telecommunications that maximize signal SNR by optimally combining received signals on multiple antennas.

MRC Model. One can first review the basic concept of MRC in telecommunications in the following. Let vector $x = [x_1, \ldots, x_N]^T$ denote the received signal at N antennas, which can be written as $$x = hu + n, \quad (14)$$

where $h = [h_1, \ldots, h_N]^T$ denotes the constant channel gains, u denotes the transmitted random signal with unit power, and $n = [n_1, \ldots, n_N]_T$ stands for the I.I.D. AWGN with variance $\sigma^2$. Let r denote the linearly combined signal:

$$r = w^T x = w^T hu + w^T n, \quad (15)$$

where $w = [w_1, \ldots, w_N]_T$ denotes the normalized weight of each received signal at each antenna, that is, $\|w\| = 1$. The SNR, denoted as y, of the output signal r can be denoted as $$\gamma = \frac{\mathbb{E}[|w^T hu|^2]}{\mathbb{E}[|w^T n|^2]} = \frac{|w^T h|^2}{\sigma^2}. \quad (16)$$

By the Cauchy-Schwarz inequality, one can have $|w^T h|^2 \leq \|w\| \|h\|$. The equality is achieved when w is linearly proportional to h, i.e., $w^* = h/\|h\|$, and the maximum of output SNR can be obtained as the sum of the SNR of received signals at each antenna, i.e., $\gamma = \gamma_1 + \ldots + \gamma_N$, where $\gamma_i = |h_i|^2/\sigma^2$.

MRC on Breathing Signal. In the context of breathing estimation with CSI, the breathing signal b(t) is measured by multiple subcarriers. The SNR of the breathing signal, denoted as $\gamma(f)$, measured on subcarrier with frequency f at time t is defined as $$\gamma(f) = \frac{\mathbb{E}[(g(f)b(t-\Delta t_f))^2]}{\mathbb{E}[\varepsilon^2(t,f)]} = \frac{g^2(f)\mathbb{E}(b^2(t-\Delta t_f))}{\sigma^2(f)}, \quad (17)$$

where $\mathbb{E}[\bullet]$ stands for the expectation operator. For convenience, the average power of the breathing signal b(t) is normalized to unit power by definition, that is, $\mathbb{E}[b^2(t)]=1$, and thus one can have $\gamma(f)=g^2(f)/\sigma^2(f)$.

By using ACF instead of G(t, f) itself, SMARS successfully synchronizes and transforms the breathing signal into an appropriate form to apply MRC for optimal subcarrier combining.

As discussed before, when the breathing signal is extremely weak, i.e., k(f) is close to zero, G(t, f) is dominated by the white noise and thus, each tap of its ACF follows a zero-mean normal distribution with equal variance 1/N, i.e., $n(r,f) \sim \mathcal{N}(0,1/N)$, where N is the number of samples used in the estimation of the ACF. Note that the variance of $n(\tau, f)$ is the same for different subcarriers, solving the first challenge. The ACF $\rho_b(\tau)$ are inherently synchronized over all subcarriers and is independent of the time origin. In other words, different subcarriers experience the same signal $\rho_b(\tau)$, which addresses the second challenge. Regarding the third challenge, the channel gain can be estimated by $\hat{\rho}_G(\tau=1/F, f)$, as denoted in (13). This is a key feature that underpins the use of MRC; otherwise one can still combine different subcarriers, but not optimally. To conclude, MRC can now be applied to the ACF of breathing signal correspondingly to maximize the SNR.

Maximizing Breathing SNR. The SNR of breathing signal, as in (17), cannot be directly maximized since the channel gain and noise cannot be measured in CSI. One can thus maximize the SNR of the ACF of breathing signal.

Recall (10) and that the variance of the noise term is approximated as 1/N, and thus, the SNR of the ACF of each subcarrier can be estimated as $N\hat{k}^2(f)$. Since the SNR of the breathing signal after MRC is the additive of the SNR measured by each subcarrier, the SNR of the combined ACF is expressed as $$\gamma = N\Sigma_{f\in F}\hat{k}^2(f), \quad (18)$$

which can be maximized, given a fixed number of subcarriers and sample number of N, by setting the optimal weight $w^{\hat{a}}(f)$ to $\hat{\rho}_G(\tau=1/F_s, f)$ in the following linear combination: $\forall \tau$, $$\hat{\rho}_b(\tau)\Sigma_{f\in F} \, w^{\hat{a}}(f)\hat{\rho}_G(\tau,f) = \Sigma_{f\in F} \, \hat{\rho}_G(\tau=1/F_s,f)\hat{\rho}_G(\tau,f). \quad (19)$$

Here $\hat{\rho}_b(\tau)$ is the ACF of the combined signal, of which the SNR $\gamma$ is maximized.

Figure 3:
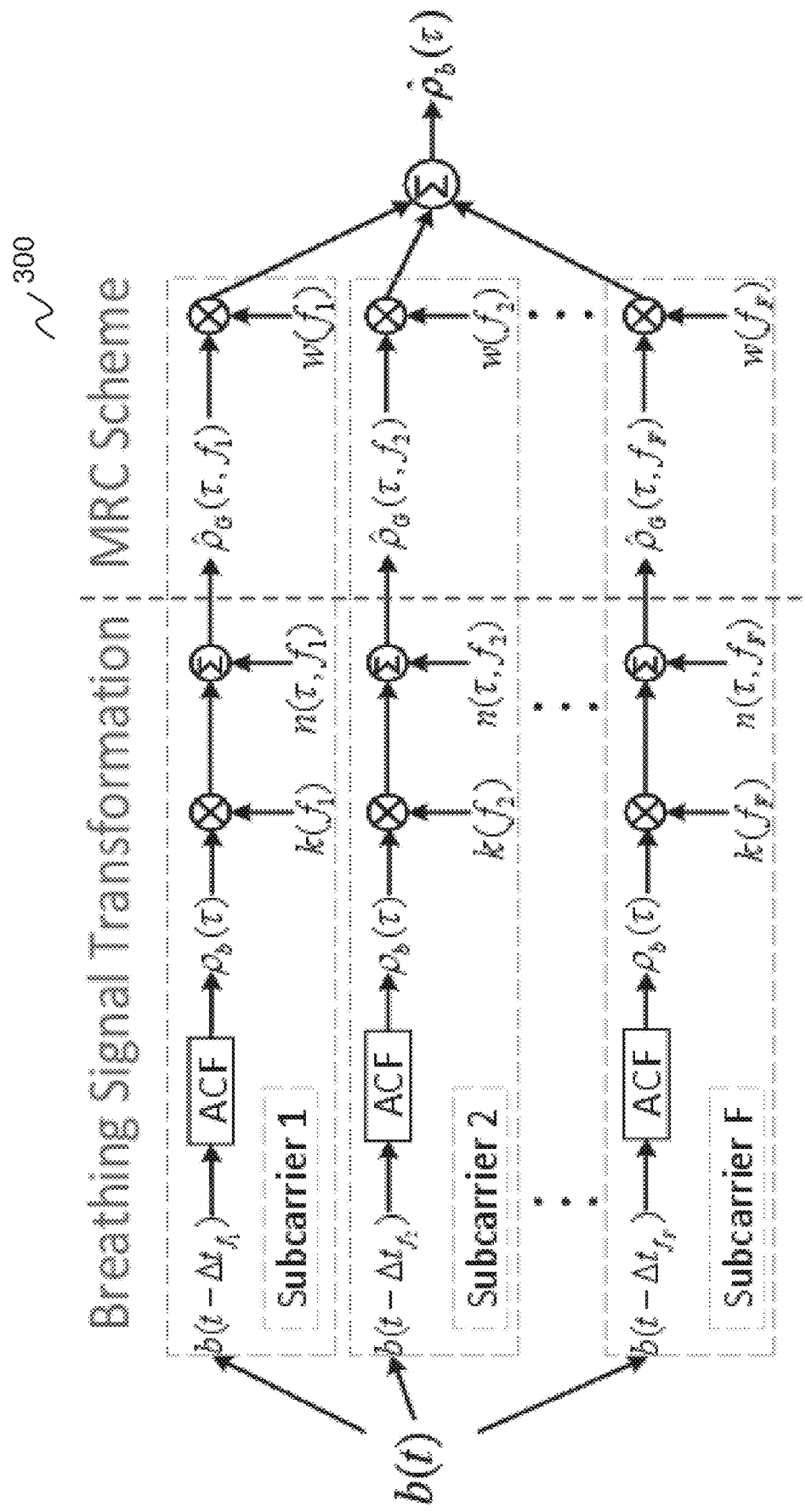
FIG. 3 illustrates an exemplary scheme for breathing signal extraction and maximization, according to one embodiment of the present teaching.

FIG. 3 illustrates an exemplary scheme 300 for breathing signal extraction and maximization, according to one embodiment of the present teaching. The left part of the FIG. 3 shows the decomposition of the measured ACF of the channel power response when a person breathes normally in the monitored area, while the right part shows the MRC scheme for boosting the SNR of the ACF of the breathing signal.

Figure 4:
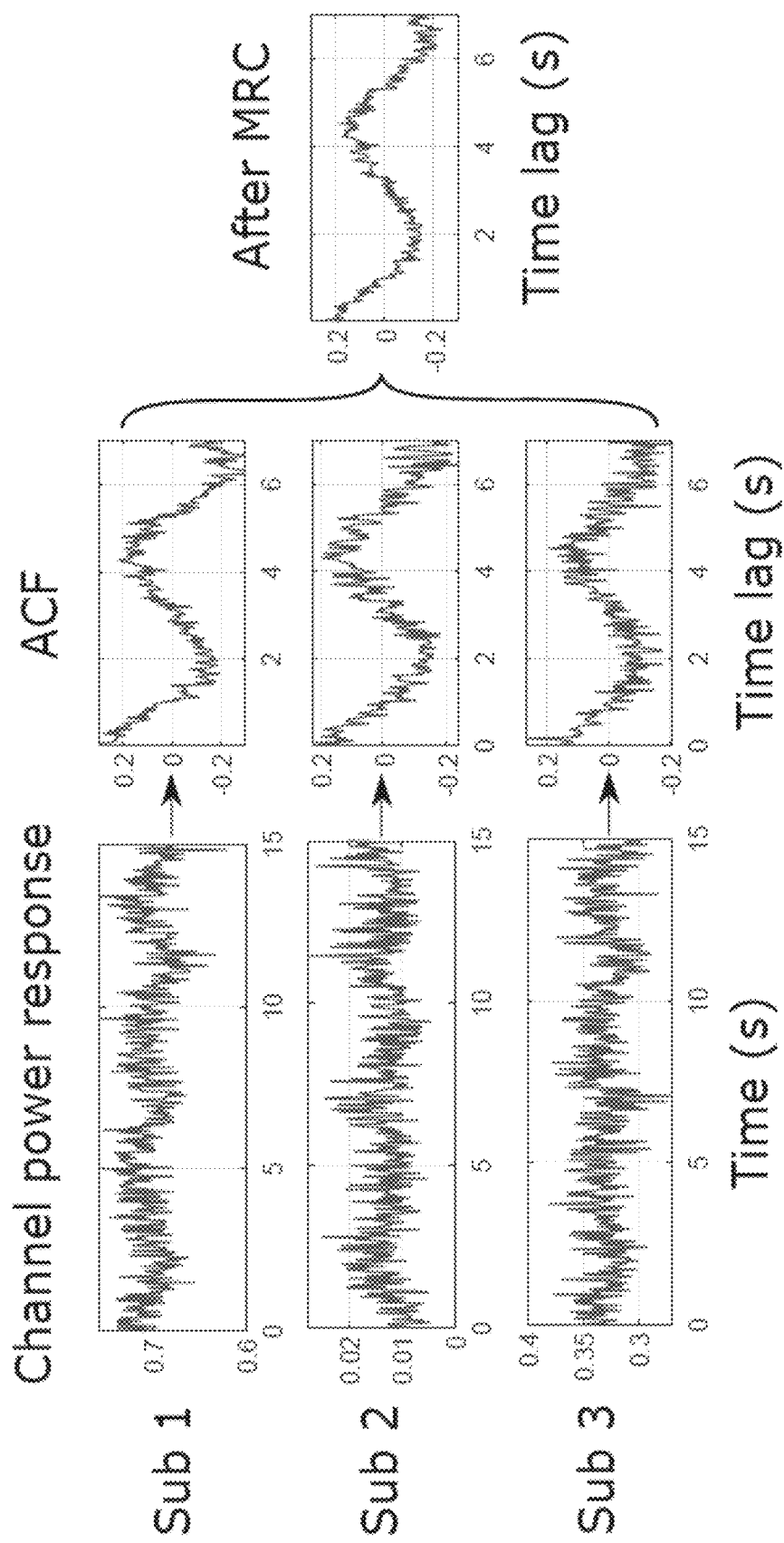
FIG. 4 illustrates an exemplary breathing signal based on real-world measurements, according to one embodiment of the present teaching.
Figure 5:
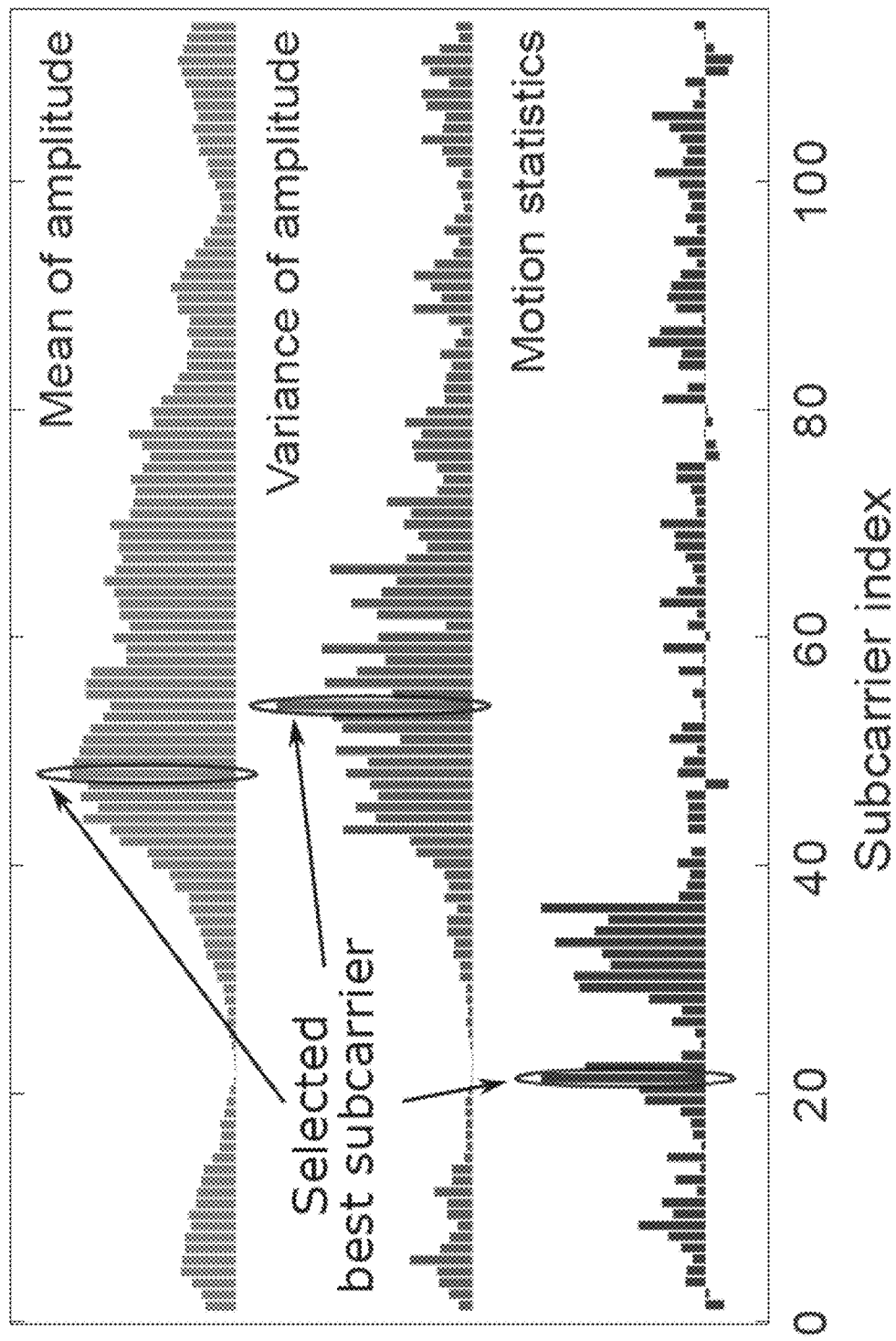
FIG. 5 demonstrates gains of a disclosed scheme for breathing signal extraction and maximization, according to one embodiment of the present teaching.

FIG. 4 depicts an illustrative example based on real-world measurements, where the SNR of the breathing signal is amplified by 2.5 dB compared to the best subcarrier indicated by largest variance and by 3.7 dB compared to directly averaging all subcarriers. FIG. 5 further demonstrates the gains of the disclosed ACF-based MRC scheme and confirms the observations herein that amplitudes and their variances are not effective metrics for subcarrier selection. As seen, the subcarrier that is the most sensitive to motion (i.e., holding the largest motion statistic) could experience very small amplitude and low variance.

Given the combined breathing signal with maximized SNR, SMARS then performs breathing detection and estimation, as described before, yet based on $\hat{\rho}_b(\tau)$, the ACF of the combined signal, instead of $\hat{\rho}_G(\tau, f)$ on a specific subcarrier.

The present teaching discloses the design of the sleep monitoring module of SMARS.

Sleep Stage Recognition

SMARS divides the continuous motion and breathing estimates of overnight sleep into 300-second epochs. For each epoch, SMARS recognizes three different sleep stages, i.e., wake, REM sleep and NREM sleep. The staging is performed in two steps: First, SMARS differentiates wake from sleep mainly by body motions; Second, REM and NREM stages are further identified during sleep period.

Sleep/Wake Detection. SMARS first implements a sleep-wake detector to identify the sleep and wake states. The key insight is that, more frequent body movements will be observed when a subject is awake, while mainly breathing motion presents when he/she is asleep. Since bodily movements are significantly stronger than breathing motions, and both of them can be easily captured and quantified by the motion statistic defined herein, SMARS utilizes it to distinguish between sleep and wake states.

Figure 6A:
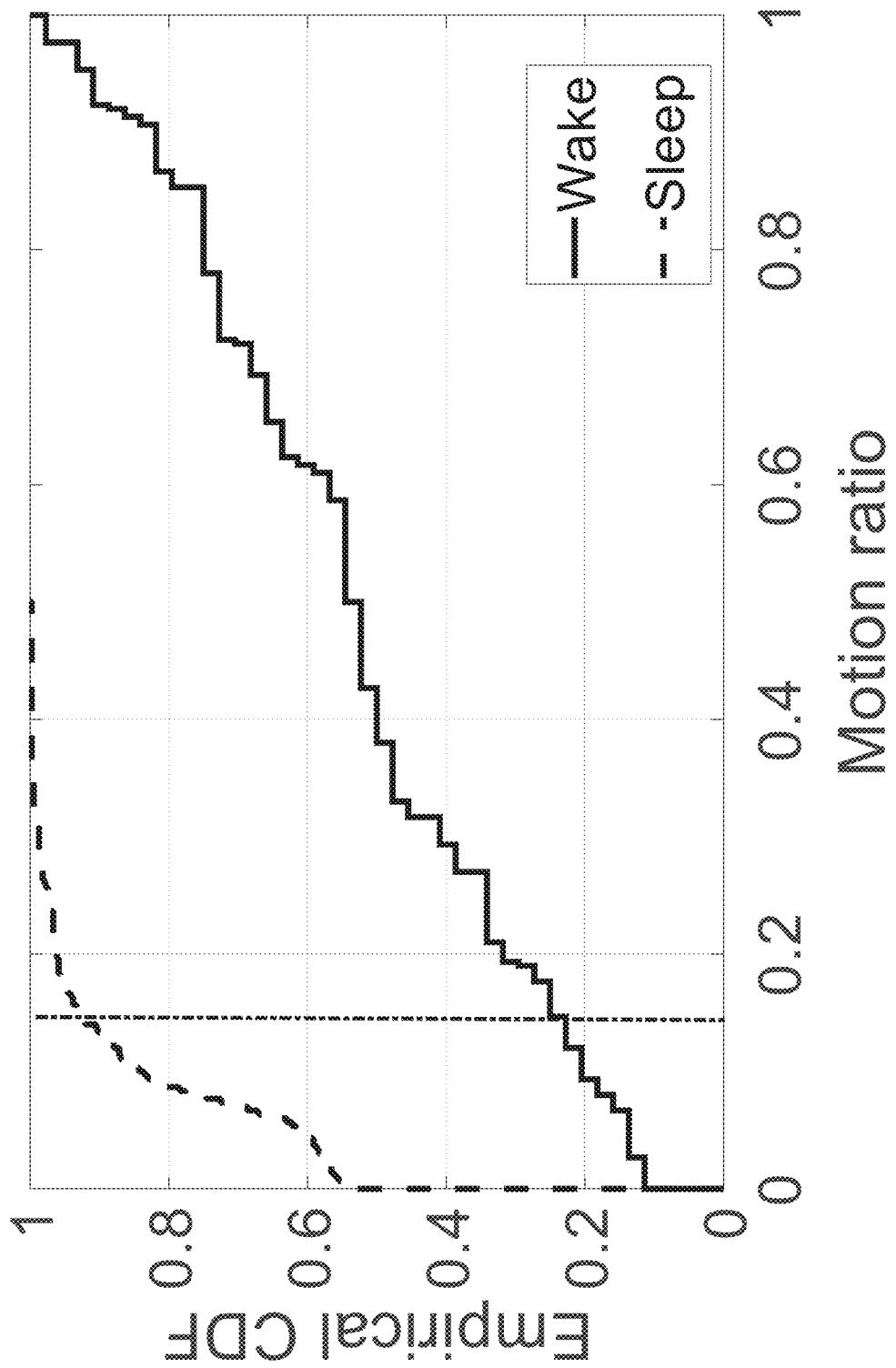
FIG. 6A and FIG. 6B illustrate comparison results between a wake state and a sleep state, according to one embodiment of the present teaching.
Figure 6B:
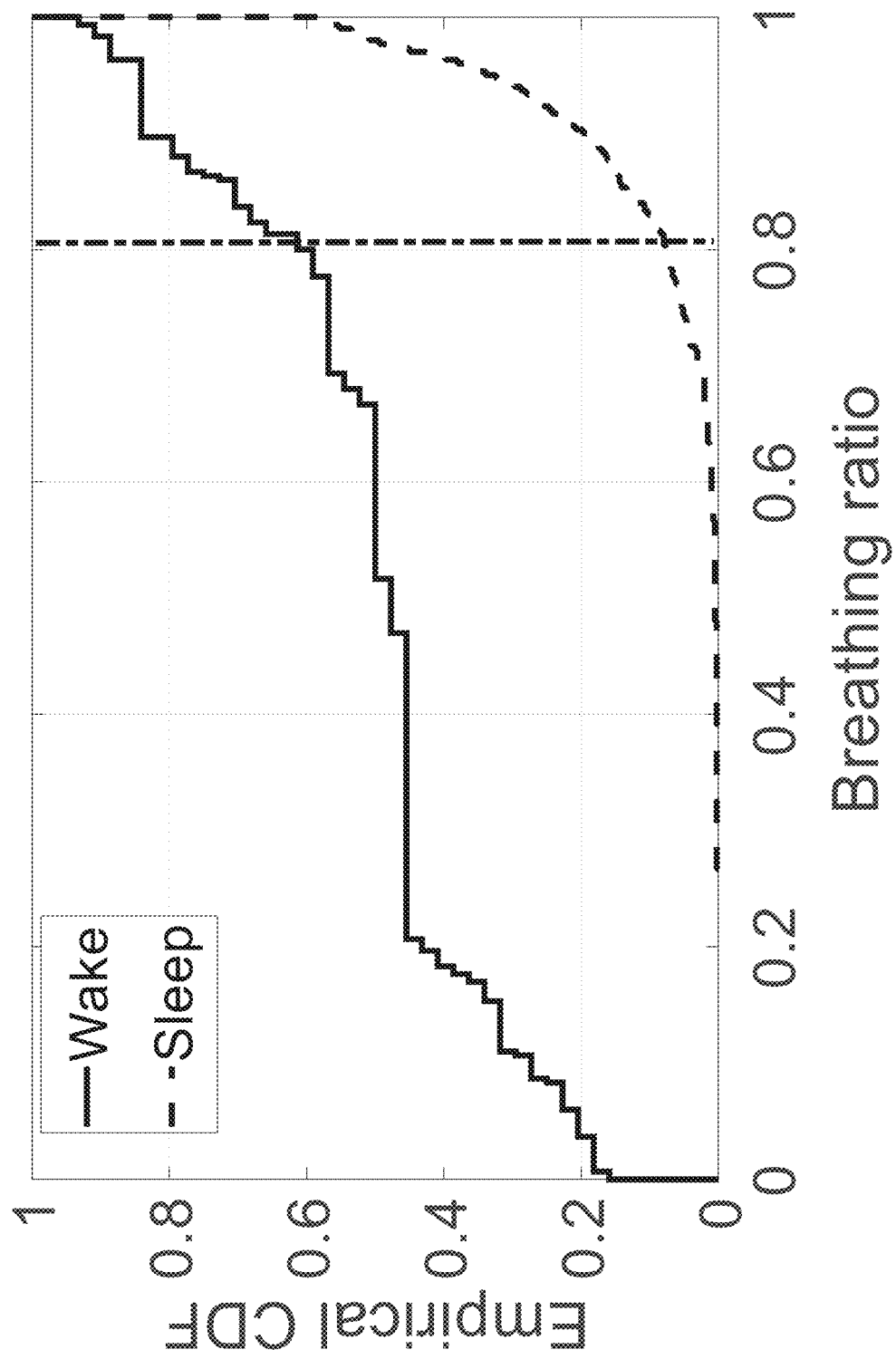

Specifically, one can define motion ratio as the percentage of time when the motion statistic, $\hat{\rho}_b(1/F_s)$, is larger than a preset threshold. Thus for the wake state, a higher motion ratio is expected, as shown in FIG. 6A. Similarly, one can also define breathing ratio as the percentage of time when the breathing signal is detected. Since bodily movements destroy the periodicity of the environmental dynamics, the breathing ratio will be lower when a subject is awake, as shown in FIG. 6B.

Combining the above two features, SMARS identifies an epoch as sleep only when the motion ratio is smaller than the predefined threshold and the breathing ratio is larger than the other threshold. Both thresholds are empirically determined as in FIG. 6A and FIG. 6B. Since the disclosed model statistically considers all multipaths indoors, the values of both thresholds generalize to different environments and subjects.

REM/NREM Recognition. SMARS exploits the following clinical facts and accordingly extracts two distinctive features from breathing rate estimates for REM/NREM stages classification: Breathing rate is usually faster and presents higher variability and irregular patterns for REM stage, while more stable and slower for NREM stage.

Figure 7A:
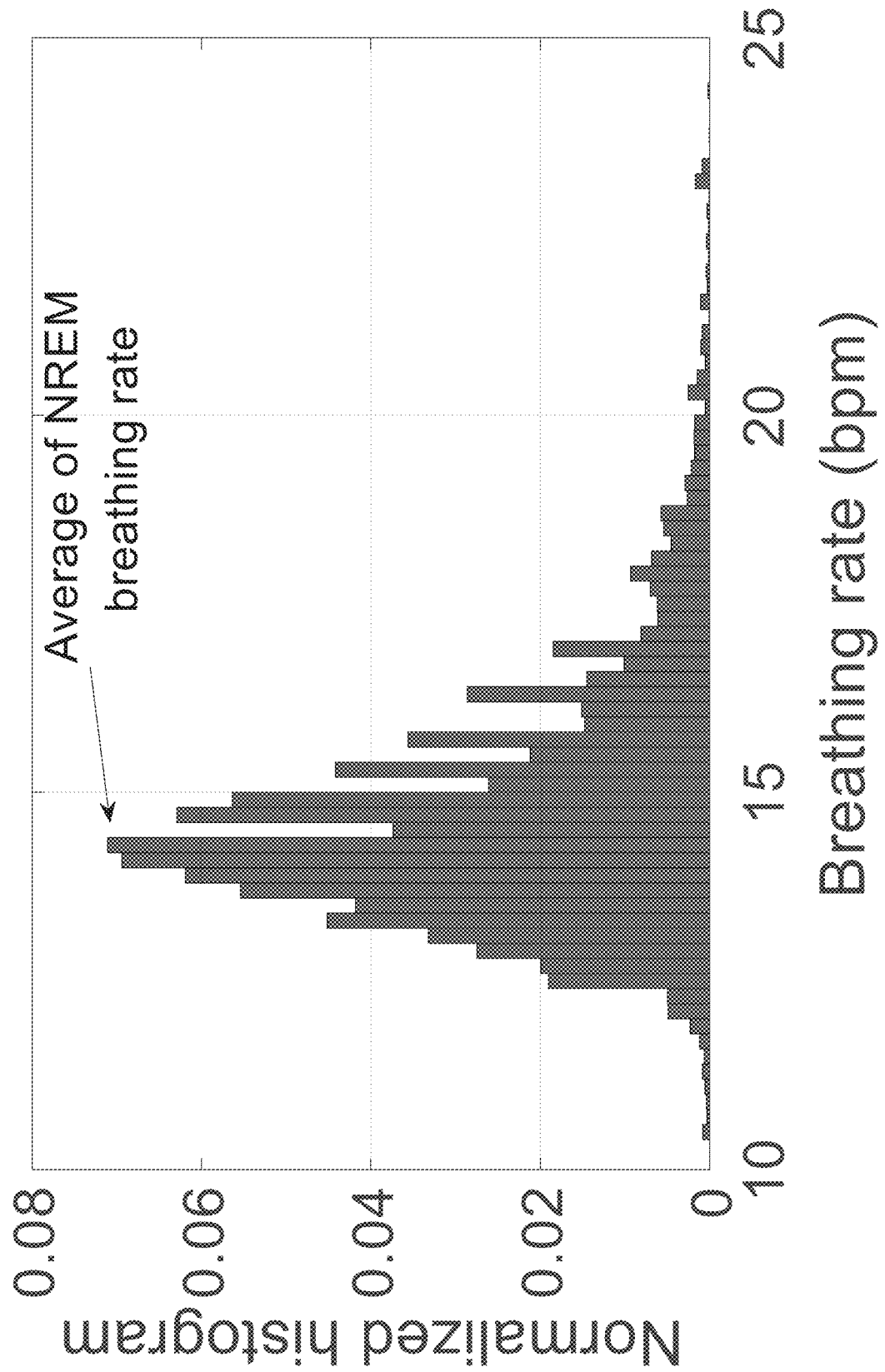
FIG. 7A and FIG. 7B illustrate breathing rate performances of different sleep stages, according to one embodiment of the present teaching.

Since NREM stage constitutes the majority (about 75% to 80%) of total sleep for typical healthy adults, the average breathing rate during NREM stage can be estimated by localizing the peak of the histogram of overnight breathing rate estimates, as shown in FIG. 7A. On this basis, one can define breathing rate deviation, the distance between the estimated average NREM breathing rate and the 90° tile of the breathing rate for each epoch, to quantify the deviation of the breathing rate during REM stage from that during NREM stage.

To extract the variability of the breathing rate for each epoch, one can first estimate the trend of breathing rate by applying a low pass filter to the breathing estimates of the whole night, and obtain the detrended breathing rate estimates by subtracting the trend from the original breathing rate estimates. Then, the breathing rate variability is defined and calculated for each epoch as the variance of the detrended estimates normalized by the length of epoch.

Figure 7B:
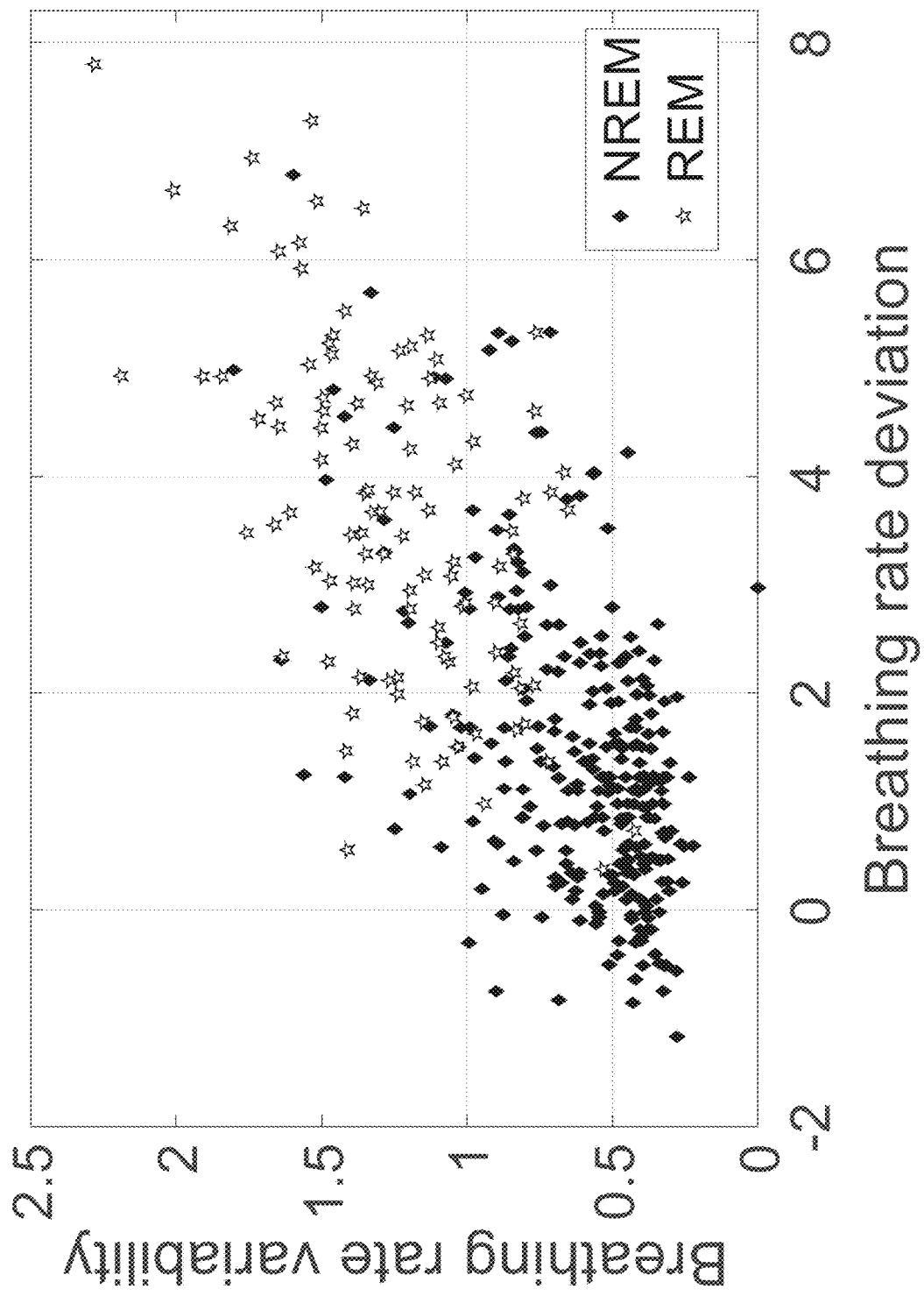

FIG. 7B visualizes the distribution of the proposed two features under NREM and REM sleep, respectively. As one can see from FIG. 7B, the majority of the breathing rate variability and breathing rate deviation of NREM sleep are much smaller than those of REM sleep. Based on these two features, one can train a support vector machine (SVM), a widely used binary classifier, to differentiate between REM and NREM sleep.

Sleep Quality Assessment

When one obtains the estimates of wake, REM, and NREM stages of a whole sleep, one can assess the elusive sleep quality for a user by following standard approach used in clinical practice. In particular, one can calculate the sleep score for each night based on the recognized sleep stages as follows. Let $T_N$, $T_R$ and $T_W$ denote the durations (measured in hours) of NREM sleep, REM sleep and wake, respectively. Since there is no standard formula for sleep score calculation, a simple formula for the sleep score is applied in SMARS:

$$S=10*T_N+20*T_R-10*T_W, \quad (20)$$

which means that the more you sleep, the more you have REM sleep, the less you keep awake in the bed, the better your sleep score is. According to recent research, REM sleep is crucial for mental recovery, and thus a higher weight has been assigned to REM sleep.

SMARS envisions a practical sleep monitoring for daily in-home use. Although it does not make much sense to compare the sleep score among different users, the trend or history of the sleep score for a particular user would reflect the changes of his/her sleep quality. Such results provide clinically meaningful evidences to help diagnose sleep disorders and manage personal health, in an attractive way.

Figure 8:
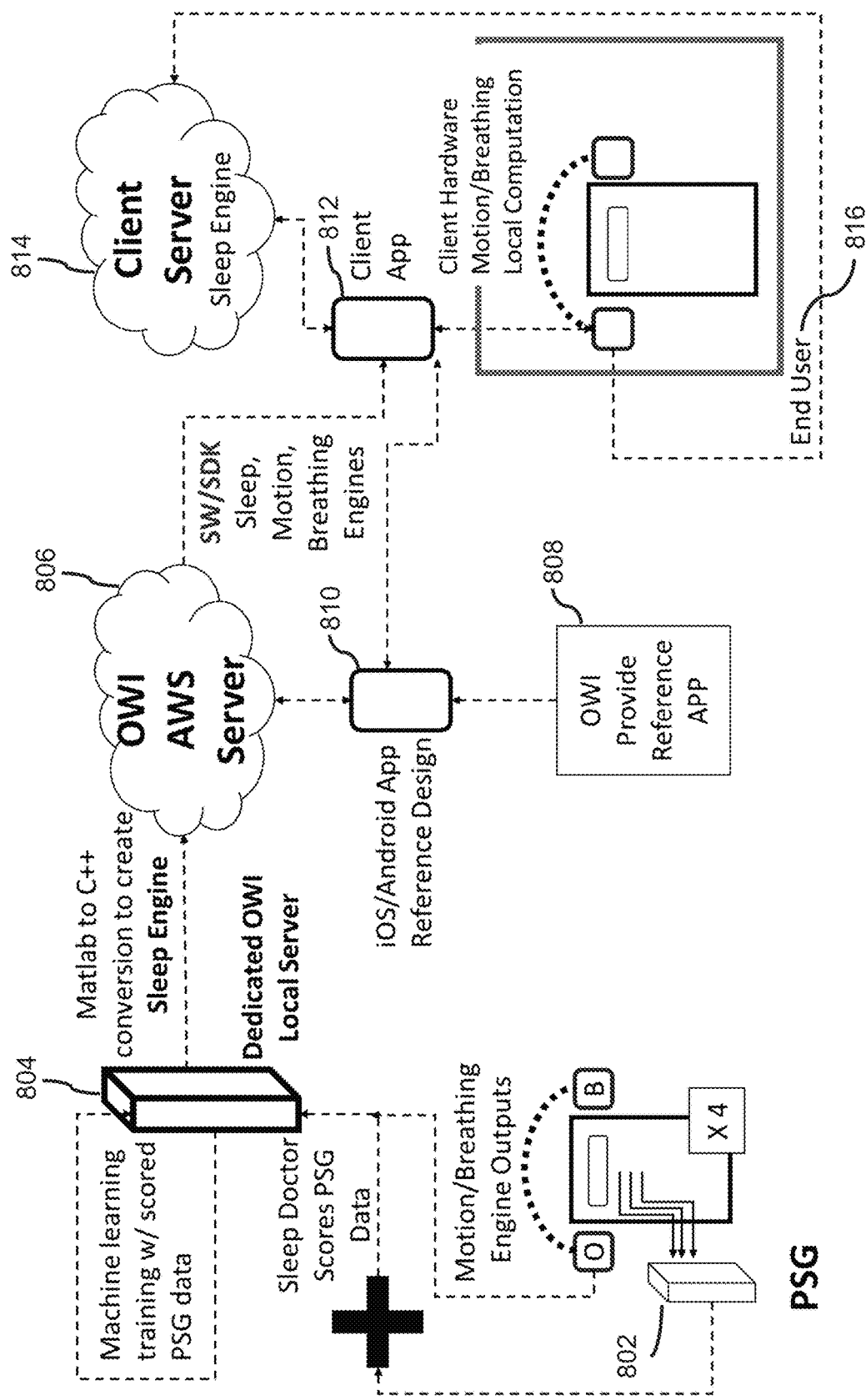
FIG. 8 illustrates an exemplary network environment for sleep monitoring, according to one embodiment of the present teaching.

FIG. 8 illustrates an exemplary network environment for sleep monitoring, according to one embodiment of the present teaching. As shown in FIG. 8, based on an origin (O) and a bot (B), motion/breathing engine outputs can be generated and sent to a polysomnography (PSG) and a dedicated local server 804. The local server 804 may also receive PSG data including e.g. sleep scores from doctors. The local server 804 can perform a training on the scored PSG data based on machine learning to create a sleep engine for a cloud server 806. The cloud server 806 can compute and analyze statistics or sensing features associated with a sleep, to monitor sleep status like motion, breathing, etc. A reference app 808 can implement methods disclosed herein and can be used to generate a designed app for the cloud server 806 and generate a client app 812 for a client server 814. The client server can also work as a sleep engine to monitor sleep motions of an end user 816, based on local computations of motion and breathing statistics using client hardware.

Figure 9:
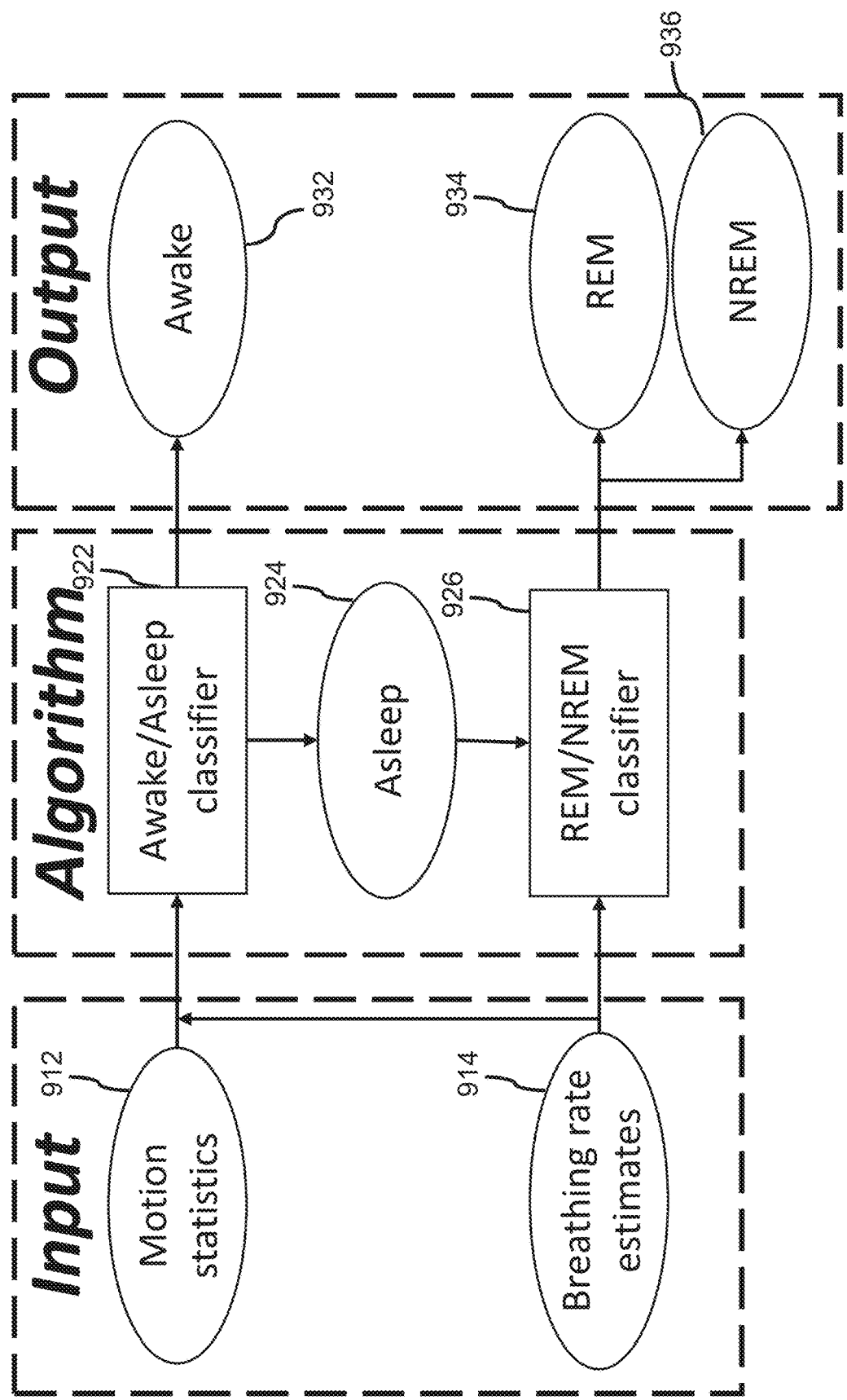
FIG. 9 illustrates an exemplary algorithm design for sleep monitoring, according to one embodiment of the present teaching.

FIG. 9 illustrates an exemplary algorithm design for sleep monitoring, according to one embodiment of the present teaching. As shown in FIG. 9, the inputs to the algorithm include motion statistics 912 and breathing rate estimates 914. Specifically, the motion statistics 912 and the breathing rate estimates 914 are used by an awake/asleep classifier 922 to recognize a sleep state as awake or asleep; while the breathing rate estimates 914 are used by a REM/REM classifier 926. When the sleep state is recognized as awake 932, the awake/asleep classifier 922 sends out the state awake 932 as an output of the algorithm. When the sleep state is recognized as asleep 924, the awake/asleep classifier 922 sends the state asleep 924 to the REM/NREM classifier 926. The REM/NREM classifier 926 then classifies the asleep state as REM sleep 934 or NREM sleep 936, and sends out the classification result as an output of the algorithm.

Figure 10:
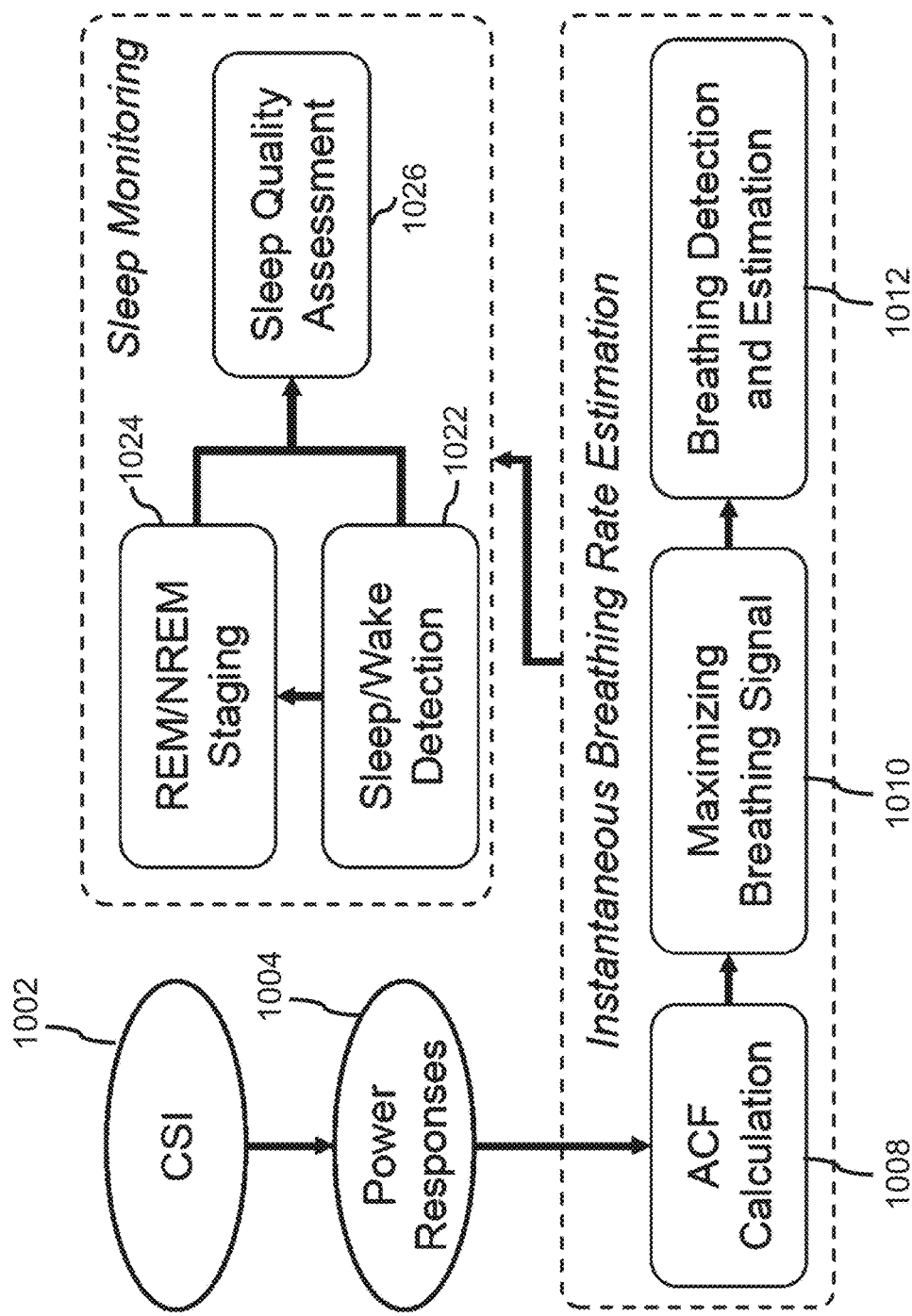
FIG. 10 illustrates another exemplary algorithm design for sleep monitoring, according to one embodiment of the present teaching.

FIG. 10 illustrates another exemplary algorithm design for sleep monitoring, according to one embodiment of the present teaching. As shown in FIG. 10, a CSI 1002 of a multipath channel can be used to generate power responses 1004. The multipath channel is impacted by a sleep motion, e.g. heartbeat or breathing, of a user whose sleep is to be monitored. The autocorrelation function (ACF) can be calculated at operation 1008 based on the power responses, according to methods discussed before. In this embodiment, based on the ACF, breathing signal is maximized at operation 1010, and breathing detection and estimation are performed at operation 1012 based on the maximization. This can generate an estimated breathing rate in real-time, which can be utilized for sleep monitoring. For example, at operation 1022, it can be detected, based on the estimated breathing rate of the user, that whether the user is asleep or awake, e.g. using a data-trained awake/asleep classifier 922 as shown in FIG. 9. The result of the detection is sent out to assess a sleep quality at operation 1026. When it is detected that the user is asleep at operation 1022, another classifier (e.g. the REM/NREM classifier 926 in FIG. 9) can determine the sleep stage as REM or NREM at operation 1024 and send out the sleep stage data for sleep quality assessment at operation 1026 as well.

Figure 11:
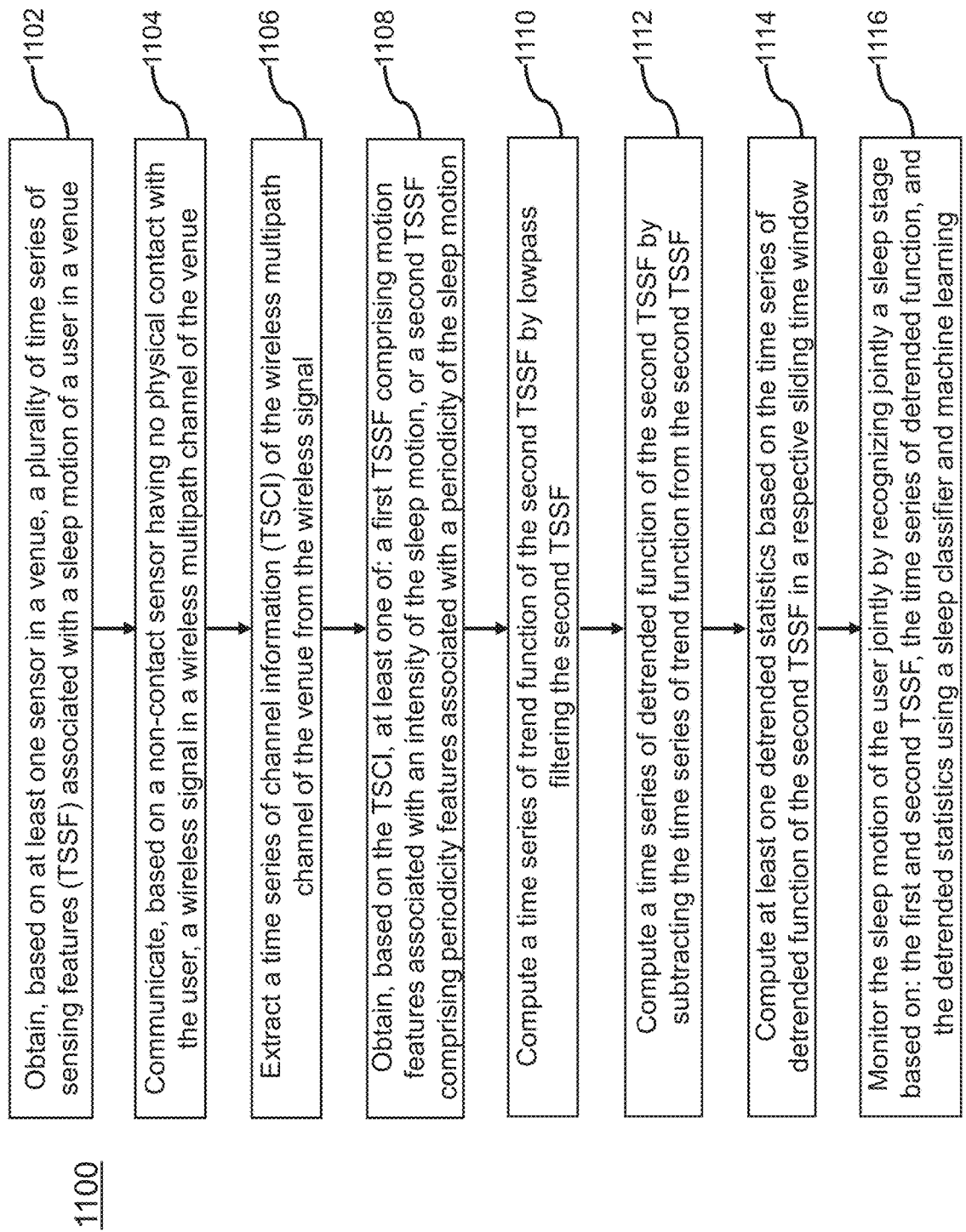
FIG. 11 illustrates a flow chart of an exemplary method of a sleep monitoring system, according to some embodiments of the present teaching.

FIG. 11 illustrates a flow chart of an exemplary method 1100 of a sleep monitoring system, according to some embodiments of the present teaching. At operation 1102, based on at least one sensor in a venue, a plurality of time series of sensing features (TSSF) associated with a sleep motion of a user in a venue is obtained. At operation 1104, based on a non-contact sensor having no physical contact with the user, a wireless signal is communicated in a wireless multipath channel of the venue. At operation 1106, a time series of channel information (TSCI) of the wireless multipath channel of the venue is extracted from the wireless signal. At operation 1108, at least one of the following TSSF is obtained based on the TSCI: a first TSSF comprising motion features associated with an intensity of the sleep motion, or a second TSSF comprising periodicity features associated with a periodicity of the sleep motion. At operation 1110, a time series of trend function of the second TSSF is computed by lowpass filtering the second TSSF. At operation 1112, a time series of detrended function of the second TSSF is computed by subtracting the time series of trend function from the second TSSF. At operation 1114, at least one detrended statistics is computed based on the time series of detrended function of the second TSSF in a respective sliding time window. At operation 1116, the sleep motion of the user is monitored jointly by recognizing jointly a sleep stage of the user based on: the first and second TSSF, the time series of detrended function, and the detrended statistics using a sleep classifier and machine learning. The order of the operations in FIG. 11 may be changed in various embodiments of the present teaching.

The present teaching discloses the system implementation and experimental evaluation of SMARS. One can first conduct field studies to evaluate the performance of SMARS and compare it with medical PSG devices as well as other commercial contact-based solutions. One can then present overnight case studies in 6 homes to show SMARS's capability of monitoring and staging sleep in real-world scenarios.

To obtain ground truth labels of sleep stages, one can resort to the medical gold standard PSG devices. Participants willing to collect PSG data are dressed with a number of contact sensors that record breathing and sleeping data. During sleep, these sensors and the disclosed system are simultaneously recording measurements. In total, one can have five nights of PSG data. The PSG data (mainly EEG) are then annotated with different sleep stages (mainly wake, REM, and NREM), according to the AASM specification. Breathing rate is calculated based on the nasal airflow sensor of PSG.

Comparison. As the disclosed system outperforms the state-of-the-art RF-based sleep monitoring systems in terms of accuracy, coverage and robustness to diverse working conditions, one can choose to compare with radar products and commercial touch-based solutions. Specifically, one can select ResMed, which employs low-power radar technology, and EMFIT, which embeds an array of EMFi sensors into a mat that underpins the mattress. For comparison, one can monitor the participant's sleep with multiple systems simultaneously and compare the overnight outputs of individual technologies. As ResMed only provides stage data but no raw breathing data, one can only compare sleep staging performance with it.

TABLE 1

Comparison of different sleep monitoring systems.

| | Total | Wake | Sleep | REM | NREM |
|---|---|---|---|---|---|
| SMARS | 85.2% | 86.7% | 96.3% | 68.2% | 95.6% |
| EMFIT | 69.8% | 76.7% | 98.2% | 46.3% | 74.9% |
| ResMed | 83.7% | 80.4% | 90.6% | 74.3% | 84.5% |

To compare with advanced commercial solutions, one can simultaneously collect data from all compared systems in addition to PSG as ground truths. One can summarize the accuracy of SMARS compared to two commercial products in Table 1. A confusion matrix of SMARS can show that SMARS yields an overall accuracy of 85% in sleep staging, outperforming commercial solutions EMFIT and ResMed, which use contact sensors and UWB radar respectively. In particular, SMARS achieves a recognition accuracy of 63% and 99% for wake & sleep, which is slightly better than EMFIT and ResMed. For sleep status, SMARS further classifies REM and NREM stages with accuracy of 96% and 84% respectively. As comparison, both EMFIT and ResMed obtain poor accuracy for REM stage and similar to SMARS performance for NREM. Note that EMFIT performs staging with additional heart rate measurements, ResMed further incorporates microphones (from their smartphone App), while SMARS purely relies on breathing estimation.

The following numbered clauses provide additional implementation examples. In various embodiments, a motion ratio may be represented by a percentage of time when motion statistics is larger than threshold; a breathing ratio may be represented by a percentage of time when breathing is detected (breathing not detected in large motion). WAKE may be a state when the motion ratio is high and the breathing ratio is low. REM has a faster breathing rate and higher variability/irregularity than NREM. A breathing rate deviation may be a distance between estimated average NREM breathing rate and 90% percentile of breathing rate for each epoch. A breathing rate variability may be a variance of detrended estimates normalized by epoch length.

Clause 1. A method of a sleep monitoring system, comprising: obtaining a plurality of time series of sensing features (TSSF) associated with a sleep motion of a user in a venue based on a processor, a memory and a set of instructions, each TSSF being associated with a respective sensor in the venue; communicating a wireless signal in a wireless multipath channel of the venue based on a particular sensor which is a wireless non-contact sensor that is not in physical contact with the user; extracting a time series of channel information (TSCI) of the wireless multipath channel of the venue from the wireless signal; obtaining at least one TSSF based on the TSCI; monitoring the sleep motion of the user jointly based on the plurality of TSSF.

Clause 2. The method of the sleep monitoring system of clause 1: wherein monitoring the sleep motion to comprise monitoring at least one of the following of the user: sleep timings, sleep durations, sleep stages, sleep state, sleep quality, sleep apnea, sleep problems, sleep disorders, breathing problems, gasping, choking, teeth-grinding, pause of sleep, absence of sleep, insomnia, restlessness during sleep, hypersomnia, parasomnia, day-time sleepiness, sleep locations, sleep-while-driving, sleep disruptions, nightmares, night terrors, sleep walking, REM sleep behavior disorder, Circadian rhythm disorder, non-24-hour sleep-wake disorder, periodic limb movement disorder, shift-work sleep disorder, narcolepsy, confusional arousals, sleep paralysis, another sleep-related condition, and another sleep-related behavior, wherein sleep timings to comprise timings of at least one of: go-to-bed, sleep-onset, wake-up, REM-onset, NREM-onset, onset of sleep stage transitions, sleep disorders, sleep problems, breathing problems, insomnia, hypersomnia, parasomnia, sleep hypnogram-related events, sleep disruptions, sleep apnea, snoring during sleep, sleeping-not-on-a-bed, day-time sleep, sleep-walking, sleep-related events, sleep-related condition, sleep-related behavior, wherein sleep stages or sleep states comprising at least one of: awake, asleep, light sleep, deep sleep, rapid-eye-movement (REM) and non-REM (NREM).

Clause 3. The method of the sleep monitoring system of clause 1, further comprising: computing at least one of: a time series of sleep states, a time series of sleep stages, a time series of sleep sub-stages, a time series of sleep-related events, a time series of sleep disorder, a time series of sleep problems, a time series of sleep-related conditions, a time series of sleep-related behavior, and a time series of sleep-related activities, based on the plurality of TSSF.

Clause 4. The method of the sleep monitoring system of clause 1, further comprising: wherein a first TSSF comprises sensing features (SF) each being a motion feature associated with an intensity of the sleep motion of the user in the venue; wherein a second TSSF comprises sensing features each being a periodicity feature associated with a periodicity of the sleep motion of the user.

Clause 5. The method of the sleep monitoring system of clause 4: computing each motion feature of the first TSSF based on two adjacent groups of channel information (CI) of the TSCI in a sliding time window, wherein the motion feature comprises at least one of: a magnitude, a phase, a power, a CI magnitude, a CI intensity, a CI feature, a CI component magnitude, a CI component intensity, a CI component feature, a comparison of CI features of the two groups, a distance score, a distance measure, a distance metric, a Euclidean distance, an absolute distance, an L-1 distance, an L-2 distance, an L-k distance, an L-1 norm, an L-2 norm, an L-k norm, a weighted distance, a graph distance, a statistical distance, a similarity score, a similarity measure, a correlation, a correlation indicator, an auto-correlation, a covariance, an auto-covariance, a cross-covariance, a time-reversal resonance strength (TRRS), an inner product, an outer product, a transformation, an FFT, an IFFT, a projection, an amplitude, and a feature.

Clause 6. The method of the sleep monitoring system of clause 4: computing each periodicity feature of the second TSSF based on at least one of: an autocorrelation function (ACF), a frequency spectrum, or a frequency transform, of channel information (CI) of the TSCI in a sliding time window, wherein the periodicity feature is set to a default value of zero if periodicity is not detected in the motion of the user, wherein the periodicity feature comprises at least one of: a frequency, a phase, a rate, a frequency index, a time period, and a time index.

Clause 7. The method of the sleep monitoring system of clause 4, further comprising: monitoring the sleep motion of the user by recognizing a sleep state of the user jointly based on the first TSSF and the second TSSF; computing a motion statistics based on the motion feature of the first TSSF, wherein the motion statistics comprises at least one of: a motion ratio, a motion intensity, a motion power, a motion strength, and a motion significance measure, a percentage of time that the motion feature exceeds a threshold, a percentage of time that the motion feature exceeds the threshold in a sliding time window, a percentage of time that the motion feature is in a significant range, a percentage of time that the motion feature is in the significant range in the sliding time window, a percentage of time that a function of the motion feature exceeds a threshold, a percentage of time that a function of the motion feature exceeds the threshold in a sliding time window, a percentage of time that the function of the motion feature is in a significant range, a percentage of time that the function of the motion feature is in the significant range in the sliding time window; computing a periodicity statistics based on the periodicity features of the second TSSF, wherein the periodicity statistics comprises at least one of: a periodicity feature ratio, a breathing ratio, a heartbeat ratio, a percentage of time that the periodicity feature is non-zero, a percentage of time that the periodicity feature is non-zero in a sliding time window, a percentage of time that the periodicity feature is in a default range, a percentage of time that the periodicity feature is in the default range in a sliding time window, a percentage of time that a breathing rate is non-zero, a percentage of time that a breathing rate is non-zero in a sliding time window, a percentage of time that the breathing rate is in a default range, a percentage of time that the breathing rate is in the default range in a sliding time window, a percentage of time that a heartbeat is non-zero, a percentage of time that a heartbeat is non-zero in a sliding time window, a percentage of time that the heartbeat is in a default range, a percentage of time that the heartbeat is in the default range in a sliding time window; and recognizing a sleep state jointly as either ASLEEP or AWAKE based on the motion statistics, and the periodicity statistics.

Clause 8. The method of the sleep monitoring system of clause 7, further comprising: recognizing the sleep state jointly as ASLEEP if at least one of: the motion statistics and the periodicity statistics satisfy a first joint criterion; and recognizing the sleep state jointly as AWAKE if: the motion statistics and the periodicity statistics satisfy a second joint criterion.

Clause 9. The method of the sleep monitoring system of clause 8, further comprising: wherein the first joint criterion is that the motion statistics is less than a first threshold and the periodicity statistics is larger than a second threshold; wherein the second joint criterion is that the motion statistics is greater than the first threshold or the periodicity statistics is less than the second threshold.

Clause 10. The method of the sleep monitoring system of clause 8, further comprising: wherein the first joint criterion is that the motion statistics is less than a first threshold or the periodicity statistics is larger than a second threshold; wherein the second joint criterion is that motion statistics is greater than a first threshold and the periodicity statistics is less than a second threshold.

Clause 11. The method of the sleep monitoring system of clause 4, further comprising: computing a time series of trend function of the second TSSF by lowpass filtering the second TSSF; computing a time series of detrended function of the second TSSF by subtracting the time series of trend function from the second TSSF; monitoring the sleep motion of the user by computing a sleep stage of the user jointly based on at least one of: the time series of detrended function of the second TSSF, and the first TSSF.

Clause 12. The method of the sleep monitoring system of clause 11, further comprising: computing at least one detrended statistics based on the time series of detrended function of the second TSSF in a respective sliding time window, wherein the at least one detrended statistics comprises: a mean, weighted mean, variance, standard deviation, variation, derivative, slope, total variation, absolute variation, square variation, spread, dispersion, variability, deviation, absolute deviation, square deviation, total deviation, divergence, range, interquartile range, skewness, kurtosis, L-moment, coefficient of variation, quartile coefficient of dispersion, mean absolute difference, Gini coefficient, relative mean difference, median absolute deviation, average absolute deviation, distance standard deviation, coefficient of dispersion, entropy, variance-to-mean ratio, maximum-to-minimum ratio, variation measure, regularity measure, similarity measure, likelihood, probability distribution function, sample distribution, moment generating function, expected value, and expected function; and recognizing jointly the sleep stage as at least one of: REM, NREM, light sleep, deep sleep, sleep apnea, insomnia, hypersomnia, parasomnia, sleep disruption, nightmare, sleep walking, toss-and-turn, a sleep problem, a sleep condition, or a sleep behavior, based on the at least one detrended statistics.

Clause 13. The method of the sleep monitoring system of clause 12, further comprising: applying machine learning to learn a sleep stage classifier, wherein the machine learning comprises at least one of supervised learning, unsupervised learning, semi-supervised learning, active learning, reinforcement learning, support vector machine, deep learning, feature learning, clustering, regression, or dimensionality reduction; and recognizing jointly the sleep stage as at least one of: REM, NREM, light sleep, deep sleep, sleep apnea, insomnia, hypersomnia, parasomnia, sleep disruption, nightmare, sleep walking, toss-and-turn, the sleep problem, the sleep condition, or the sleep behavior, based on the sleep stage classifier.

Clause 14. The method of the sleep monitoring system of clause 12, further comprising: recognizing jointly the sleep stage as at least one of: REM, NREM, light sleep, deep sleep, sleep apnea, insomnia, hypersomnia, parasomnia, sleep disruption, nightmare, sleep walking, toss-and-turn, the sleep problem, the sleep condition, and the sleep behavior, if a sleep state is recognized as ASLEEP.

Clause 15. The method of the sleep monitoring system of clause 12, further comprising: computing a sleep analytics based on at least one of: any sleep stage, any sleep state, the first TSSF, the second TSSF, the plurality of TSSF, and any associated timing, wherein the sleep analytics comprises at least one of; a sleep quality score, a sleep quantity score, a timing, a duration, a sleep-related event occurrence, a sleep-related activity, a sleep-related behavior, a sleep-related stage, a sleep-related state, a sleep problem, a sleep problem score, a sleep disorder, a sleep disorder score, an insomnia, an apnea, a nightmare, the time the user goes to bed, the time the user gets out of bed, the sleep onset time, total time it takes the user to fall asleep, the wake up time, sleep disruption time, number of sleep disruption period, mean disruption duration, variance of disruption duration, total time in bed, total time the user is asleep, time periods of REM, time periods of NREM, time periods of awake, total time of REM, total time of NREM, number of REM periods, number of NREM periods, time of toss and turn in bed, duration of tossing and turning, hypnogram, periods of apnea, periods of snore, total duration of apnea, number of apnea periods, average duration of apnea period, periods of breathing problems, sleep quality score, daytime sleep, time periods of daytime sleep, total duration of daytime sleep, number of period of daytime sleep, average duration of period of daytime sleep, a linear combination of ASLEEP periods with positive coefficients and AWAKE periods with negative coefficients, a weighted sum of positively-weighted REM periods, positively-weighted NREM periods and negatively-weighted AWAKE periods, a fraction of a weighted sum of ASLEEP periods over a weighted sum of AWAKE periods, a fraction of weighted sum of REM periods and NREM periods over a weighted sum of AWAKE periods, an increasing function of at least one of: ASLEEP periods, REM periods and NREM periods, a decreasing function of AWAKE periods, a trend, a daily trend, a weekly trend, a monthly trend, a yearly trend, a repeating trend, a summary, and a history.

Clause 16. A method of a sleep monitoring system, comprising: obtaining a plurality of time series of sensing features (TSSF) associated with a sleep motion of a user in a venue based on a processor, a memory and a set of instructions, wherein each TSSF is associated with a respective sensor in the venue, wherein a first TSSF comprises sensing features (SF) each being a motion feature associated with an intensity of the sleep motion of the user in the venue, wherein a second TSSF comprises sensing features each being a periodicity feature associated with a periodicity of the sleep motion of the user, wherein both the first TSSF and the second TSSF are associated with a particular non-contact sensor that is not in physical contact with the user; monitoring the sleep motion of the user jointly based on the plurality of TSSF.

Clause 17. The method of the sleep monitoring system of clause 16, further comprising: communicating a wireless signal in a wireless multipath channel of the venue in a non-contact manner based on the particular sensor; extracting a time series of channel information (TSCI) of the wireless multipath channel of the venue from the received wireless signal; obtaining the first TSSF and the second TSSF based on the TSCI.

Clause 18. The method of the sleep monitoring system of clause 16, further comprising: monitoring the sleep motion of the user by recognizing a sleep state of the user jointly based on the first TSSF and the second TSSF; computing a motion statistics based on the motion feature of the first TSSF, wherein the motion statistics comprises at least one of: a motion ratio, a motion intensity, a motion power, a motion strength, and a motion significance measure, a percentage of time that the motion feature exceeds a threshold, a percentage of time that the motion feature is in a significant range, a percentage of time that a function of the motion feature exceeds a threshold, and a percentage of time that the function of the motion feature is in a significant range; computing a periodicity statistics based on the periodicity features of the second TSSF, wherein the periodicity statistics comprises at least one of: a periodicity feature ratio, a breathing ratio, a heartbeat ratio, a percentage of time that the periodicity feature is non-zero, a percentage of time that the periodicity feature is in a default range, a percentage of time that a breathing rate is non-zero, a percentage of time that the breathing rate is in a default range, a percentage of time that a heartbeat is non-zero, and a percentage of time that the heartbeat is in a default range; and monitoring the sleep motion of the user jointly by recognizing a sleep state jointly as either ASLEEP or AWAKE based on the motion statistics, and the periodicity statistics.

Clause 19. The method of the sleep monitoring system of clause 16, further comprising: computing a time series of trend function of the second TSSF by lowpass filtering the second TSSF; computing a time series of detrended function of the second TSSF by subtracting the time series of trend function from the second TSSF; computing at least one detrended statistics based on the time series of detrended function of the second TSSF in a respective sliding time window, wherein the at least one detrended statistics comprises: a mean, weighted mean, variance, standard deviation, variation, derivative, slope, total variation, absolute variation, square variation, spread, dispersion, variability, deviation, absolute deviation, square deviation, total deviation, divergence, range, interquartile range, skewness, kurtosis, L-moment, coefficient of variation, quartile coefficient of dispersion, mean absolute difference, Gini coefficient, relative mean difference, median absolute deviation, average absolute deviation, distance standard deviation, coefficient of dispersion, entropy, variance-to-mean ratio, maximum-to-minimum ratio, variation measure, regularity measure, similarity measure, likelihood, probability distribution function, sample distribution, moment generating function, expected value, and expected function; and monitoring the sleep motion of the user jointly by recognizing jointly the sleep stage as at least one of: REM, NREM, light sleep, deep sleep, sleep apnea, insomnia, hypersomnia, parasomnia, sleep disruption, nightmare, sleep walking, toss-and-turn, a sleep problem, a sleep condition, or a sleep behavior, based on the at least one detrended statistics.

Clause 20. The method of the sleep monitoring system of clause 16, further comprising: monitoring the sleep motion of the user jointly by computing a sleep analytics based on at least one of: any sleep stage, any sleep state, the first TSSF, the second TSSF, the plurality of TSSF, and any associated timing, wherein the sleep analytics comprises at least one of: a sleep quality score, a sleep quantity score, a timing, a duration, a sleep-related event occurrence, a sleep-related activity, a sleep-related behavior, a sleep-related stage, a sleep-related state, a sleep problem, a sleep problem score, a sleep disorder, a sleep disorder score, an insomnia, an apnea, a nightmare, the time the user goes to bed, the time the user gets out of bed, the sleep onset time, total time it takes the user to fall asleep, the wake up time, sleep disruption time, number of sleep disruption period, mean disruption duration, variance of disruption duration, total time in bed, total time the user is asleep, time periods of REM, time periods of NREM, time periods of awake, total time of REM, total time of NREM, number of REM periods, number of NREM periods, time of toss and turn in bed, duration of tossing and turning, hypnogram, periods of apnea, periods of snore, total duration of apnea, number of apnea periods, average duration of apnea period, periods of breathing problems, sleep quality score, daytime sleep, time periods of daytime sleep, total duration of daytime sleep, number of period of daytime sleep, average duration of period of daytime sleep, a trend, a daily trend, a weekly trend, a monthly trend, a yearly trend, a repeating trend, a summary, and a history.

Clause 21. A sleep monitoring system, comprising: at least one sensor in a venue; a processor communicatively coupled with a memory and the at least one sensor; the memory; a set of instructions stored in the memory which, when executed by the processor, configure the processor to: obtain a plurality of time series of sensing features (TSSF) associated with a sleep motion of a user in the venue, each TSSF is associated with a respective one of the at least one sensor in the venue, wherein a first TSSF comprises sensing features (SF) each being a motion feature associated with an intensity of the sleep motion of the user in the venue, wherein a second TSSF comprises sensing features each being a periodicity feature associated with a periodicity of the sleep motion of the user, communicate a wireless signal in a wireless multipath channel of the venue based on a particular sensor which is a wireless non-contact sensor that is not in physical contact with the user, extract a time series of channel information (TSCI) of the wireless multipath channel of the venue from the wireless signal, obtain at least one of the first TSSF and the second TSSF based on the TSCI, monitor the sleep motion of the user jointly based on the plurality of TSSF.

Clause 22. The sleep monitoring system of clause 21, the processor is further configured to: monitor the sleep motion of the user by recognizing a sleep state of the user jointly based on the first TSSF and the second TSSF; compute a motion statistics based on the motion feature of the first TSSF, wherein the motion statistics comprises at least one of: a motion ratio, a motion intensity, a motion power, a motion strength, and a motion significance measure, a percentage of time that the motion feature exceeds a threshold, a percentage of time that the motion feature is in a significant range, a percentage of time that a function of the motion feature exceeds a threshold, and a percentage of time that the function of the motion feature is in a significant range; compute a periodicity statistics based on the periodicity features of the second TSSF, wherein the periodicity statistics comprises at least one of a periodicity feature ratio, a breathing ratio, a heartbeat ratio, a percentage of time that the periodicity feature is non-zero, a percentage of time that the periodicity feature is in a default range, a percentage of time that a breathing rate is non-zero, a percentage of time that the breathing rate is in a default range, a percentage of time that a heartbeat is non-zero, and a percentage of time that the heartbeat is in a default range; and monitor the sleep motion of the user jointly by recognizing a sleep state jointly as either ASLEEP or AWAKE based on the motion statistics, and the periodicity statistics.

Clause 23. The sleep monitoring system of clause 21, the processor is further configured to: compute a time series of trend function of the second TSSF by lowpass filtering the second TSSF; compute a time series of detrended function of the second TSSF by subtracting the time series of trend function from the second TSSF; compute at least one detrended statistics based on the time series of detrended function of the second TSSF in a respective sliding time window, wherein the at least one detrended statistics comprises: a mean, weighted mean, variance, standard deviation, variation, derivative, slope, total variation, absolute variation, square variation, spread, dispersion, variability, deviation, absolute deviation, square deviation, total deviation, divergence, range, interquartile range, skewness, kurtosis, L-moment, coefficient of variation, quartile coefficient of dispersion, mean absolute difference, Gini coefficient, relative mean difference, median absolute deviation, average absolute deviation, distance standard deviation, coefficient of dispersion, entropy, variance-to-mean ratio, maximum-to-minimum ratio, variation measure, regularity measure, similarity measure, likelihood, probability distribution function, sample distribution, moment generating function, expected value, and expected function; and monitor the sleep motion of the user jointly by recognizing jointly the sleep stage as at least one of: REM, NREM, light sleep, deep sleep, sleep apnea, insomnia, hypersomnia, parasomnia, sleep disruption, nightmare, sleep walking, toss-and-turn, a sleep problem, a sleep condition, or a sleep behavior, based on the at least one detrended statistics.

Clause 24. The sleep monitoring system of clause 23, the processor is further configured to: apply machine learning to learn a sleep stage classifier; and monitor the sleep motion of the user jointly by recognizing jointly the sleep stage based on the sleep stage classifier, if a sleep state is recognized as ASLEEP.

Clause 25. The sleep monitoring system of clause 21, the processor is further configured to: monitor the sleep motion of the user jointly by computing a sleep analytics based on at least one of: any sleep stage, any sleep state, the first TSSF, the second TSSF, the plurality of TSSF, and any associated timing, wherein the sleep analytics comprises at least one of: a sleep quality score, a sleep quantity score, a timing, a duration, a sleep-related event occurrence, a sleep-related activity, a sleep-related behavior, a sleep-related stage, a sleep-related state, a sleep problem, a sleep problem score, a sleep disorder, a sleep disorder score, an insomnia, an apnea, a nightmare, the time the user goes to bed, the time the user gets out of bed, the sleep onset time, total time it takes the user to fall asleep, the wake up time, sleep disruption time, number of sleep disruption period, mean disruption duration, variance of disruption duration, total time in bed, total time the user is asleep, time periods of REM, time periods of NREM, time periods of awake, total time of REM, total time of NREM, number of REM periods, number of NREM periods, time of toss and turn in bed, duration of tossing and turning, hypnogram, periods of apnea, periods of snore, total duration of apnea, number of apnea periods, average duration of apnea period, periods of breathing problems, sleep quality score, daytime sleep, time periods of daytime sleep, total duration of daytime sleep, number of period of daytime sleep, average duration of period of daytime sleep, a trend, a daily trend, a weekly trend, a monthly trend, a yearly trend, a repeating trend, a summary, and a history.

Clause 26. A server device of a sleep monitoring system, configured to: obtain a plurality of time series of sensing features (TSSF) associated with a sleep motion of a user in a venue based on a processor, a memory and a set of instructions, wherein each TSSF is associated with a respective sensor in the venue, wherein a first TSSF comprises sensing features (SF) each being a motion feature associated with an intensity of the sleep motion of the user in the venue, wherein a second TSSF comprises sensing features each being a periodicity feature associated with a periodicity of the sleep motion of the user, wherein at least one of the first TSSF and the second TSSF is obtained based on a time series of channel information (TSCI) of a wireless multipath channel of the venue, wherein the TSCI is extracted from a wireless signal communicated in a wireless multipath channel of the venue by a particular sensor in the venue; monitor the sleep motion of the user jointly based on the plurality of TSSF.

Clause 27. The server device of the sleep monitoring system of clause 26, further configured to: monitor the sleep motion of the user by recognizing a sleep state of the user jointly based on the first TSSF and the second TSSF;

compute a motion statistics based on the motion feature of the first TSSF, wherein the motion statistics comprises at least one of: a motion ratio, a motion intensity, a motion power, a motion strength, and a motion significance measure, a percentage of time that the motion feature exceeds a threshold, a percentage of time that the motion feature is in a significant range, a percentage of time that a function of the motion feature exceeds a threshold, and a percentage of time that the function of the motion feature is in a significant range; compute a periodicity statistics based on the periodicity features of the second TSSF, wherein the periodicity statistics comprises at least one of: a periodicity feature ratio, a breathing ratio, a heartbeat ratio, a percentage of time that the periodicity feature is non-zero, a percentage of time that the periodicity feature is in a default range, a percentage of time that a breathing rate is non-zero, a percentage of time that the breathing rate is in a default range, a percentage of time that a heartbeat is non-zero, and a percentage of time that the heartbeat is in a default range; and monitor the sleep motion of the user jointly by recognizing a sleep state jointly as either ASLEEP or AWAKE based on the motion statistics, and the periodicity statistics.

Clause 28. The server device of the sleep monitoring system of clause 26, further configured to: compute a time series of trend function of the second TSSF by lowpass filtering the second TSSF; compute a time series of detrended function of the second TSSF by subtracting the time series of trend function from the second TSSF; compute at least one detrended statistics based on the time series of detrended function of the second TSSF in a respective sliding time window, wherein the at least one detrended statistics comprises: a mean, weighted mean, variance, standard deviation, variation, derivative, slope, total variation, absolute variation, square variation, spread, dispersion, variability, deviation, absolute deviation, square deviation, total deviation, divergence, range, interquartile range, skewness, kurtosis, L-moment, coefficient of variation, quartile coefficient of dispersion, mean absolute difference, Gini coefficient, relative mean difference, median absolute deviation, average absolute deviation, distance standard deviation, coefficient of dispersion, entropy, variance-to-mean ratio, maximum-to-minimum ratio, variation measure, regularity measure, similarity measure, likelihood, probability distribution function, sample distribution, moment generating function, expected value, and expected function; and monitor the sleep motion of the user jointly by recognizing jointly the sleep stage as at least one of: REM, NREM, light sleep, deep sleep, sleep apnea, insomnia, hypersomnia, parasomnia, sleep disruption, nightmare, sleep walking, toss-and-turn, a sleep problem, a sleep condition, or a sleep behavior, based on the at least one detrended statistics.

Clause 29. The server device of the sleep monitoring system of clause 28, further configured to: apply machine learning to learn a sleep stage classifier; and monitor the sleep motion of the user jointly by recognizing jointly the sleep stage based on the sleep stage classifier, if a sleep state is recognized as ASLEEP.

Clause 30. The server device of the sleep monitoring system of clause 26, further configured to: monitor the sleep motion of the user jointly by computing a sleep analytics based on at least one of: any sleep stage, any sleep state, the first TSSF, the second TSSF, the plurality of TSSF, and any associated timing, wherein the sleep analytics comprises at least one of: a sleep quality score, a sleep quantity score, a timing, a duration, a sleep-related event occurrence, a sleep-related activity, a sleep-related behavior, a sleep-related stage, a sleep-related state, a sleep problem, a sleep problem score, a sleep disorder, a sleep disorder score, an insomnia, an apnea, a nightmare, the time the user goes to bed, the time the user gets out of bed, the sleep onset time, total time it takes the user to fall asleep, the wake up time, sleep disruption time, number of sleep disruption period, mean disruption duration, variance of disruption duration, total time in bed, total time the user is asleep, time periods of REM, time periods of NREM, time periods of awake, total time of REM, total time of NREM, number of REM periods, number of NREM periods, time of toss and turn in bed, duration of tossing and turning, hypnogram, periods of apnea, periods of snore, total duration of apnea, number of apnea periods, average duration of apnea period, periods of breathing problems, sleep quality score, daytime sleep, time periods of daytime sleep, total duration of daytime sleep, number of period of daytime sleep, average duration of period of daytime sleep, a trend, a daily trend, a weekly trend, a monthly trend, a yearly trend, a repeating trend, a summary, and a history.

The features described above may be implemented advantageously in one or more computer programs that are executable on a programmable system including at least one programmable processor coupled to receive data and instructions from, and to transmit data and instructions to, a data storage system, at least one input device, and at least one output device. A computer program is a set of instructions that may be used, directly or indirectly, in a computer to perform a certain activity or bring about a certain result. A computer program may be written in any form of programming language (e.g., C, Java), including compiled or interpreted languages, and it may be deployed in any form, including as a stand-alone program or as a module, component, subroutine, a browser-based web application, or other unit suitable for use in a computing environment.

Suitable processors for the execution of a program of instructions include, e.g., both general and special purpose microprocessors, digital signal processors, and the sole processor or one of multiple processors or cores, of any kind of computer. Generally, a processor will receive instructions and data from a read-only memory or a random access memory or both. The essential elements of a computer are a processor for executing instructions and one or more memories for storing instructions and data. Generally, a computer will also include, or be operatively coupled to communicate with, one or more mass storage devices for storing data files; such devices include magnetic disks, such as internal hard disks and removable disks; magneto-optical disks; and optical disks. Storage devices suitable for tangibly embodying computer program instructions and data include all forms of non-volatile memory, including by way of example semiconductor memory devices, such as EPROM, EEPROM, and flash memory devices; magnetic disks such as internal hard disks and removable disks; magneto-optical disks; and CD-ROM and DVD-ROM disks. The processor and the memory may be supplemented by, or incorporated in, ASICs (application-specific integrated circuits).

While the present teaching contains many specific implementation details, these should not be construed as limitations on the scope of the present teaching or of what may be claimed, but rather as descriptions of features specific to particular embodiments of the present teaching. Certain features that are described in this specification in the context of separate embodiments may also be implemented in combination in a single embodiment. Conversely, various features that are described in the context of a single embodiment may also be implemented in multiple embodiments separately or in any suitable sub-combination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the embodiments described above should not be understood as requiring such separation in all embodiments, and it should be understood that the described program components and systems may generally be integrated together in a single software product or packaged into multiple software products.

Particular embodiments of the subject matter have been described. Any combination of the features and architectures described above is intended to be within the scope of the following claims. Other embodiments are also within the scope of the following claims. In some cases, the actions recited in the claims may be performed in a different order and still achieve desirable results. In addition, the processes depicted in the accompanying figures do not necessarily require the particular order shown, or sequential order, to achieve desirable results. In certain implementations, multitasking and parallel processing may be advantageous.

We claim:

1. A system for monitoring a sleep motion of a user in a venue, comprising:
at least one sensor in the venue, wherein the at least one sensor comprises a wireless non-contact sensor having no physical contact with the user;
a processor communicatively coupled to the at least one sensor;
a memory communicatively coupled to the processor; and
a set of instructions stored in the memory which, when executed by the processor, causes the processor to perform:
obtaining, based on the at least one sensor, a plurality of time series of sensing features (TSSF) associated with the sleep motion of the user in the venue, wherein at least one TSSF of the plurality of TSSF is obtained by:
communicating, based on the wireless non-contact sensor, a wireless signal in a wireless multipath channel of the venue,
extracting a time series of channel information (TSCI) of the wireless multipath channel of the venue from the wireless signal, and
obtaining the at least one TSSF based on the TSCI,
wherein obtaining the plurality of TSSF comprises:
computing a first TSSF based on the TSCI, wherein each sensing feature (SF) of the first TSSF comprises one of: a distance score, a Euclidean distance, a similarity score, a correlation, a covariance, or an inner product, based on two adjacent groups of channel information (CI) of the TSCI,
computing a second TSSF comprising periodicity features associated with a periodicity of the sleep motion of the user, wherein the second TSSF is associated with a breathing rate of the user,
computing a time series of trend function of the second TSSF by lowpass filtering the second TSSF,
computing a time series of detrended function of the second TSSF by subtracting the time series of trend function from the second TSSF; and
monitoring the sleep motion of the user jointly based on the plurality of TSSF and the time series of detrended function of the second TSSF,
wherein monitoring the sleep motion of the user comprises:
training a sleep classifier based on data related to breathing rate variance and breathing rate deviation, using machine learning,
computing a first time function of breathing rate variance by computing variance of a detrended breathing rate function within a first sliding time window,
computing a second time function of breathing rate deviation by computing a distance between an average non-rapid-eye-movement (NREM) breathing rate and a percentile of breathing rate within a second sliding time window,
recognizing jointly, based on the sleep classifier, a sleep stage of the user as one of rapid-eye-movement (REM) or NREM based on the first time function of breathing rate variance and the second time function of breathing rate deviation.

2. The system of claim 1, wherein:
monitoring the sleep motion comprises monitoring at least one of the following of the user: sleep timings, sleep durations, sleep stages, sleep states, sleep quality, sleep apnea, sleep problems, or sleep disorders.

3. The system of claim 1, wherein the set of instructions, when executed by the processor, further causes the processor to perform:
computing, based on the plurality of TSSF, at least one of: a time series of sleep stages, or a time series of sleep sub-stages, wherein at least one of the sleep stages is related to: rapid-eye-movement (REM) or non-REM (NREM).

4. The system of claim 3, wherein the set of instructions, when executed by the processor, further causes the processor to perform:
computing each motion feature of the first TSSF based on two adjacent groups of channel information (CI) of the TSCI in a sliding time window, wherein each motion feature comprises at least one of: a distance score, a Euclidean distance, a similarity score, a correlation, a covariance, an inner product, an outer product, or a transformation.

5. The system of claim 3, wherein the set of instructions, when executed by the processor, further causes the processor to perform:
computing each periodicity feature of the second TSSF based on at least one of the following of channel information (CI) of the TSCI in a sliding time window: an autocorrelation function (ACF), a frequency spectrum, or a frequency transform, wherein:
each periodicity feature is set to a default value when the periodicity is not detected in the sleep motion of the user,
each periodicity feature comprises at least one of: a frequency, a phase, a rate, a frequency index, a time period, or a time index.

6. The system of claim 3, wherein the set of instructions, when executed by the processor, further causes the processor to perform:
monitoring the sleep motion of the user by recognizing a sleep state of the user jointly based on the first TSSF and the second TSSF;

computing a motion statistics based on a motion feature of the first TSSF, wherein the motion statistics comprises at least one of:
- a motion ratio, a percentage of time that a function of the motion feature exceeds a threshold, or
- a percentage of time that a function of the motion feature exceeds the threshold in a sliding time window;

computing a periodicity statistics based on a periodicity feature of the second TSSF, wherein the periodicity statistics comprises at least one of:
- a periodicity feature ratio, a breathing ratio, a heartbeat ratio,
- a percentage of time that the periodicity feature is not a default value (non-default), or
- a percentage of time that the periodicity feature is non-default in a sliding time window; and recognizing the sleep state jointly as either ASLEEP or AWAKE based on the motion statistics and the periodicity statistics.

7. The system of claim 6, wherein:
the sleep state is recognized jointly as ASLEEP when the motion statistics or the periodicity statistics satisfy a first joint criterion; and
the sleep state is recognized jointly as AWAKE when the motion statistics or the periodicity statistics satisfy a second joint criterion.

8. The system of claim 7, wherein:
the first joint criterion is that: the motion statistics is less than a first threshold and the periodicity statistics is greater than a second threshold; and
the second joint criterion is that: the motion statistics is greater than the first threshold or the periodicity statistics is less than the second threshold.

9. The system of claim 7, wherein:
the first joint criterion is that: the motion statistics is less than a first threshold or the periodicity statistics is greater than a second threshold; and
the second joint criterion is that: the motion statistics is greater than the first threshold and the periodicity statistics is less than the second threshold.

10. The system of claim 1, wherein
the average NREM breathing rate is computed by identifying a peak of a histogram of a time function of breathing rate in an ASLEEP stage in an overnight period; and
the sleep classifier is further trained based on scored polysomnography data.

11. The system of claim 1, wherein the set of instructions, when executed by the processor, further causes the processor to perform:
computing at least one detrended statistics based on the time series of detrended function of the second TSSF in a respective sliding time window, wherein the at least one detrended statistics comprises at least one of: a mean, a weighted mean, a variance, or a deviation; and
recognizing jointly, based on the at least one detrended statistics, the sleep stage as at least one of: REM, NREM, light sleep, deep sleep, sleep apnea, insomnia, hypersomnia, parasomnia, sleep disruption, nightmare, sleep walking, toss-and-turn, a sleep problem, a sleep condition, or a sleep behavior.

12. The system of claim 1,
wherein the machine learning comprises at least one of: supervised learning, unsupervised learning, semi-supervised learning, active learning, reinforcement learning, support vector machine, deep learning, feature learning, clustering, regression, or dimensionality reduction.

13. The system of claim 11, wherein the set of instructions, when executed by the processor, further causes the processor to perform:
recognizing jointly the sleep stage as at least one of: REM, NREM, light sleep, deep sleep, sleep apnea, insomnia, hypersomnia, parasomnia, sleep disruption, nightmare, sleep walking, toss-and-turn, the sleep problem, the sleep condition, or the sleep behavior, when a sleep state of the user is recognized as ASLEEP.

14. The system of claim 11, wherein the set of instructions, when executed by the processor, further causes the processor to perform:
computing a sleep analytics based on at least one of: any sleep stage, any sleep state, the first TSSF, the second TSSF, the plurality of TSSF, or any associated timing,
wherein the sleep analytics comprises at least one of: a sleep quality score, a sleep quantity score, a timing, a duration, or a linear combination of ASLEEP periods with positive coefficients and AWAKE periods with negative coefficients.

15. A system for monitoring a sleep motion of a user in a venue, comprising:
at least one sensor in the venue, wherein the at least one sensor comprises a non-contact sensor having no physical contact with the user;
a processor communicatively coupled to the at least one sensor;
a memory communicatively coupled to the processor; and
a set of instructions stored in the memory which, when executed by the processor, causes the processor to perform:
communicating a wireless signal in a wireless multipath channel of the venue in a non-contact manner based on the non-contact sensor;
extracting a time series of channel information (TSCI) of the wireless multipath channel of the venue from the wireless signal;
obtaining, based on the at least one sensor, a plurality of time series of sensing features (TSSF) associated with the sleep motion of the user in the venue, wherein:
the plurality of TSSF comprises a first TSSF and a second TSSF,
each sensing feature (SF) of the first TSSF comprises one of: a distance score, a Euclidean distance, a similarity score, a correlation, a covariance, or an inner product, based on two adjacent groups of channel information (CI) of the TSCI,
the second TSSF comprises periodicity features associated with a periodicity of the sleep motion of the user,
the second TSSF is associated with a breathing rate of the user,
both the first TSSF and the second TSSF are obtained based on the non-contact sensor; and
monitoring the sleep motion of the user jointly based on the plurality of TSSF,
wherein monitoring the sleep motion of the user comprises:
training a sleep classifier based on data related to breathing rate variance and breathing rate deviation, using machine learning, computing a first time function of breathing rate variance by computing variance of a detrended breathing rate function within a first sliding time window, computing a second time function of breathing rate deviation by computing a distance between an average non-rapid-eye-movement (NREM) breathing rate and a percentile of breathing rate within a second sliding time window, recognizing jointly, based on the sleep classifier, a sleep stage of the user as one of rapid-eye-movement (REM) or NREM based on the first time function of breathing rate variance and the second time function of breathing rate deviation.

16. The system of claim 15, wherein the set of instructions, when executed by the processor, further causes the processor to perform:

communicating a wireless signal in a wireless multipath channel of the venue in a non-contact manner based on the non-contact sensor;

extracting a time series of channel information (TSCI) of the wireless multipath channel of the venue from the wireless signal; and obtaining the first TSSF and the second TSSF based on the TSCI.

17. The system of claim 15, wherein the set of instructions, when executed by the processor, further causes the processor to perform:

monitoring the sleep motion of the user by recognizing a sleep state of the user jointly based on the first TSSF and the second TSSF;

computing a motion statistics based on motion features of the first TSSF, wherein the motion statistics comprises at least one of:
- a motion ratio, a motion intensity, a motion power, a motion strength, or a percentage of time that the motion feature exceeds a threshold;

computing a periodicity statistics based on periodicity features of the second TSSF, wherein each periodicity feature of the second TSSF is equal to a default value when the periodicity is not detected in the sleep motion of the user, wherein the periodicity statistics comprises at least one of:
- a periodicity feature ratio, a breathing ratio, a heartbeat ratio,
- a percentage of time that the periodicity feature is not the default value (non-default),
- a percentage of time that a breathing rate is non-default, or
- a percentage of time that a heartbeat is non-default, wherein the sleep state is recognized jointly as either ASLEEP or AWAKE based on the motion statistics and the periodicity statistics.

18. The system of claim 15, wherein the set of instructions, when executed by the processor, further causes the processor to perform:

computing a time series of trend function of the second TSSF by lowpass filtering the second TSSF;

computing a time series of detrended function of the second TSSF by subtracting the time series of trend function from the second TSSF;

computing at least one detrended statistics based on the time series of detrended function of the second TSSF in a respective sliding time window, wherein the at least one detrended statistics comprises: a mean, a weighted mean, a variance, or a deviation; and monitoring the sleep motion of the user jointly by recognizing jointly a sleep stage of the user as at least one of: REM, NREM, light sleep, deep sleep, sleep apnea, insomnia, hypersomnia, parasomnia, sleep disruption, nightmare, sleep walking, toss-and-turn, a sleep problem, a sleep condition, or a sleep behavior, based on the at least one detrended statistics.

19. The system of claim 15, wherein the set of instructions, when executed by the processor, further causes the processor to perform:

monitoring the sleep motion of the user jointly by computing a sleep analytics based on at least one of: any sleep stage, any sleep state, the first TSSF, the second TSSF, the plurality of TSSF, or any associated timing, wherein the sleep analytics comprises at least one of: a sleep quality score, a sleep quantity score, a timing, or a duration.

20. A method of a sleep monitoring system, comprising:

obtaining, based on at least one sensor in a venue, a plurality of time series of sensing features (TSSF) associated with a sleep motion of a user in the venue;

communicating, based on a non-contact sensor having no physical contact with the user, a wireless signal in a wireless multipath channel of the venue;

extracting a time series of channel information (TSCI) of the wireless multipath channel of the venue from the wireless signal, wherein:
- the plurality of TSSF comprises a first TSSF and a second TSSF,
- the second TSSF comprises periodicity features associated with a periodicity of the sleep motion of the user,
- the second TSSF is associated with a breathing rate of the user; and monitoring the sleep motion of the user jointly based on the plurality of TSSF, wherein monitoring the sleep motion of the user comprises:
- training a sleep classifier based on data related to breathing rate variance and breathing rate deviation, using machine learning,
- computing a first time function of breathing rate variance by computing variance of a detrended breathing rate function within a first sliding time window,
- computing a second time function of breathing rate deviation by computing a distance between an average non-rapid-eye-movement (NREM) breathing rate and a percentile of breathing rate within a second sliding time window,
- recognizing jointly, based on the sleep classifier, a sleep stage of the user as one of rapid-eye-movement (REM) or NREM based on the first time function of breathing rate variance and the second time function of breathing rate deviation.

21. The method of claim 20, further comprising:

monitoring the sleep motion of the user by recognizing a sleep state of the user jointly based on the first TSSF and the second TSSF;

computing a motion statistics based on motion features of the first TSSF in a first sliding time window, wherein the motion statistics comprises at least one of:
- a motion ratio, a motion intensity, a motion power, a motion strength, or
- a percentage of time that the motion feature exceeds a threshold;

computing a periodicity statistics based on periodicity features of the second TSSF in a second sliding time window, wherein each periodicity feature of the second TSSF is set to a default value when the periodicity is not detected in the sleep motion of the user, wherein the periodicity statistics comprises at least one of:
a periodicity feature ratio, a breathing ratio, a heartbeat ratio,
a percentage of time that the periodicity feature is not the default value (non-default),
a percentage of time that a breathing rate is non-default,
a percentage of time that a heartbeat is non-default, wherein the sleep state is recognized jointly as either ASLEEP or AWAKE based on the motion statistics and the periodicity statistics.

22. The method of claim 20, further comprising:
computing a time series of trend function of the second TSSF by lowpass filtering the second TSSF;
computing a time series of detrended function of the second TSSF by subtracting the time series of trend function from the second TSSF;
computing at least one detrended statistics based on the time series of detrended function of the second TSSF in a respective sliding time window, wherein the at least one detrended statistics comprises: a mean, a weighted mean, a variance, or a deviation; and
monitoring the sleep motion of the user jointly by recognizing jointly a sleep stage of the user as at least one of: REM, NREM, light sleep, deep sleep, sleep apnea, insomnia, hypersomnia, parasomnia, sleep disruption, nightmare, sleep walking, toss-and-turn, a sleep problem, a sleep condition, or a sleep behavior, based on the at least one detrended statistics.

23. The method of claim 22,
wherein the average NREM breathing rate is computed by identifying a peak of a histogram of a time function of breathing rate in an ASLEEP stage in an overnight period.

24. The method of claim 20, further comprising:
monitoring the sleep motion of the user jointly by computing a sleep analytics based on at least one of: any sleep stage, any sleep state, the first TSSF, the second TSSF, the plurality of TSSF, or any associated timing,
wherein the sleep analytics comprises at least one of: a sleep quality score, a sleep quantity score, a timing, or a duration.

25. A server device of a sleep monitoring system, comprising:
a processor communicatively coupled to at least one sensor in a venue;
a memory communicatively coupled to the processor; and
a set of instructions stored in the memory which, when executed by the processor, causes the processor to perform:
obtaining a plurality of time series of sensing features (TSSF) associated with a sleep motion of a user in the venue, wherein:
each of the plurality of TSSF is associated with a respective sensor of the at least one sensor,
the plurality of TSSF comprises a first TSSF and a second TSSF,
the second TSSF comprises periodicity features associated with a periodicity of the sleep motion of the user,
the second TSSF is associated with a breathing rate of the user, at least one of the first TSSF or the second TSSF is obtained based on a time series of channel information (TSCI) of a wireless multipath channel of the venue,
the TSCI is extracted from a wireless signal communicated in the wireless multipath channel of the venue by one of the at least one sensor in the venue; and monitoring the sleep motion of the user jointly based on the plurality of TSSF,
wherein monitoring the sleep motion of the user comprises:
training a sleep classifier based on data related to breathing rate variance and breathing rate deviation, using machine learning,
computing a first time function of breathing rate variance by computing variance of a detrended breathing rate function within a first sliding time window,
computing a second time function of breathing rate deviation by computing a distance between an average non-rapid-eye-movement (NREM) breathing rate and a percentile of breathing rate within a second sliding time window,
recognizing jointly, based on the sleep classifier, a sleep stage of the user as one of rapid-eye-movement (REM) or NREM based on the first time function of breathing rate variance and the second time function of breathing rate deviation.

26. The server device of claim 25, wherein the set of instructions, when executed by the processor, further causes the processor to perform:
monitoring the sleep motion of the user by recognizing a sleep state of the user jointly based on the first TSSF and the second TSSF;
computing a motion statistics based on motion features of the first TSSF in a first sliding time window, wherein the motion statistics comprises at least one of:
a motion ratio, a motion intensity, a motion power, a motion strength, or
a percentage of time that the motion feature exceeds a threshold;
computing a periodicity statistics based on periodicity features of the second TSSF in a second sliding time window, wherein each periodicity feature is set to a default value when the periodicity is not detected in the sleep motion of the user,
wherein the periodicity statistics comprises at least one of:
a periodicity feature ratio, a breathing ratio, a heartbeat ratio,
a percentage of time that the periodicity feature is not the default value (non-default),
a percentage of time that a breathing rate is non-default,
a percentage of time that a heartbeat is non-default,
wherein the sleep state is recognized jointly as either ASLEEP or AWAKE based on the motion statistics and the periodicity statistics.

27. The server device of claim 25, wherein the set of instructions, when executed by the processor, further causes the processor to perform:
computing a time series of trend function of the second TSSF by lowpass filtering the second TSSF;
computing a time series of detrended function of the second TSSF by subtracting the time series of trend function from the second TSSF;
computing at least one detrended statistics based on the time series of detrended function of the second TSSF in a respective sliding time window, wherein the at least one detrended statistics comprises: a mean, a weighted mean, a variance, or a deviation; and monitoring the sleep motion of the user jointly by recognizing jointly a sleep stage of the user as at least one of: REM, NREM, light sleep, deep sleep, sleep apnea, insomnia, hypersomnia, parasomnia, sleep disruption, nightmare, sleep walking, toss-and-turn, a sleep problem, a sleep condition, or a sleep behavior, based on the at least one detrended statistics.

28. The server device of claim 27, wherein the average NREM breathing rate is computed by identifying a peak of a histogram of a time function of breathing rate in an ASLEEP stage in an overnight period.

29. The server device of claim 25, wherein the set of instructions, when executed by the processor, further causes the processor to perform:

monitoring the sleep motion of the user jointly by computing a sleep analytics based on at least one of: any sleep stage, any sleep state, the first TSSF, the second TSSF, the plurality of TSSF, or any associated timing, wherein the sleep analytics comprises at least one of: a sleep quality score, a sleep quantity score, a timing, or a duration.

* * * * *